(12) United States Patent
Pauli et al.

(10) Patent No.: US 7,338,937 B2
(45) Date of Patent: Mar. 4, 2008

(54) CALCIUM-ACTIVATED CHLORIDE CHANNEL PROTEINS AND THEIR USE IN ANTI-METASTATIC THERAPY

(75) Inventors: Bendicht U. Pauli, Brooktondale, NY (US); Randolph C. Elble, Ithaca, NY (US); Achim D. Gruber, Hanover (DE)

(73) Assignee: Cornell Research Foundation, Inc., Ithaca, NY (US)

( * ) Notice: Subject to any disclaimer, the term of this patent is extended or adjusted under 35 U.S.C. 154(b) by 301 days.

(21) Appl. No.: 10/779,949

(22) Filed: Feb. 17, 2004

(65) Prior Publication Data

US 2004/0265859 A1 Dec. 30, 2004

Related U.S. Application Data

(60) Continuation-in-part of application No. 10/055,412, filed on Oct. 29, 2001, now Pat. No. 6,692,939, which is a division of application No. 09/193,562, filed on Nov. 17, 1998, now Pat. No. 6,309,857.

(60) Provisional application No. 60/065,922, filed on Nov. 17, 1997.

(51) Int. Cl.
*A61K 38/04* (2006.01)
(52) U.S. Cl. .......................... 514/15; 514/12; 530/328; 530/350
(58) Field of Classification Search .................. 514/12; 530/328, 350
See application file for complete search history.

(56) References Cited

U.S. PATENT DOCUMENTS 5,340,727 A * 8/1994 Ruggeri et al. ............ 435/69.6
6,426,072 B1 * 7/2002 Wang et al. ............. 424/184.1

FOREIGN PATENT DOCUMENTS

DE 19924199 A1 * 11/2000
WO WO 9947674 A2 * 9/1999
WO WO 0061612 A2 * 10/2000
WO WO 0140521 A2 * 6/2001

OTHER PUBLICATIONS

Guan et al. (J. Biol. Chem. 1992; 267: 10024-10030).*
Abdel-Ghany, Mossaad, Hung-Chi Cheng, Randolph C. Elble, Haiqun Lin, John Dibiasio, and Bendicht U. Pauli, "The Interacting Binding Domains Of The $\beta_4$ Integrin And Calcium-Activated Chloride Channels (CLCAs) In Metastasis," *The Journal Of Biological Chemistry*, Dec. 5, 2003, pp. 49406-49416, vol. 278, No. 49, JBC Papers In Press.
Gruber, Achim D., Kevin D. Schreur, Hong-Long Ji, Catherine M. Fuller, and Bendicht U. Pauli, "Molecular Cloning And Transmembrane Structure Of hCLCA2 From Human Lung, Trachea, And Mammary Gland," *Am. J. Physiol.*, 1999, pp. C1261-C1270, vol. 276.
Kerem, Bat-Sheva, Johanna M. Rommens, Janet A. Buchanan, Danuta Markiewicz, Tara K. Cox, Aravinda Chakravarti, Manuel Buchwald, and Lap-Chee Tsui, "Identification Of The Cystic Fibrosis Gene: Genetic Analysis," *Science*, Sep. 8, 1989, pp. 1073-1080, vol. 245.
Welsh, Michael J. and Alan E. Smith, "Molecular Mechanisms Of CFTR Chloride Channel Dysfunction In Cystic Fibrosis," *Cell*, Jul. 2, 1993, pp. 1251-1254, vol. 73.

* cited by examiner

*Primary Examiner*—Shanon Foley
*Assistant Examiner*—Brandon Fetterolf
(74) *Attorney, Agent, or Firm*—Hodgson Russ LLP

(57) ABSTRACT

Nucleotide sequences which encode a mammalian lung endothelial cell adhesion molecule are disclosed. Also disclosed are nucleotide sequences which encode a lung endothelial cell adhesion molecule-associated protein. Recombinant lung endo-thelial cell adhesion molecule or recombinant lung endothelial cell adhesion molecule-associated protein may be obtained by culturing in a medium a host cell genetically engineered to contain and express a nucleotide sequence according to the present invention, and recovering the recombinant lung endothelial cell adhesion molecule-associated protein or recombinant lung endothelial cell adhesion molecule-associated protein from the culture medium.

6 Claims, 23 Drawing Sheets

Replacement Sheet

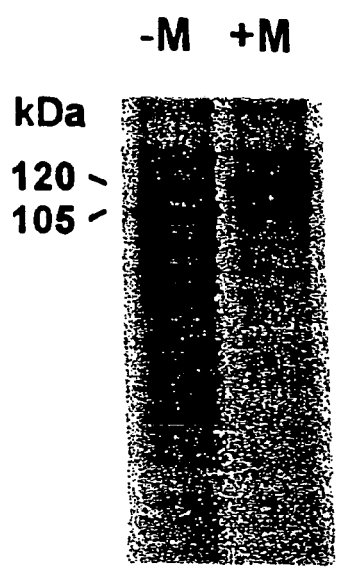
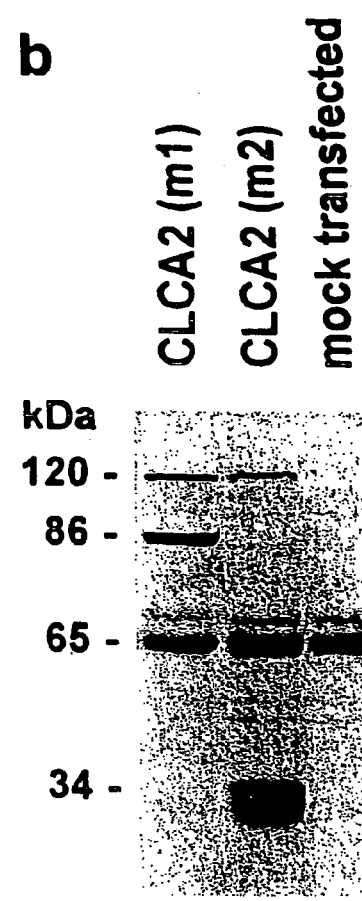
Figure 8

Figure 14

| Figure 14A |
|---|
| Figure 14B |

Figure 14A

```
h CLCA2    MTQRSIAGPICNLKFVTLLVALSSELPFLGAGVQLQDNGYNGLLIAINPQVPENQNLISNIKEMITEASFYLFNATKRRV  80
h CLCA1    .GPFKSS----VFILI.HL-.EGA.S--NSLI..NN...E.IVV..D.N...DET..QQ..D.V.Q..L...E.GK.F   72
b CLCA1    .VP.LTV-----IL.L...HL-.PG-MK--SSM.N.IN...D.IV......S....DEK..Q.......V......T...H.......  71
Lu-ECAM-1  .VLCLNV-----IL.L...HL-.PG-MK--SSM.N.IN...D.IV......S....DEK..E.......V......T...H.......  71
m CLCA1    .VPGLQV-----L.L..HL-.QN-TE--SSM.H.NS...E.VV......S....DER..PS......V.Q..T...E.SQG..  71 h CLCA2    FFRNIKILIPATWKANNN-SKIKQESYEKANVITDWYGAHGDDPYTLQYRGCGKEGKYIHFTPNFLLNDNLTAGYGSRG  159
h CLCA1    Y.K.VA....E....TKADYVRP.L.T.KN.D.L.AESTPPGN.E...E.MGN..EK.ER..L..D.IAGKK.AE-..PQ..  151
b CLCA1    Y....VS.......M..SKSEYLMP.....DQ.E...ANP.LK.........GR..EK.Q.............TN..PI---..  150
Lu-ECAM-1  Y....VS.......M..SKSEYFIP.....DQ.D...ANP.LKY........GR..EK...............TN.FHI---..  150
m CLCA1    Y....S..V.M..SKSEYLMP.R....D...D...A.PHLQ........GQ..DR.Q..............T....RI-..P-..  150 h CLCA2    RVFVHEWAHLRWGVFDEYNNDKPFYINGQNQIKVTRCSSDITGIFV----CEKGPCPQENCIISK---LFKEGCTFIYNS  232
h CLCA1    KA...........EK..LS-NGR.QAV...AG...TN.V-KK.QG.S.YTKR.TFN.VTG.YEK..E.VLQ.  229
b CLCA1    .A...........I......G.Q..SRR.T.EA.....TH...TN.IVK-..QG.S.ITRP.RRDSQTG.YEAK...PEK  229
Lu-ECAM-1  ...............I......V.Q..SRK.T.EA.....TH.....N.VFKK.PG.S.ITSL.RRDSQTG.YEAK...LPKK  230
m CLCA1    ................V.R..SRK.T.EA...AS...KK.V-HE.QR.S.VTRA.RRDSKTR.YEPK...PDK  229 h CLCA2    TQNATASIMFMQSLSSVVEFCNASTHNQEAPNLQNQMCSLRSAWDVITDSADFHHSFPMHGTELPPPPTFSLVQAGDKVV  312
h CLCA1    R.TEK....A.HVD.I...TEQN..K.....K....K.N...T.E..R..E..KKTI..TT-.Q..N.......L.I.QRI.  307
b CLCA1    S.T.RE............H..T...TEK..V.......K..NGK.T...MN.T..QNTS..TEMNP.TQ......LKSKQR.  309
S CLCA1    S.T.KE............P..H..T...TEK..V.......K..NGK.T...MN.V..QNTS..TEMNP.TH......LKSKQR.  310
Lu-ECAM-1  I.T.G.............N.N.......TENH..A.......K..NR..T......KT......QNAP..R...A.....Y.LKSRRR.  309 h CLCA2    CLVLDVSSKMAEADRLLQLQQAAEFYLMQIVEIHTFVGIASFDSKGEIRAQLHQINSNDDRKLLVSYLPTTVSAKTDISI  392
h CLCA1    ....K.GS..TGN..NR.N..GQLF.L.T..LGSW..MVT...AAHVQSE.I....GS..DT.AKR..AA---.SGGT..  385
b CLCA1    ....K.GS..SSE..FRMN.....LF.I...I.KGSL..MVT.....VA...NN.TK.TDDNVYENITAN..QE--.NGGT.  387
Lu-ECAM-1  ....K.GS..SAE...F.MN.....L...I.VI.KGSL..MVT.....VA..QNH.TR.TDDNVYQKITAK..QV--.NGGT.  388
m CLCA1    ....K.GS..DKE...IRMN.....L..T.....KESM..LVT.....AAH.QNY.IK.T.SS.YQKITAN..QQ--.SGGT..  387 h CLCA2    CSGLKKGFEVVEKLNGKAYGSVMILVTSGDDKLLGNCLPTVLSSGSTIHSIALGSSAAPNLEELSRLTGGLKFFVPDISN  472
h CLCA1    RSA.-T.IRKKYPTD..EIV.L.D.E.NTISG.FNE.KQ..AI..TV...P..QE.....KM...QTYAS.QVQ  464
b CLCA1    .R...A..QAIIQSQSTS..EI..L.D.E.NEIHS.IEE.KQ..VI...T....P..KE..T..DM..HR.YANKDI-  466
Lu-ECAM-1  .R...A..QAIIHSDQSTS..EI..L.D.E.NEINS.FED.KR..AI...T....P..KE..T..NM..YR..ANKDI-  467
m CLCA1    .H...QA..QAITSSDQSTS..EIV.L.D.E.NGIRS.FEA.SR..AI...T....P.R.RE..T..DM....R.YANKDL-  466
```

```
h CLCA2    SNSMIDAFSRISSGTDIFQQHIQLESTGENVKPHHQLKNTVTVDNTVGNDTMFLVTWQASGPPEIILFDPDGRKYYTNN  552
h CLCA1    N.GL.....GAL...N.AVS.RS......K.LTLQNSQWMNG..I..S...K..L.I...TTQ.Q.L.W..S.Q.--QGG  541
b CLCA1    -.GLTN.........RS.S.T..T......KALAITEKKWVNG..P..S.I.....F.V...TIKK...L.Q..K.K..K.SD  544
Lu-ECAM-1  -TGLTN.........RS.S.T..A......KALKITGRKRVNG..P..S.......F.V...TIQK...V.Q..K.K..K.SD  545
m CLCA1    ...L..........TS.SVS..AL.....KAFD.RAGAWING..PL.S.......F.VI..-MVKK.....Q..K.K..T.SD  544 h CLCA2    FITN-LTFRTASLWIPGTAKPGHWTYTLNNTHHSLQALKVTVTSRASNSAVPPATVEAFVERDSLHFPHPVNIYANVKQG  631
h CLCA1    .VVDK-NTKM.Y.Q...I..V.T.K.S.---QA.S.T.TL.....ATL..I..TSKTNK.TSK..S.LVV...IR..      617
b CLCA1    .KEDK.NIHS.R.R...I..I.ET.T....S.L.N.A.P.I.T....T..RSPTT..V.AT.HMSQNTA.Y.S..IV..Q.S.  624
Lu-ECAM-1  .KEDK.NI.S.R.Q...I..I.ET.T....S.L.N.A.S.M.T....T..RSPTI..VIAT.HMSQHTA.Y.S.MIV..Q.S.  625
m CLCA1    .QDDK.NI.S.R.Q...ET.T...SY--.GTKS.LITM....T..RSPTME.LLGYCYMSQSTAQY.SRMIV..R.S..     622 h CLCA2    FYPILNATVTATVEPETGDPVTLRLLDDGAGADVIKNDGIYSRYFFSFAANGRYSLKVHVNHSPSISTPAHSIPGSHAMY  711
h CLCA1    AS...R.S...LI.SVN.KT...E...N.....AT.D..V......TTYDT....V..RALGGVNAARRVIPQQ.G.L.    697
b CLCA1    .L.V.GIN...II.T.D.HQ...E.W.N......TV..........TDYRG.........AEARNNTARLSLRQ.QNK.L.   704
Lu-ECAM-1  .L.V.GIS.I.II.T.D.HQ...E.W.N......R.TV..........TDYYG..........AQARNNTARLNLRQ.QNKVL. 705
m CLCA1    .L.V.G.N...LI.A.H.HQ...E.W.N......IV..........T..TDYHG.........R.QAQRNKTRLSLRQ-KNKSL. 701 h CLCA2    VPGYTANGNIQMNAPRKSVGRNEEERKWG-FSRVSSGGSFSVLG-VPAGPHPDVFPPCKIIDLEA-VKVEEELTLSWTAP   788
h CLCA1    I..WIE.DE..W.P..PEINKDDVQH.QVC...T......-.ASD..NA.I..L...GQ.T..K.EIHGGSLIN.T...    776
b CLCA1    .IE..K.IL.P..PE.KDDLAKAEIED....LT......T.S.AP.-.N...S.L..N.....KF.ED-HIQ......    782
Lu-ECAM-1  ....VE..K.IL.P..PE.KDDLAKA.IED....LT......T.S.AP.P.N...S.....T......KF.ED-YIQ......    784
m CLCA1    ....VE..K.VL.P..PD.QEEAI.ATVED.N..T......T.S.AP.D.D.AR....S.VT......EFIGD-YIH.T...    780 h CLCA2    GEDFDQGQATSYEIRMSKSLQNIQDDFNNAILVNTSKRNPQQAGIREIFTFSPQISTNGPEHQPNGETHESHRIYVAIRA  868
h CLCA1    .D.Y.H.T.HK.I...I.T.ILDLR.K..ESLQ...TALI.KE.NSE.V.L.K.ENI-------FENGTDLFI..Q.     846
b CLCA1    ANVL.K.K.N...I....I....FLDL.K..D..T......SLK.KE..SD.N.E.K.EPFR-------IENGTNF.I.VQ. 852
Lu-ECAM-1  .NVL.K.K.N...I....I....FMDR.E..D..T......NLI.KE..SK.N.E.K.EHFR-------VENGTKF.ISVQ. 854
m CLCA1    .KVL.N.R.HR.I....QHPLDL.E........T.....A.SLI.KE..SK..A.K.K.ETFK-------IANGIQL.I..Q. 850 h CLCA2    MDRNSLQSAVSNIAQAPLFIPPNSDP-VPARDYLILKGVLTAMGLIGICLLIIVTHHTLSRKKRADKKENGTKLL         943
h CLCA1    V.KVD.K.EI...RVS....QTP.ET.SP.---ETSAPCPN-.H.NST.PGIHILKIMW.WIG----.LQLSIA          914
b CLCA1    INEAN.T.E......IK....MP----------------EDSVP.L.-TK.SAINLAIFALAMI---------LSIV.     904
Lu-ECAM-1  INEAN.I.E..H.V..IK...LP----------------EDSVHDL.-TK.SEITLAILGLPMI---------FSV-F      905
m CLCA1    DNEA..T.E.......VKLTSL---------------VKLTSL-----EDSIS.L.-DD.SAISMTIWGL.VI----------FNSI.N  902
```

Figure 14B

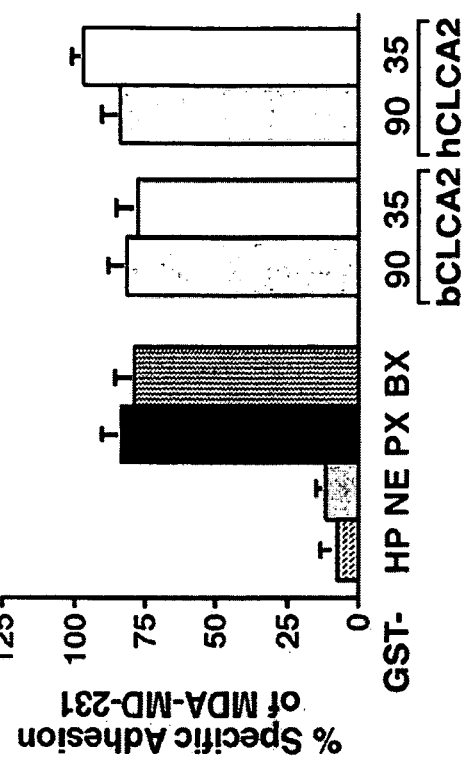
Fig. 15B
Fig. 15D
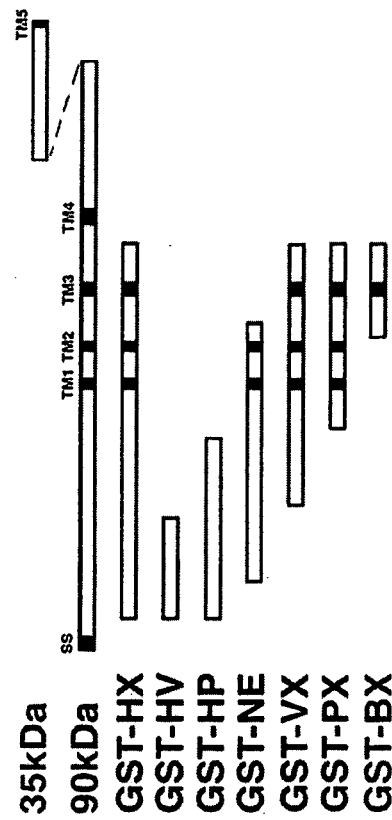
Fig. 15A
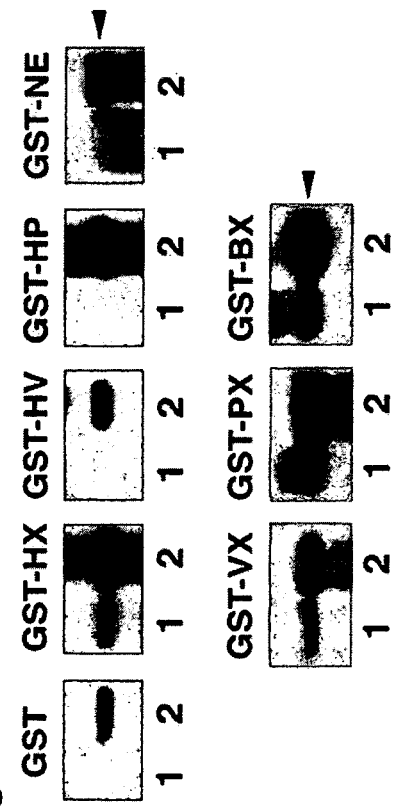
Fig. 15C

Fig. 16A
| | 90-kDa | 35-kDa |
|---|---|---|
| hCLCA2 | AFSRISSGTG | GFSRVSSGGS |
| mCLCA5 | AFVRISSGTG | GFSRVSSGGS |
| mCLCA1 | AFSRISSTSG | DFNRVTSGGS |
| bCLCA2 | AFSRISSRSG | DFSRLTSGGS |
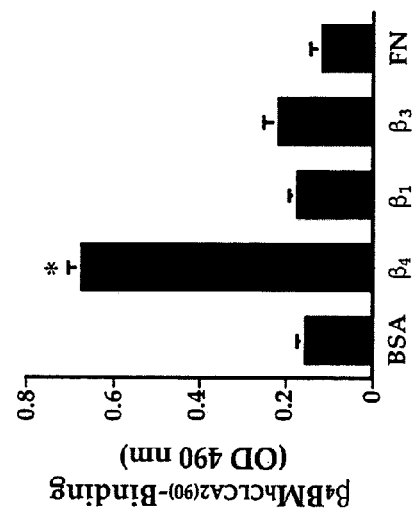
Fig. 16B
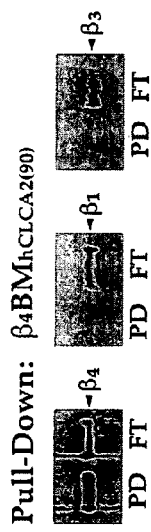
Fig. 16C
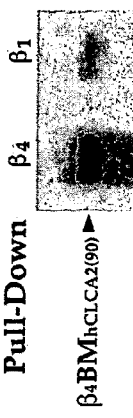
Fig. 16D

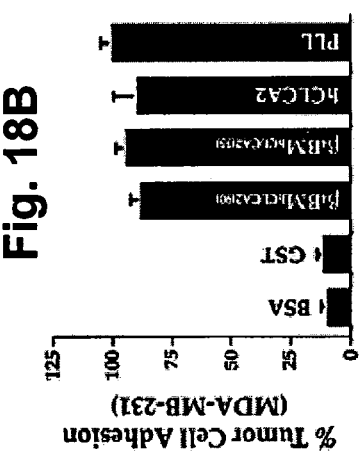
Fig. 18B
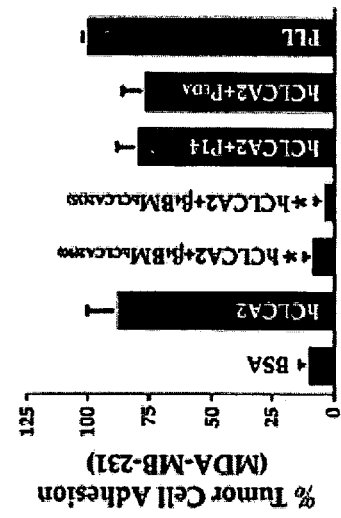
Fig. 18C
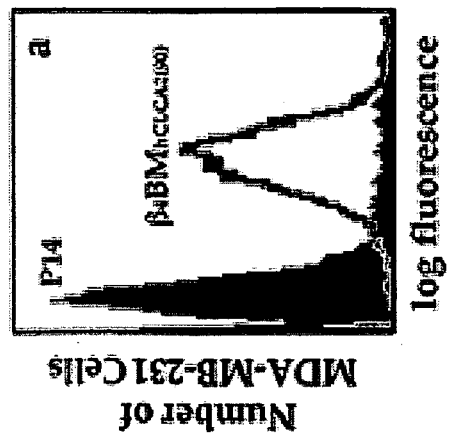
Fig. 18 A
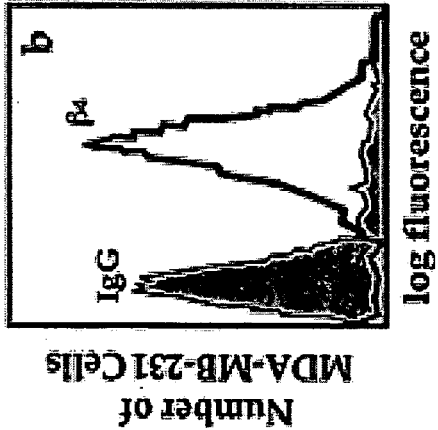

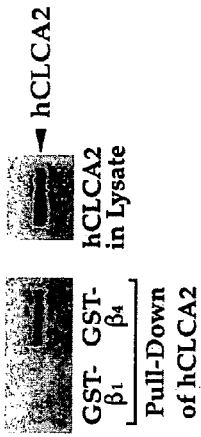
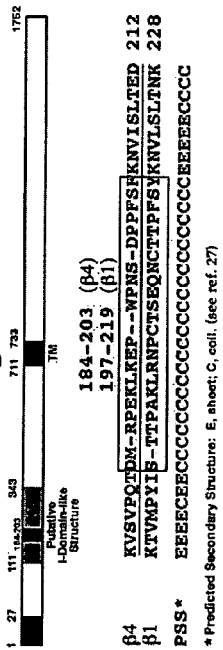
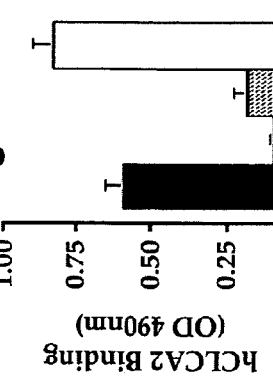
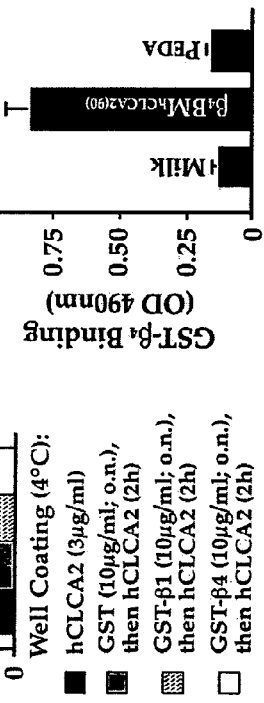
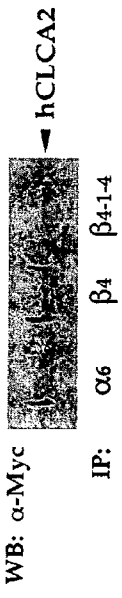

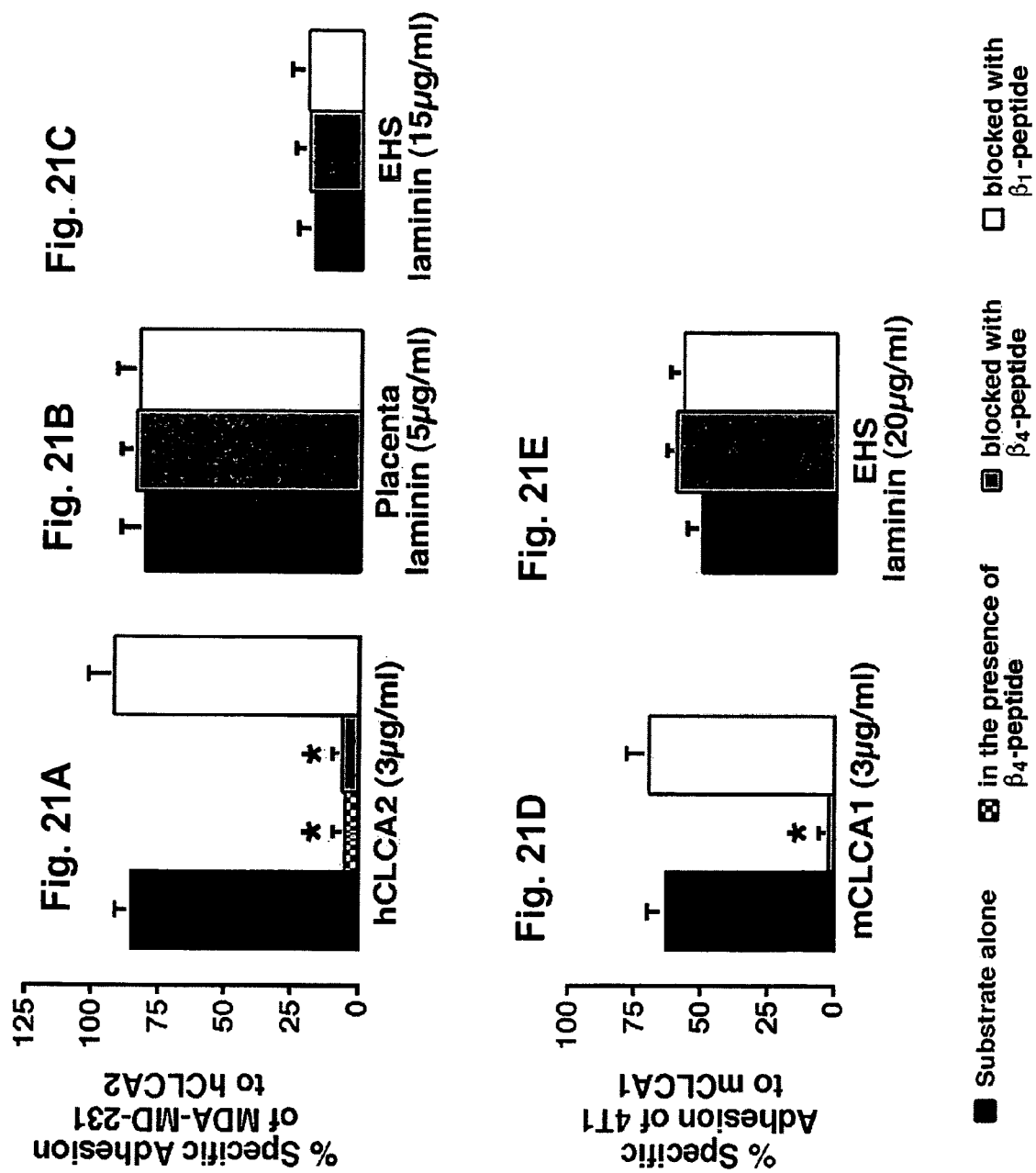

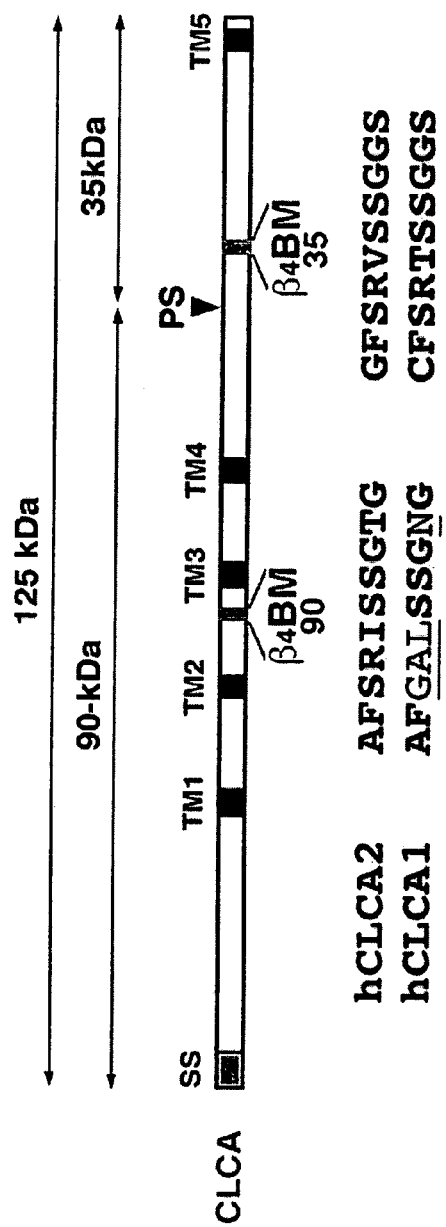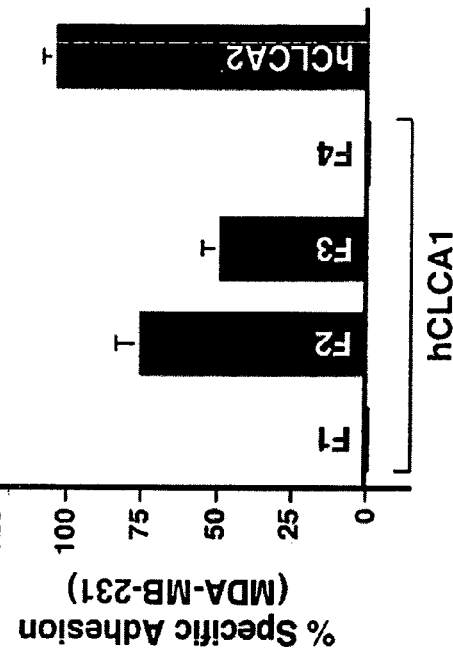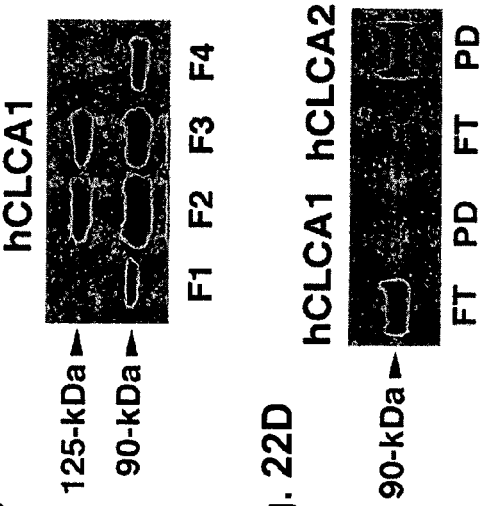
Fig. 22A
Fig. 22B
Fig. 22C
Fig. 22D

CALCIUM-ACTIVATED CHLORIDE CHANNEL PROTEINS AND THEIR USE IN ANTI-METASTATIC THERAPY

This application is a Continuation In Part of U.S. patent application Ser. No. 10/055,412 filed Oct. 29, 2001, now U.S. Pat. No. 6,692,939, which is a Divisional of U.S. patent application Ser. No. 09/193,562 filed on Nov. 17, 1998, now U.S. Pat. No. 6,309,857, which claims the priority of U.S. Provisional Application Ser. No. 60/065,922 filed on Nov. 17, 1997, the disclosures of which are incorporated herein by reference.

This invention was made with government support under grants CA 47668 from the National Cancer Institute. The government has certain rights in the invention.

FIELD OF THE INVENTION

The present invention relates to nucleotide sequences encoding a family of mammalian calcium activated chloride channels which may alternatively, or additionally function as adhesion molecules. More particularly, the invention is directed to genes isolated from bovine endothelial cells, human endothelial cells and murine endothelial cells, which encode calcium activated chloride channel molecules and include the lung-endothelial cell adhesion molecules and associated proteins.

BACKGROUND OF THE INVENTION

Calcium Activated Chloride Channels

Ion channels are not only required for normal cellular functions but also play a critical role in numerous diseased states. For example, cystic fibrosis results when ion transport in epithelial cells of individuals is altered due to a genetic defect of the cystic fibrosis transmembrane conductance regulator CFTR; Knowles et al., 1983, J. Clin. Invest. 71:1410-1417). Although serious airway pathology is usually the primary cause of mortality in young adults with CF, intestinal epithelial alterations have also been observed. However, the severity of tissue lesions does not correlate with the expression of CFTR in humans or mice, suggesting the involvement of cell-specific channels in addition to CFTR. Further support for the involvement of other channel protein molecules in CF comes from observations that calcium activated chloride secretion is preserved in respiratory epithelia of CF patients compared to unaffected individuals, but is significantly reduced or absent from CFTR-defective epithelia. These results strongly suggest that an alternative non-CFTR regulated chloride channel activity might account for attenuating CF disease in some tissues. Thus, a need exists for identification, isolation and functional analysis of alternative chloride channels.

Adhesion Molecules

It is apparent that endothelial cell adhesion molecules may have functions in addition to their adhesive functions. For example, integrins have transmembrane signaling capacities which may play a role in the adherence process. However, the primary function of endothelial cell adhesion molecules is adherence to a substrate such as (a) to promote adherence of endothelial cells to basement membrane, (b) to promote vascular arrest and to facilitate extravasation of leukocytes such as during an immune response, and (c) to promote homing of lymphocytes to a particular lymphoid tissue. Other molecules may play a role in controlling adherence of endothelial cells. For example, chloride ion channels are thought to be involved in a signaling cascade when lymphatic endothelial cells begin to adhere to a substrate (Martin et al., 1996, Microvasc. Res. 52:200-9).

There is considerable evidence that metastatic nonlymphoid tumor cells mimic leukocytes in recognizing and adhering to one or more endothelial cell adhesion molecules to migrate in blood vessels, to arrest in vascular areas of organs which may provide the microenvironment conducive for metastatic growth, and to extravasate into surrounding tissues. An example of such an endothelial cell adhesion molecule which promotes adhesion of tumor cells and mediates metastasis is lung-endothelial cell adhesion molecule (Lu-ECAM-1). Lu-ECAM-1 is a 90 kilodalton (kDa) integral membrane protein constitutively expressed primarily in endothelial cells of pleural and subpleural microvessels. Both in vitro studies and in vivo studies indicate that Lu-ECAM-1-expressing endothelial cells promote adhesion of certain lung-colonizing tumor cells in a manner that is consistent with the expression level of the adhesion molecule and the metastatic propensity of tumor cells. For example, in an in vitro tumor cell/endothelial cell adhesion assay, highly lung metastatic B1G-F10 melanoma cells bind to lung-matrix-modulated endothelial cells expressing Lu-ECAM-1 in significantly larger numbers than their intermediate or low lung-metastatic counterparts (B1G-L8-F1O and B1GFO, respectively; Zhu et al., 1991, Proc. Nati. Acad. Sd. USA 88:9568-720). Such binding appears to be calcium ($Ca^{2+}$) dependent. Further, anti-Lu-ECAM-1 monoclonal antibodies significantly inhibit adhesion of B1GF1O melanoma cells to Lu-ECAM-1 expressing endothelial cells in culture (Zhu et al., 1991, supra) Anti-Lu-ECAM-1 monoclonal antibodies are also efficient in preventing metastatic colonization of the lungs by highly lung-metastatic B1GF1O cells in a standard animal model for metastasis (Zhu et al., 1991, supra). Lu-ECAM-1, affinity purified from detergent extracts of bovine aortic endothelial cells, was used to immunize mice. The immunized mice showed an inhibition of metastatic colonization of the lungs by B1GF1O melanoma cells, the efficiency of which was dependent upon the anti-Lu-ECAM-1 serum titer (Zhu et al., 1992, J. Clin. Invest. 89:1718-1724). Lu-ECAM-1 appears to be the endothelial cell adhesion molecule for metastatic tumor cells that express the ligand/34 integrin subunit (and possibly other ligands) including, but not limited to, lung-metastatic breast tumor cells, and lung-metastatic melanoma tumor cells.

Anti-adhesion therapy may be used to interfere with adhesion between organ-specific endothelial cells and blood-borne cancer cells in preventing the formation of metastatic colony formation in organs that support metastatic cell growth. The amount of endothelial cell adhesion molecule that can be made from detergent extracts, as well as the rate of production of the endothelial cell adhesion molecule, is generally insufficient for cost-effective commercial production. More efficient production of proteins, with a concomitant reduction in production cost, can often be achieved by producing a protein through recombinant means. In that regard, in some cases a host cell may be genetically engineered such that an increased amount of the protein is produced and/or the protein is produced in a manner which facilitates its isolation (as compared to harvesting the protein from cell membranes).

SUMMARY OF THE INVENTION

It is an object of the invention to provide nucleotide sequences, isolated from mammalian endothelial cells, which encode molecules that functions as a calcium activated chloride channel-adhesion molecule (also referred to herein as "CACC-AM" or "CLCA").

It is also an object of the present invention to provide nucleotide sequences which are variants (including portions) of the gene comprising the CACC-AM, and which encode a polypeptide having substantially the biological activity as compared to the biological activity of the CACC-AM.

It is an object of the present invention to provide a means for recombinantly producing CACC-AM molecule.

It is an object of the present invention to provide a means for recombinantly producing proteins associated with CACC-AM molecule.

It is a further object of the present invention to provide expression vectors containing a nucleotide sequence that encodes a CACC-AM molecule; or containing a nucleotide sequence which is a variant of the gene for CACC-AM, and that encodes a polypeptide having substantial biological activity of a CACC-AM; or containing a nucleotide sequence that encodes a protein associated with a CACC-AM.

It is an additional object of the present invention to provide recombinant host cells which contain multiple copies of a nucleotide sequence that encodes a CACC-AM molecule, wherein the CACC-AM molecule is recombinantly produced by culturing the recombinant host cells under suitable conditions.

It is an additional object of the present invention to provide compositions and methods for inhibiting metastasis. It is another object of the present invention to provide compositions and methods for inhibiting the growth of metastatic tumors in mammals.

Other objects, features, and advantages of the present invention will become apparent from the following drawings and detailed description.

BRIEF DESCRIPTION OF THE DRAWINGS

FIG. 8 is a representation of biochemical analysis of the hCLCA2 protein for in vitro translation (a) and immunoblot detection of myc tagged hCLCA2 constructs in HEK293 cells (b)

FIG. 14 is a representation of a comparison of the amino acid sequences of the calcium activated chloride channels, hCLCA1 (SEQ ID NO:27); hCLCA2 (SEQ ID NO:31); bCLCA1 (SEQ ID NO:46); Lu-ECAM-1 (SEQ ID NO:1); and mCLCA1 (SEQ ID NO:33).

FIG. 15A is a graphical representation of the dissection of the 90-kDa protein of the CLCA prototype bCLCA2 (Lu-ECAM-1) into various GST fusion proteins (GST-HX, -HV, -HP, -NE, -VX, -PX, and -BX).

FIG. 15B is a representation of a Coomassie Blue-stained gel (SDS-PAGE) of GST-bCLCA2 fusion proteins synthesized by *E. coli*.

FIG. 15C is a representation of Western blots testing of the GST-bCLCA2 fusion proteins for binding to the adhesion-blocking anti-bCLCA2 mAb6D3 using immunoprecipitation and Western blotting with anti-GST polyclonal antibodies. Lane 1, immunoprecipitated GST-bCLCA2 fusion protein; lane 2, starting material: solubilized, purified GST-bCLCA2 fusion proteins. Notice that the shortest bCLCA2 fragment pulled down by mAb6D3 is GST-BX.

FIG. 15D is a graphical representation of results from testing of GST-bCLCA2 fusion proteins (BX, NE, NP, and PX) for adhesion to MDA-MB-231 cells. MDA-MB-231 cells strongly adhere to GST-PX and -BX but do not adhere to GST-NE and -HP. MDA-MB-231 cells also adhere to the 90-kDa and to the 35-kDa subunits of bCLCA2 and hCLCA2.

FIG. 16A depicts a PROTOMAT-identified conserved sequence motif in the 90- and 35-kDa processing products of hCLCA2 is compared with the corresponding sequences in mCLCA5, mCLCA1, and bCLCA1, all expressed by pulmonary endothelia (boxed motifs, principal test sequences; underlined motifs, not tested). Sequences as shown in FIG. 16A are: hCLCA2 90-kDa $\beta_4$BM (AFSRISSGTG), SEQ ID NO:50; hCLCA2 and mCLCA5 have the same 35-kDa $\beta_4$BM (GFSRVSSGGS), which is SEQ ID NO:51; the mCLCA5 90-kDa $\beta_4$BM (AFVRISSGTG) is SEQ ID NO:54; the mCLCA1 90-kDa $\beta_4$BM (AFSRISSTSG) is SEQ ID NO:55; the mCLCA1 35-kDa $\beta_4$BM (DFNRVTSGGS) is SEQ ID NO:56; the bCLCA2 90-kDa $\beta_4$BM (AFSRISSRSG) is SEQ ID NO:57; and the bCLCA2 35-kDa $\beta_4$BM (DFSRLTSGGS) is SEQ ID NO:58.

FIG. 16B is a graphical representation of GST-HA AFSRISSGTG (SEQ ID NO:50) (100 ng/ml) representing the $\beta_4$-binding motif of the 90-kDa hCLCA2 (termed $\beta_4BM_{hCLCA2(90)}$), which was generated and tested for adhesion to dishes coated with $\beta_4$ integrin, $\beta_1$ integrin, $\beta_3$ integrin, fibronectin, and BSA (10 μg/ml) using anti-GST antibody ELISA to detect bound $\beta_4BM_{hCLCA2(90)}$. Notice that $\beta_4BM_{hCLCA2(90)}$ bound only to $\beta_4$-coated dishes, p<0.01 relative to BSA.

FIG. 16C is a representation of Western blotting results from a pull-down (PD) assay of soluble $\beta_4$ but not $\beta_1$ and $\beta_3$ (remain in flow-through (FT)) with $\beta_4BM_{hCLCA2(90)}$ immobilized on glutathione beads. $\alpha$-$\beta_4$ pAbH101, $\alpha$-$\beta_1$ mAb (clone 18), and $\alpha$-$\beta_3$ mAb25E11 were used for Western blot detection.

FIG. 16D is a representation of Western blotting results from a PD of $\beta_4BM_{hCLCA2(90)}$ by immunobead-immobilized $\beta_4$ integrin but not by $\beta_1$ integrin. $\alpha$-GST pAb(B-14) was used for Western blot detection.

FIG. 18A is a graphical representation of results demonstrating binding of $\beta_4BM_{hCLCA2(90)}$ (100 ng/ml) to MDA-MB-231 analyzed by FACS. Notice that $\beta_4BM_{hCLCA2(90)}$ binds strongly to MDA-MB-231 (a) and generates a histogram similar to that recorded for anti-$\beta_4$ pAbH101 staining of MDA-MB-231 (b); the control polypeptide P14 does not bind.

FIG. 18B is a graphical representation of results demonstrating selective adhesion of MDA-MB-231 cells to $\beta_4BM_{hCLCA2(90)}$- and $\beta_4BM_{hCLCA2(35)}$-coated wells (10 μg/ml) (negative control: BSA and GST; positive control: poly-L-lysine (PLL)).

FIG. 18C is a graphical representation of results demonstrating inhibition of the MDA-MB-231 adhesion to hCLCA2 by $\beta_4BM_{hCLCA2(90)}$ and $\beta_4BM_{hCLCA2(35)}$ (both 100 ng/ml) but not by the control polypeptides P14 and PEDA. *, p<0.01 relative to MDA-MB-231 adhesion to hCLCA2.

FIG. 20A is a graphical representation of the CLCA-binding domain's location in the SDL of $\beta_4$ integrin. A, scheme of the $\beta_4$ integrin: 1-27, signal sequence; 111-343, putative I domain-like structure; 184-203, predicted loop region of $\beta_4$. Sequences of the loop regions of $\beta_4$(184-203) and $\beta_1$(197-219) are displayed (boxed). The β4 sequence is SEQ ID NO:60; the β1 sequence is SEQ ID NO:62; the E. Coli sequence is SEQ ID NO:63.

FIG. 20B is a graphical representation of results from an hCLCA2 binding assay. Myc-tagged hCLCA2 (3 μg/ml) is bound to uncoated wells (black column), GST-(gray column), GST-$\beta_1$(197-219)-(dashed column), or GST-$\beta_4$(184-203)-coated wells. Bound hCLCA2 is detected by anti-Myc antibody. hCLCA2 binds to GST-$\beta_4$(184-203)-coated wells as well as uncoated wells (positive control) but not to wells coated with GST-$\beta_1$(197-219) or GST.

FIG. 20C is a graphical representation of results from a pull-down assay. GST-$\beta_4$ and GST-$\beta_1$ fusion polypeptides are immobilized on glutathione beads and then tested for pull-down of hCLCA2 from lysates of transfected HEK-293 cells. Notice that only GST-$\beta_4$ is able to pull down hCLCA2.

FIG. 20D is a graphical representation of results demonstrating that GST-$\beta_4$ binds to GST-$\beta_4BM_{hCLCA2(90)}$. The wells of microtitration plates were coated with $\beta_4BM_{hCLCA2(90)}$ or control polypeptide PEDA (10 μg/ml each) and tested for binding of biotinylated GST-$\beta_4$ (30 μg/ml) by ELISA.

FIG. 20E is a representation of a Western blot demonstrating that chimeric $\beta_{4-1-4}$ fails to bind hCLCA2. $\beta_{4-1-4}$ was generated as described in Example 11 and transfected together with $\alpha_6$ into HEK293 cells (positive control: $\beta_4$+$\alpha_6$; negative control: $\alpha_6$). Lysates from transfected HEK293 cells were incubated with anti-$\beta_4$ pAbH101-conjugated protein G beads (overnight at 4° C.). Beads were then washed and incubated with immunopurified Myc-tagged hCLCA2. Bound material was detected by Western blotting using anti-Myc mAb 9E10. WB, Western blot.

FIGS. 21A-21E are graphical representations of results from adhesion assays demonstrating inhibition of the $\beta_4$/CLCA adhesion with a $\beta_4$ SDL polypeptide. Wells of microtitration plates were coated with substrate (hCLCA2 (FIG. 21A), mCLCA1 (FIG. 21D), EHS laminin (FIG. 21C and FIG. 21E), or placental laminin (FIG. 21B)) overnight at 4° C. at the indicated concentration, then seeded with MDA-MB-231 (FIG. 21A, FIG. 21B, and FIG. 21C) or 4T1 (FIG. 21D and FIG. 21E) breast cancer cells, and incubated for 20 min at 37° C. No effect was recorded for the binding to placental and EHS laminins. *,p<0.01 relative to adhesion to substrate alone.

FIG. 22A is a graphical representation of a CLCA molecule. CLCA molecules (125 kDa) are normally cleaved into 90- and 35-kDa polypeptides. The proteolytic processing site is indicated by an arrowhead and marked PS. TM1-5 denote transmembrane domains, and SS denotes the signal sequence. Putative $\beta_4$ integrin-binding domains in the 90- and the 35-kDa cleavage products are marked $\beta_4$BM. The hCLCA2 domain SEQ ID NO:s are as described in FIG. 16A. The hCLCA1 sequences shown are the hCLCA1 90-kDa $\beta_4$BM (AFGALSSGNG) which is SEQ ID NO:59 and the hCLCA1 35-kDa $\beta_4$BM (CFSRTSSGGS) which is SEQ ID NO:52.

FIG. 22B is a representation of gels showing the purified Myc-tagged hCLCA1 by α-Myc immunoaffinity chromatography. Four fractions (F1-F4) were collected from the column. Fraction 1 and fraction 4 show presence of the 90-kDa subunit only, while fraction 2 and fraction 3 show presence of both the 125-and 90-kDa proteins (α-Myc Western blot).

FIG. 22C 22A is a graphical representation of results demonstrating adhesion of MDA-MB-231 to fractions 1-4 revealed that tumor cells were unable to adhere to fraction 1 and fraction 4 but adhered well to fractions 2 and 3, likely through the preserved $β_4$BM in the 35-kDa sequence of unprocessed hCLCA1.

FIG. 22D is a graphical representation of results from a pull-down assay demonstrating that the 90-kDa fragment of hCLCA1 and hCLCA2 with glutathione bead-immobilized GST-$β_4$(184-203). hCLCA2, but not hCLCA1, is pulled down by GST-$β_4$ (α-Myc Western blot). PD, pull-down; FL, flow-through.

DETAILED DESCRIPTION OF THE INVENTION

Definitions

Figure 1:
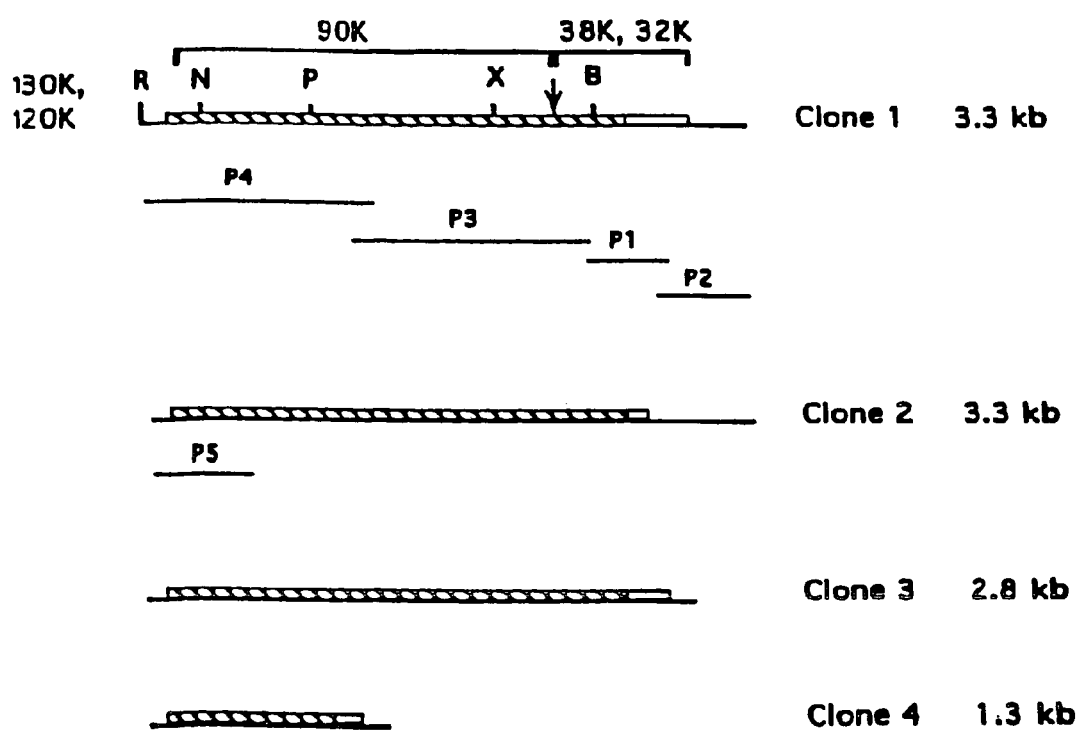
FIG. 1 is a schematic diagram of a method for identifying clones using polymerase chain reaction. Also shown are restriction enzyme sites EcoRI ("R"); NdeI ("N"), PstI ("P"), and BglII ("B").

"Precursor" is a term used in conjunction with "lung-endothelial cell adhesion molecule" hereinafter for the purposes of the specification and claims to refer to a sequence of amino acids bound to and located upstream from the N-terminal portion of the mature form of a lung-endothelial cell adhesion molecule, wherein the removal of this sequence results in the formation of the "mature form" of the lung-endothelial cell adhesion molecule. A precursor protein is a form of a lung-endothelial cell containing a prepro-region. The prepro-region is made up of amino acids comprising a signal sequence, wherein the signal sequence is cleaved to form the mature form of a lung-endothelial cell adhesion molecule.

"Calcium activated chloride channel-adhesion molecule" or "CACC-AM" "or CLCA" is a term used hereinafter for the purposes of the specification and claims to mean a molecule isolated from mammalian endothelial cells that when expressed in cells induces the expression of calcium activated chloride conductance channels.

"Calcium activated chloride channel (s)" is a term used for the purposes of the specification and claims to mean chloride channels whose conductance is activated by calcium as judged by inhibition of conductance by DIDS, DTT or niflumic acid.

"Recombinant calcium activated chloride channel-adhesion molecule" or "Recombinant CACC-AM" is a term used hereinafter for the purposes of the specification and claims to refer to a CACC-AM molecule produced from a heterologous cell (e.g., other than from vascular endothelial cells), wherein the heterologous cell has been genetically engineered to contain a nucleotide sequence that encodes a CACC-AM molecule.

"Recombinant calcium activated chloride channel-adhesion molecule-associated protein" or "recombinant CACC-AM-associated molecule" is a term used hereinafter for the purposes of the specification and claims to refer to a CACC-AM associated protein produced from a heterologous cell (e.g., other than from vascular endothelial cells) wherein the heterologous cell has been genetically engineered to contain a nucleotide sequence that encodes a CACC-AM associated molecule. "Lung-endothelial cell adhesion molecule-associated protein" is a term used hereinafter for the purposes of the specification and claims to refer to a protein which (a) is smaller in kilodaltons than the mature form of the lung-endothelial cell adhesion molecule, as determined by, for example, sodium dodecyl polyacrylamide gel electrophoresis (SDS-PAGE) or amino acid analysis; (b) is encoded by messages that also encode the lung-endothelial cell adhesion molecule; (c) is antigenically distinct from the lung-endothelial cell adhesion molecule; and (d) is extracellularly associated in a complex (e.g, specific binding) with the lung-endothelial cell adhesion molecule.

By the term "operably linked" is meant, for the purposes of the specification and claims to refer to the chemical fusion (restriction with subsequent ligation) or synthesis of heterologous DNA with a nucleotide sequence that encodes a lung-endothelial cell adhesion molecule or a lung-endothelial cell adhesion molecule-associated protein such that the resultant recombinant DNA molecule is formed in a proper orientation and reading frame for the nucleotide sequence to be transcribed into functional RNA. In the construction of the recombinant DNA molecule, it is generally preferred to position a promoter at a distance upstream from the initial codon of the nucleotide sequence that is approximately the same as the distance in its natural setting (e.g., in an endothelial cell). However, as known in the art, some variation in the distance can be accommodated without loss of promoter function. Likewise, it is generally preferred to position an enhancer element at a distance upstream from the promoter, or incorporated into the promoter sequences as a promoter element, or located between the promoter and the DNA molecule to be expressed. However, as known in the art, some variation in the placement can be accommodated without loss of the enhancer element's function. "Expression control sequences" is meant, for the purposes of the specification and claims to refer to a promoter or promoter-enhancer combination.

By the term "expression vector" is meant, for the purposes of the specification and claims to refer to a DNA molecule which is operably linked to a nucleotide sequence that encodes one or more recombinant proteins comprising a lung-endothelial cell adhesion molecule and/or a lung-endothelial cell adhesion molecule-associated protein such that the production of the recombinant protein is effected in a suitable host. The vector may include, but is not limited to, a plasmid, phage, or a potential genomic insert.

By the terms "degeneracy substitutions", for the purposes of the specification and claims to refer to the base pair changes (substitutions) in the nucleotide sequence such as a change in one or more bases of a triplet codon (e.g., third base degeneracy) resulting in the encoding of the same amino acid as before the change, or a change resulting in the encoding of a conservative substitution in the amino acid sequence encoded. With respect to such variations, and as appreciated by those skilled in the art, because of third base degeneracy, almost every amino acid can be represented by more than one triplet codon in a coding nucleotide sequence. Thus, in nature or by mutagenic means, the nucleotide sequence be modified slightly in sequence (e.g., substitution of a nucleotide in a triplet codon), and yet still encode its respective gene product of the same amino acid sequence as encoded by the disclosed nucleotide sequences.

Further, the nucleotide sequence may have minor base pair changes which may result in variation (conservative substitution) in the amino acid sequence encoded. Such conservative substitutions are not expected to substantially alter the biological activity of the gene product. A "conservative substitution" for the purpose of the specification and claims means modification of one or more amino acids are such that the tertiary configuration of the recombinant protein is substantially unchanged. Conservative substitutions is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. It is noted that a nucleotide sequence according to the present invention encodes a mammalian Lu-ECAM-1 as to be described more fully herein, and does not encompass the nucleotide sequence encoding the bovine tracheal epithelial chloride channel described recently (Cunningham et al., 1995, J. Biol. Chem. 270:31016-26).

By the terms "% identity of amino acid sequence" are meant, for the purposes of the specification and claims to refer to the percent of amino acid positions that are identical between two amino acid sequences as determined by sequence comparisons performed using algorithms known to those skilled in the art.

By the terms "% identity of nucleotide sequence" are meant, for the purposes of the specification and claims to refer to the percent of nucleotide base pair positions that are identical between two nucleotide sequences as determined by sequence comparisons performed using algorithms known to those skilled in the art.

By the term "substantially" is used in conjunction with the biological activity (e.g., adhesive function or chloride ion channel function) to mean, for the purposes of the specification and claims, to refer to retaining a degree of the biological activity ranging from approximately 50% of the activity to greater than 100% of the activity, in relation to the molecule with which it is compared.

By the term "unexpectedly improved" is used in conjunction with the biological activity (e.g., adhesive function or chloride ion channel function) of a recombinant protein to mean, for the purposes of the specification and claims, to refer to a degree of the biological activity which is approximately greater or equal to 30% more biological activity than that of the molecule to which it is compared, and which improvement in activity was unforeseen for this recombinant protein.

The present invention relates to nucleotide sequences and variants thereof that encode a polypeptide which is a calcium activated chloride channel and/or has adhesion properties. In accordance with this invention, nucleotide sequences encoding Lu-ECAM-1/mouse calcium activated chloride channel (mCLCA), and human calcium activated chloride channel molecules (hCLCA1, hCLCA2, and hCLCA3) are disclosed. The nucleotide sequences have been derived from bovine aortic endothelial cells, from murine aortic endothelial cells, or from human endothelial cells. In one embodiment, a nucleotide sequence of the present invention, SEQ ID NO:1, contains sequences that encode either Lu-ECAM-1 or Lu-ECAM-1-associated protein. From SEQ ID NO:1, the lung-endothelial cell adhesion molecule precursor is deduced to be approximately 905 amino acids (SEQ ID NO:2). Cleavage of the signal peptide (amino acids −21 to −1 of SEQ ID NO:2) from the lung-endothelial cell adhesion molecule precursor, and subsequent post-translational processing, results in a Lu-ECAM-1 of about 799 amino acids (amino acid 1 to amino acid 799 of SEQ ID NO:2) and with a predicted molecular size of approximately 87 kDa. It was also discovered during the development of the invention that a SEQ ID NO:1 encodes a Lu-ECAM-1-associated protein (SEQ ID NO:3) which, depending on the glycosylation pattern, has an apparent molecular size (e.g., as determined by SDS-PAGE) ranging from about 22 kDa (little or no glycosylation present) to 38 kDa. More particularly, SEQ ID NO:1 encodes Lu-ECAM-1-associated proteins of apparent molecular size of about 38 kDa and of about 32 kDa. Further, these two LU-ECAM-1-associated proteins bind with Lu-ECAM-1 (amino acid 1 to amino acid 799 of SEQ ID NO:2)in forming Lu-ECAM-1 complex. The mCLCA, human CLCA1, and human CLCA2 were then cloned and sequenced using the Lu-ECAM-1 open reading frame as a probe.

When compared with the amino acid sequences of previously cloned homologs, hCLCA2 shares a consensus site for monobasic proteolytic cleavage following arginine residue 674 in SEQ ID NO:32. Cleavage at this putative site results in two proteins having amino acids 1-674 and 675-943 of the hCLCA2 full length sequence, which is consistent with the sizes of the 90 kDa and 35 kDa subunits, respectively. (Fuller et al., (2001) Pfluegers Arch. 443, Sippl. 1, S107-S110). A similar putative cleavage site is observed in hCLCA2 at an arginine at position 670 in SEQ ID NO:28 which results in the 90 kDa and 35 kDA hCLCA1 subunits.

In accordance with another embodiment of this invention, using recombinant techniques a nucleic acid molecule containing the nucleotide sequence encoding calcium activated chloride channel-adhesion molecule is incorporated into an expression vector. The recombinant vector is introduced into an appropriate host cell thereby directing the expression of the sequence in that particular host cell. The expression system, comprising the recombinant vector introduced into the host cell, can be used to produce recombinant CACC-AM, or associated proteins. According to the present invention, recombinant CACC-AM, a recombinant polypeptide having CACC-AM activity, and/or recombinant CACC-AM associated protein, can be purified by methods known in the art including ion-exchange chromatography, affinity chromatography, or other chromatographic separation techniques.

Another embodiment of the present invention is a method for providing calcium-activated chloride conductance channels to mammalian cells. In mammalian cells in which the membrane chloride ion channels are deficient in number or function (e.g., in airway epithelial cells of cystic fibrosis patients), a method of providing to mammalian cells a calcium-activated chloride conductance channel, comprising CACC-AM or a polypeptide having CACC-AM activity, comprises administering directly to the cells an expression vector. The expression vector contains a nucleic acid molecule operably linked to expression control sequences, wherein the nucleic acid molecule encodes a CACC-AM, with the resultant expression vector being introduced into the mammalian cell, and the calcium-dependent chloride conductance produced in the mammalian cells containing the expression vector.

The bovine Lu-ECAM-1 complex appears to be expressed in lung, spleen, and aortic epithelial cells. The murine Lu-ECAM-1 complex appears to be expressed in lung, trachea, spleen, mammary gland, intestine, uterus, epididymis, testis, pancreas, kidney, liver and skin. A first human CLCA1 (hCLCA1) molecule (SEQ ID NO:28) appears to be expressed in small intestine, and colon mucosa. A second human CLCA2 (hCLCA2) molecule (SEQ ID NO:32) appears to be expressed in trachea and mammary gland. A third human CLCA3 (hCLCA3) molecule (SEQ ID NO:30) appears to be expressed in small intestine, trachea, mammary gland, stomach, bone marrow, spleen, lymph node, and peripheral blood leukocytes. That these various mammalian proteins appear to be expressed in tissues which are affected in cystic fibrosis may allow them to be used as chloride channels in accordance with Example 8 herein.

In another embodiment of the invention, a CLCA β4 binding consensus sequence (SEQ ID NO:61) is disclosed. The CLCA β4 binding consensus sequence consists of six amino acids in the order Phe(Ser/Asn)Arg(Ile/Leu/Val)(Ser/Thr)Ser. Peptides comprising the consensus sequence bind to β4 integrin and inhibit adhesion and tumor colony formation of rmetastatic cancer cells. Further, the β4 binding domains of the 90 kDa hCLCA2 (SEQ ID NO:50), the 35 kDa hCLCA2 (SEQ ID NO:51) and the hCLCA1 35 kDa (SEQ ID NO:52) are also disclosed. Like the CLCA β4 binding consensus sequence, the hCLCA2 90 kDa, 35 kDa and hCLCA1 35 kDa β4 binding sequences inhibit adhesion and tumor colony formation by metastatic cancer cells.

In yet another embodiment, the present invention provides a method of inhibiting the formation of tumors in an individual. The method comprises the step of administering to an individual a polypeptide comprising the CLCA β4 binding consensus sequence (SEQ ID NO:61). For example, the method of the present invention is useful for administrating the compositions of the present invention to individuals including, but not limited to, individuals who are at risk of developing lung cancer or who have been diagnosed with lung cancer. Methods of administering polypeptides to an individual are well known to those skilled in the art, as are pharmacologically acceptable excipients with which the polypeptides may be combined.

For purposes of the description, the following embodiments illustrate the manner and process of making and using the invention and set forth the best mode contemplated by the inventor for carrying out the invention, but are not to be construed as limiting.

EXAMPLE 1

This embodiment illustrates the molecular cloning of calcium activated chloride channel-adhesion molecules. Lu-ECAM-1. A nucleic acid molecule encoding Lu-ECAM-1 and Lu-ECAM-1-associated proteins according to the present invention can be obtained by preparing cDNA from total RNA isolated from a host cell expressing Lu-ECAM-1. To illustrate this example, total RNA was isolated from bovine aortic endothelial cells by the guanidinium chloride procedure, and a Lu-ECAM-1 CDNA clone was constructed using nucleic acid amplification as summarized in FIG. 1. First, the N-terminal and internal amino acid sequences of a 38 kDa Lu-ECAM-1-associated protein (SEQ ID NO:3) were used to design degenerate primers for primary and nested polymerase chain reactions using the reverse-transcribed total RNA as template.

Upstream primers corresponded to nucleotide sequences encoding amino acids 685 to 693, and amino acids 698 to 705, of SEQ ID NO:3. Downstream antisense primers corresponded to nucleotide sequences encoding amino acids 839 to 832, and amino acids 852 to 846, of SEQ ID NO:3. A product of approximately 450 bp was amplified (illustrated in FIG. 1 as "P1"). From these sequences, nondegenerate primers (SEQ ID NOs: 4 and 5) were designed, and the resultant amplification for 3' sequences resulted in a product of approximately 750 bp (FIG. 1, "P2"). Nondegenerate primers (SEQ ID NOs: 6 and 7) were designed, and the resultant amplification for 5' sequences resulted in a product of approximately 1000 bp (FIG. 1, "P3"). To obtain the remaining 5' sequences (FIG. 1, "24") including a signal sequence and the ATG initiation codon, used was an internal primer (SEQ ID NO:8). To reconstitute the CDNA sequence from the amplified products (Pi-P4), the overlapping products were assembled into one open reading frame by an over-lap extension strategy using a high fidelity polymerase combination. The result was clone 1 (FIG. 1) comprising 3.3 kb and encoding the amino acid sequence of SEQ ID NO:2. Hydrophilicity analysis revealed six significant generally nonpolar regions. In particular, a hydrophobic sequence from amino acid 595 to amino acid 618 appears to be a transmembrane domain. Nine potential sites exist for asparagine-linked glycosylation.

Using the primers to probe a lambda cDNA library, three additional clones (clones 2, 3, and 4; FIG. 1) were identified and sequenced. Additional primers (SEQ ID NOs: 9 and 10) were used to obtain the 5' end sequences. Clone 2, a 3.3 kb variant of clone 1, was identical to clone 1 from nucleotide 252 to nucleotide 2438 of SEQ ID NO:1, but then the sequence diverged. The amino acid sequence deduced from clone 2 (SEQ ID NO:11) was identical to that of clone 1 up to amino acid 772 (of SEQ ID NO:2) followed by a glutamate and serine. Clone 3 was 2.8 kb variant of clone 1. The amino acid sequence deduced from clone 3 (SEQ ID NO:12) was identical to that of clone 1 up to amino acid 772 (of SEQ ID NO:2), followed by an additional 28 amino acids. Clone 4, of 1.3 kb, appears to encode a truncated 321 amino acid (SEQ ID NO:13) variant of Lu-ECAM-1 that may be secreted, and is identical in sequence to amino acids 1 to 303 of SEQ ID NO:2, followed by 18 divergent amino acids. An oligonucleotide probe (SEQ ID NO:14) synthesized from the unique 3' region of clone 1 was used to hybridize MRNA isolated from bovine aortic endothelial cells. The probe detected high molecular weight bands (6-10 kb) in Northern blot analysis as well as the 3.3 kb band. However, the probe did not hybridize to the 2.8 and 1.3 kb bands. These results indicate that the 38 kDa and 32 kDa proteins appear to be encoded only by the messages that also encode the 90 kDa protein.

This embodiment also illustrates that CACC-AM is conserved in mammalian species, and thus may serve the same or similar functions in mammalian species other than the ones disclosed herein. Conservation of the gene encoding CACC-AM was determined by multispecies genomic DNA (from human, green monkey, rat, mouse, dog, bovine, rabbit, chicken, and budding yeast) blot with probes derived from various regions of the bovine cDNA sequence for Lu-ECAM-1. These probes hybridized to all mammalian species genomic DNA, although the hybridization to rat DNA was comparatively weak. No hybridization signal was detected for chicken DNA or yeast DNA. These results indicate that the gene(or variant sequence thereof) encoding Lu-ECAM-1 is highly conserved in mammalian evolution.

Accordingly, using similar methods and primer sequences for isolating and sequencing of a nucleotide sequence encoding a bovine Lu-ECAM-1, various nucleotide sequences encoding other CACC-AMs maybe identified.

Mouse Calcium Activated Chloride Channel

As an illustration, a murine CACC/AM has been identified. A mouse lung cDNA library in lambda-gtll was screened with the open reading frame of Lu-ECAM-1 cDNA (EcoR1-Bg1II 2.4 kb fragment of the Lu-ECAM-1 cDNA) using low stringency hybridization conditions (hybridization at 65 C in 5×SSC, 5× Denhardt's solution and 0.2% SDS solution overnight with agitation; washing with 2×SSC followed by several washes in 0.2×SSC, 0.2% SDS at room temperature for a total of 30 minutes). Positive phages were purified and analyzed by Southern blot hybridization techniques. Standard sequencing techniques (eg. automatic sequencing techniques) were used to determine the sequence of the clones. The largest of the isolated cDNA was 2.2 kb in length. It lacked the 5' end as determined by sequence comparison with the known bovine homolog. A fiull length mouse Lu-ECAM-1 was constructed by amplification of the 5' cDNA ends from a pool of mouse lung poly(A)+RNA (CLONTECH). A gene-specific primer (SEQ ID NO:35) was used to reverse transcribe the cDNA from mouse lung mRNA. A nested primer (SEQ ID NO:36) and a primer recognizing the 5' terminal tag were used to amplify the 5' end of the cDNA by polymerase chain reaction. PCR products were cloned into an expression vector(pGEM-3; Promega). A full length mouse mCLCA1 was assembled by fusing the rapid amplification product clone with the 2.2 cDNA insert in an expression vector (pm1I site of pBluescript, Stratagene). Thus a 3.02 kb long sequence (SEQ ID NO:33) encoding a polypeptide of 902 amino acids (SEQ ID NO:34) was obtained.

Human CLCA1

In another illustration, a nucleic acid molecule encoding human calcium sensitive chloride channels was obtained from either the genomic library or a cDNA library. A human genomic library was screened with the ORE of bovine Lu-ECAM-1 as probe using standard plaque hybridization techniques. Three positive clones of 4,6, and 7 kb were isolated and sequenced, spanning a contiguous genomic fragment of 14 kb with interspersed segments of 58 to 65% nucleotide identity to parts of the Lu-ECAM-1 ORE. Since the regions of homology did not encode a contiguous open reading frame and did not cover the entire Lu-ECAM-1 ORF the remaining parts of the gene were obtained by genomic walking using nested PCR primers from each 5' and 3' end of the clones obtained by plaque hybridizations. Nested PCR conditions were 20 cycles for the first amplification step and 30 cycles for the second amplification with annealing temperatures of approximately 2° below the calculated melting point of the primers and extension times of 5 mm per cycle. PCR products were cloned into a vector (pGem-T, Promega) and sequenced. The full length gene was isolated and sequenced spanning 31,902 bp. The reading frame of the genomic sequence was determined according to its sequence homology with bCLCA1, Lu-ECAM-1 and mCLCA1.

Using an RT-PCR based strategy, the CLCA1 cDNA was cloned and sequenced from small intestinal mRiNA. PCR primers (downstream primer SEQ ID NO:37, and upstream primer SEQ ID NO:38) flanking the ORE and containing linkers with NotI restriction sites were generated and used to amplify the 2745 bp ORF. RT-PCR was performed with 500 ng of human small intestinal poly(A+) (CLONTECH). Reverse transcription was carried out at 48° C. with Superscript RNase H-reverse transcriptase and PCR was performed with Pwo DNA polymerase (Boehringer). PCR conditions were as follows: initial denaturation at 94° C. for 3 min followed by addition of DNA polyrmerase; 35 cycles of 94° C. for 50 s, 58° C. for 30 s, and 72° C. for 2 min with a time increment of 3 s per cycle for each extension step, followed by-a final extension step of 72° C. for 8 min. Foe obtaining the untranslated region of CLCA1 mRNA, amplification of the 5' and 3' ends was carried out using primers SEQ ID NO:39 and SEQ ID NO:40 respectively. The resulting cDNA sequence (SEQ ID NO:27) comprises 3007 bp and is identical to the genomic fragments with high sequence similarity to the previously cloned homolog. It contains a single ORF of 2745 bp encoding a polypeptide of 914 amino acids (SEQ ID NO:28).

hCLCA2 cDNA

A human lung cDNA library (Clontech) was screened using Lu-ECAM-1 cDNA as probe as described above. Missing 5' and 3' ends of the isolated cDNA species were completed using RACE (Life Technologies). A single 3.6 kb cDNA species was identified and termed CLCA2. A sequence of 2970 bp is shown in SEQ ID NO: 31. The open reading frame of The nucleotide sequence encoding a polypeptide of 943 amino acids (SEQ ID NO:32) shared high degrees of identity with those of Lu-ECAM-1 (86%), bCLCA1 (85%), mCLCAl (76%), and hCLCA1 (63%)—FIG. 14.

hCLCA3 cDNA

A human spleen cDNA library packed in phage λgtll (Clontech)was screened using standard plaque hybridization protocols. The open reading frame (ORF) of the Lu-ECAM-1 cDNA was used as probe as described above. Phage colony blots were hybridized and washed at low stringency conditions (hybridization: 55° C. overnight in 4×SSC standard hybridization buffer without formamide; two stringency washes with 2×SSC, 0.1% SDS at room temperature, and two washes with 1×SSC, 0.1% SDS at 40° C.). After exhaustive screening of the library (>7×10$^6$ plaques), a single positive phage clone was plaque-purified, amplified, and subjected to DNA purification (Wizard Lambda Preps, Promega). The insert was cut out using the EcoRI sites and cloned into pBluescript II SK (Stratagene). Automated sequencing with initial plasmid-derived primers followed by internal gene-specific primers was performed by the Cornell University DNA Sequencing Facility using dRhodamine Terminator Cycle Sequencing on an ABI Prism 377 DNA Sequencer (PE Applied Biosystems). Missing 5' and 3' ends of the cDNA were isolated using the rapid amplification of cDNA ends (RACE) technique (Life Technologies) and human spleen poly-A+RNA (Clontech) as template.

The primers for amplification of 5' end were SEQ ID NO:43 and SEQ ID NO:44, and the primers for 3' end was SEQ ID NO:45. The resulting cDNA sequence of 3599 base paris (deposited in GenBank under accession no. AF043976) was obtained. A sequence of 3418 bp is shown in SEQ ID NO:29, which encodes for a polypeptide of 1000 amino acids (SEQ ID NO:30).

EXAMPLE 2

This example illustrates the proteins encoded by the cDNAs isolated in Example 1 and the relationship between CACC-AM and associated proteins. As an illustration, the relationship is between Lu-ECAM-1 and Lu-ECAM-1 associated protein is demonstrated. Antigenic characterization was performed by generating anti-Lu-ECAM-1 antibodies, and testing the antibodies in Western blot analyses of bovine aortic endothelial cell extracts. Rats were immunized with either the 90 kDa band excised from a polyacrylamide gel and mixed with adjuvant, resulting in polyclonal antibody R4; or a 38 kDa band excised from a polyacrylamide gel and mixed with adjuvant, resulting in polyclonal antibody R41. Two peptides (SEQ ID NOs: 15 and 16) were synthesized, conjugated to KLH, and used to immunize rabbits in forming polyclonal antibodies CU11 and CU8, respectively. Monoclonal antibody 6D3 has binding specificity to Lu-ECAM-1 as described previously (Zhu et al., 1992, supra).

Figure 2A:
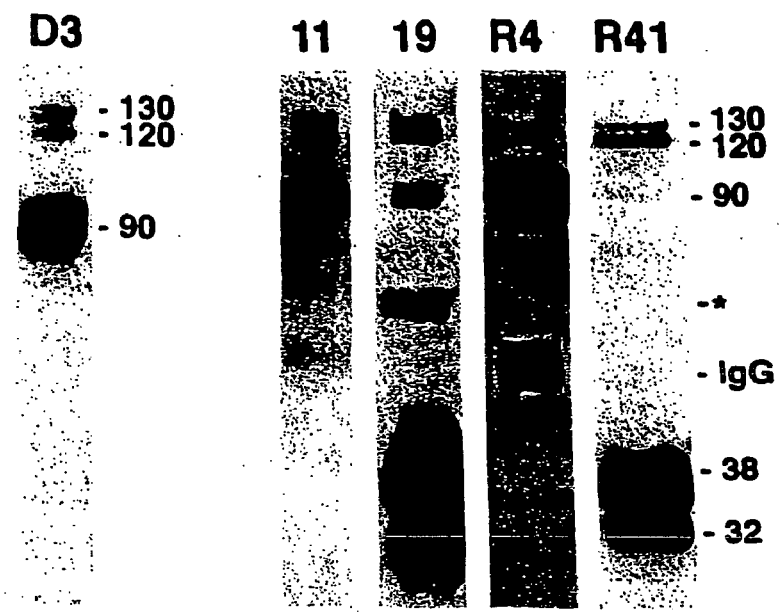
FIG. 2A is a representation of immunoblots of bovine aortic endothelial cell proteins using either monoclonal antibody D3 ("D3"), polyclonal antibody CU11 ("11"), polyclonal antibody CU19 ("19"), polyclonal antibody R4 ("R4"), and polyclonal antibody R41 ("R41").
Figure 2B:
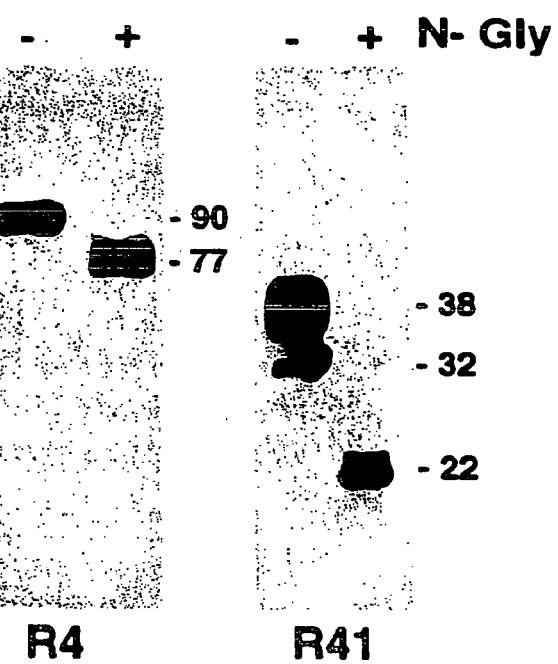
FIG. 2B is a representation of Lu-ECAM-1 untreated ("−")or Lu-ECAM-1 treated with N-glycosidase F ("+") followed by immunoblot analysis using polyclonal antibody R4; and Lu-ECAM-1-associated proteins untreated ("−") or Lu-ECAM-1-associated proteins treated with N-glycosidase F ("+") followed by immunoblot analysis using polyclonal antibody R41.

As shown in FIG. 2A, mAb 6D3 detected a 90 kDa component (Lu-ECAM-1) and two larger bands of approximately 120 kDa and 130 kDa (Lu-ECAM-1 precursors); but not the 38 kDa or the 32 kDa components (Lu-ECAM-1-associated proteins). Likewise, polyclonal antibody (against amino acid residues of SEQ ID NO:15)recognized only the 90 kDa, 120 kDa, and 130 kDa components(FIG. 2A). In contrast, polyclonal antibody CU19 (against amino acid residues 618 to 767 of SEQ ID NO:2) strongly detected the 38 kDa and 32 kDa components, and the 120 kDa and 130 kDa components, but only weakly detected the 90 kDa component. These results are evidence that the initial translation products of the open reading frame in SEQ ID NO:1 are the 120 kDa and 130 kDa components, which are then processed to yield the 90 kDa, 38 kDa, and 32 kDa components.

These results were confirmed with polyclonal antibodies R4 and R41. R4, a polyclonal anti-90 kDa protein antibody, detected the 90 kDa band, as well as the 120 kDa and 130 kDa components; but not the 38 kDa, and 32 kDa components (FIG. 2A). R41, a polyclonal anti-38 kDa protein antibody, detected the 38 kDa and 32 kDa bands, as well as the 120 kDa and 130 kDa components; but not the 90 kDa component (FIG. 2A). These results indicate that (a) the 38 kDa and 32 kDa bands are antigenically related; (b) the 120 kDa and 130 kDa bands are antigenically related; and (c) the 120 kDa and 130 kDa bands have sequence in common with both the 90 kDa protein, and the 38 kDa and 32 kDa proteins. Treatment of Lu-ECAM-1 complex with Nglycosidase F reduced the 38 kDa and 32 kDa components to a common band of about 22 kDa, indicating the these two proteins represent alternate glycoforms (FIG. 23). N-glycosidase F treatment reduced the 90 kDa protein to 77 kDa (FIG. 23). The 77 kDa and 22 kDa products would add up to the exact size of the initial translation product of clone 1 before processing.

Figure 3A:
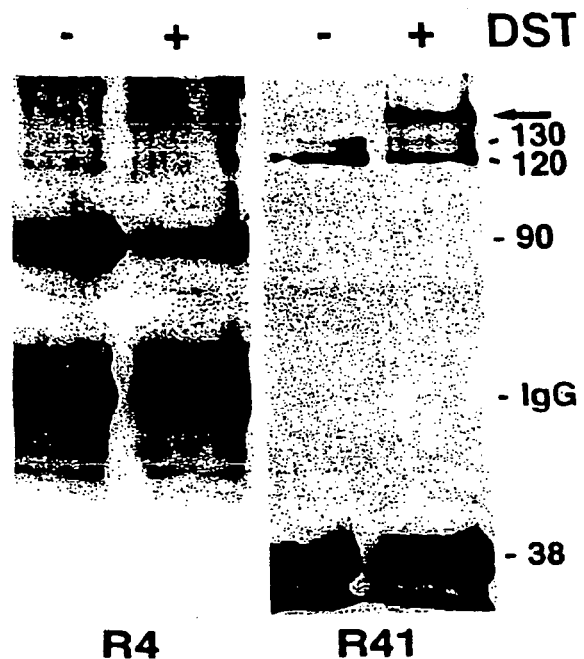
FIG. 3A is a representation of bovine aortic endothelial cells either untreated ("−") or treated with a crosslinker ("+") followed by immunoblot analysis using either polyclonal antibody R4 ("R4"), or polyclonal antibody R41 ("R41").
Figure 3B:
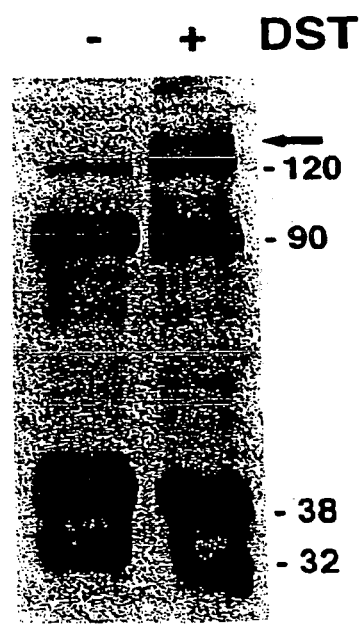
FIG. 3B is a representation of bovine aortic endothelial cells which were surface-biotinylated in the absence of ("−") or presence of ("+") a crosslinker followed by detection with streptavidin-horseradish peroxidase.

As shown in FIG. 2A, the 38 kpa and the 32 kDa components of the Lu-ECAM-1 complex are not recognized by mAb 6D3 in SDS-PAGE and Western blot analysis, suggesting that these components are likely noncovalently complexed with the 90 kDa protein. The Lu-ECAM-1 complex is resistant to dissociation by high salt, detergent, and EDTA, but readily dissociates when boiled in SDS in the presence or absence of reducing agents (e.g., dithiothrietol). To visualize the Lu-ECAM-1 complex, and to determine whether the proteins of the complex are associated intracellulary or extracellularly, the surface of bovine aortic endothelial cells was cross-linked. Confluent bovine aortic endothelial cells were surface biotinylated in the presence or absence of disuccinimidyl tartarate (DST), a reagent that restricts cross-linking to extracellular moieties of proteins in close contact. DST dissolved in dimethyl sulf oxide was added to the cells in a final concentration of 1 mM. Cross-linking was carried out at 4° C. with gentle shaking. The reactions were stopped by adding glycine to a final concentration of 50 mM. After quenching for 5 minutes, the cells were lysed for 1 hour in lysis buffer. Lysates were clarified by centrifugation, precipitated with mouse-IgG agarose beads, then immunoprecipitated with mAb 6D3. Immunoprecipitated proteins were analyzed by SDS-PAGE, transferred to nitrocellulose, and detected using avidin-horseradish peroxidase and chemiluminescence. As shown in FIG. 3A, immunoblots using either R4 (polyclonal anti-90 kDa protein antibody) or R41 (polyclonal anti-38 kDa protein antibody) detected a novel band migrating at approximately 140 kDa (arrow, FIG. 3A), with a concomitant reduction in intensities of the 90 kDa, 38 kDa, and 32 kDa components. As illustrated in FIG. 32, all Lu-ECAM-1 complex components were biotinylated on bovine aortic endothelial cell surface. These results suggest that the Lu-ECAM complex is made up of either the 90 kDa and 38 kDa proteins complexed in an extracellular association, and/or the 90 kDa and 32 kDa proteins complexed in an extracellular association.

Figure 6:
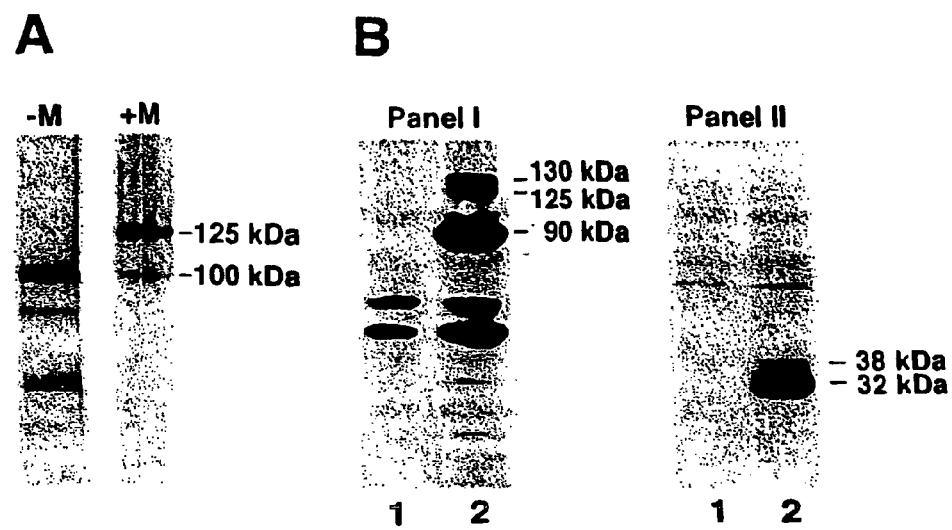
FIG. 6 is a representation of the expression of mCLCA1 by in vitro translation (A) and in transfected HEK293 cells (B)

In another illustration of this embodiment, the mCLCA1 protein was characterized. An in vitro transcription and translation system (TN™, Promega) was used for the in vitro expression of the full length cDNA (SEQ ID NO:33). Canine microsomes were used to glycosylate the product of in vitro translation. In addition, HEK293 cells were transfected with the cDNA of mCLCA1 using standard methods known to those skilled in the art (CaPO$_4$ or Lipfectamine, Life Technologies). Products were analyzed on SDS-PAGE gels. In addition, mCLCA1 cDNA was also used for transfection of cells. Proteins prepared by standard in vitro translation techniques or from lysates of transfected HEK293 cells were analyzed on Western blotting by using rabbit polyclonal antibodies against N-terminal (CU8) and the C-terminal region (CU21) of Lu-ECAM peptide. As shown in FIG. 6, protein bands of 130, 125, 90 kDa and triplet bands of 32-38 kDa were detected in transfected cells. CU8 reacted exclusively with the large sized bands of 90, 125 and 130 kDa whereas CU21 reacted with only the triplet of the smaller bands. This recognition pattern is similar to that observed for Lu-ECAM-1 and suggests that the ORF of mCLCA1 cDNA encodes a precursor protein, represented by alternate glycoforms of 125 and 130 kDa, that is post-translationally processed into 90 kDa and 38/32 kDa components.

Figure 7:
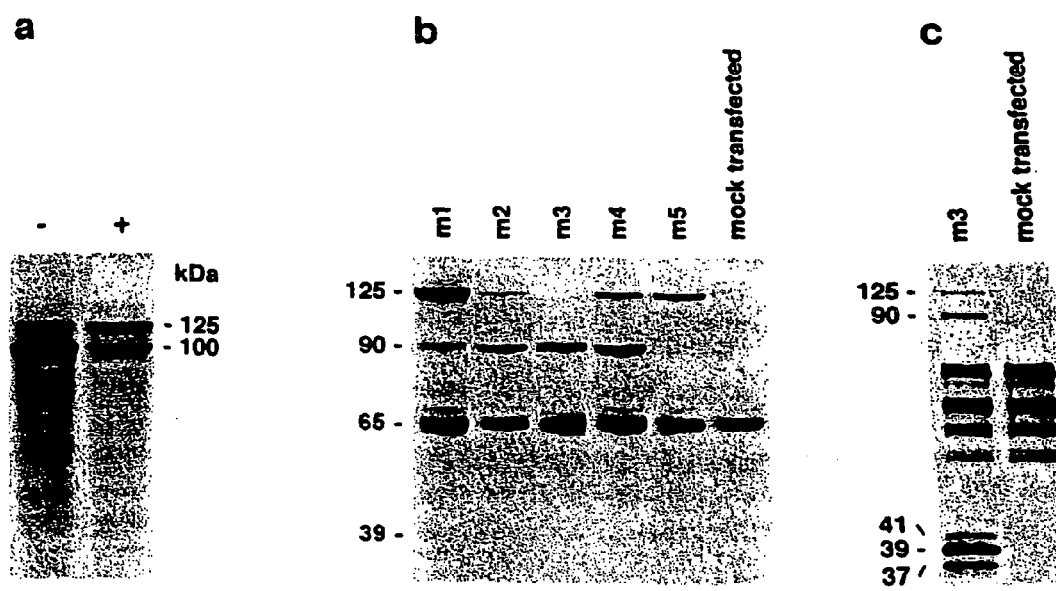
FIG. 7 is a representation of the biochemical analysis of hCLCA1 protein for in vitro translated (a), c-myc tagged hCLCA1 transfected HEK293 (b), and surface expression of c-myc tagged hCLCA1.

In another illustration of this embodiment, the hCLCA1 protein was characterized. The ORF of the hCLCA1 cDNA encodes a 914 amino acid protein with a calculated molecular weight of 100.9 kDA. In vitro translation of human CLCA1 cDNA yielded a single protein of approximately 100 kDa, consistent with its calculated size (FIG. 7). In the presence of canine microsomes the Mr of the polypeptide shifted to 125,000 indicating multiple glycosylations. Similar to Lu-ECAM-1 and mCLCA1, 37-40 kDa proteins were not detected in immunoblots of whole cell lysates but were coimmunoprecipitated with the 90 and 125 kDa protein. To ascertain whether the 125 kDa hCLCA1 protein is processed into 90 kDa and 30-40 kDa cleavage products in a manner similar to Lu-ECAM-1, c-myc tags were inserted in five different hydrophilic sites with high surface probability (m1-m5) and were overexpressed in HEK293 cells (Cravchik et al., 1993, Gene 137:139-143). Immonoblots of whole cell lysates probed with anti-myc antibodies revealed proteins of 125 and 90 kDa (FIG. 7b). However, immunoprecipitation of cell lysates following surface biotinylation indicated the presence of 37-41 kDa proteins similar to Lu-ECAM-1 and mCLCA1 (FIG. 7c).

In another illustration of this embodiment, the human CLCA2protein was analyzed. The predicted size of the full length protein (104 kDa) is consistent with the result of an in vitro translation assay yielding primary translation product of approximately 105 kDa (FIG. 8a) To ascertain whether the CLCA2 protein is cleaved into two subunits in mammalian cells as reported for other CLCAs, two constructs were generated with a c-myc tag within the amino or carboxy terminus respectively as described by Cravchik et al., 1993, Gene 137:139-143) and transfected into HEK293 cells. Immunoblots of cell lysates probed with anti-myc antibody identified an 86 kDa protein when the tag was inserted near the amino terminus (m1) and a 34 kDa protein when the tag was inserted near the amino terminus (m2)-FIG. 8b.

EXAMPLE 3

Tissue Distribution

This example illustrates the tissue distribution of CACC-AM. As an illustration, the distribution of Lu-ECAM-1/Lu-ECAM-1 complex in the respiratory tree, as demonstrated by immunohistochemistry. Tissue sections were probed with anti-Lu-ECAM-1 antibodies. Formalin-fixed sections of bovine trachea were first denatured by boiling for ten minutes in 4M urea in a microwave oven, then probed with polyclonal antibody R4 (raised against denatured Lu-ECAM-1). The sections were then incubated with donkey anti-rat IgG and avidin-peroxidase conjugate. The peroxidase conjugate was detected using diamino-benzidine as substrate, and then the slides were counterstained with hematoxylin. Lung sections were prepared and probed with mAb 6D3 as previously described (Zhu et al., 1993, mt. J. Cancer 53:68-633) except that a biotinylated secondary antibody was used, followed by the avidin-peroxidase conjugate, diamino-benzidine as substrate, and counterstaining with hematoxylin. The immunohistochemical analyses revealed that Lu-ECAM-1/Lu-ECAM-1 complex was expressed predominantly in endothelia of small to medium-size venules of the lung, and in the respiratory epithelia of bronchi and trachea. To confirm the distribution of expression of Lu-ECAM-1/Lu-ECAM-1 complex, and to distinguish it from that of the bovine epithelial chloride channel ("Ca-CC") described recently (Cunningham et al., 1995, supra), nucleic acid amplification was performed using specific primers as described herein in Example 4.

Tissue distribution for other CACC-AMs of the present invention were determined by Northern blot analysis and RT-PCR. Human multiple tissue Northern blots (Clontech) contained 2 µg poly-A+RNA per lane of the following tissues: heart, brain, placenta, lung, liver, skeletal muscle, kidney, pancreas, spleen, thymus, prostate, testis, ovary, small intestine, colon mucosa, peripheral blood leukocytes, stomach, thyroid, spinal cord, lymph node, trachea, adrenal gland, and bone marrow. Blots were hybridized labeled fragments for respective cDNAs. To exclude cross hybridization of related family members, highly stringent washing conditions were employed following the hybridization (two washes with 2×SSC, 0.1% SDS at 65° C. for 30 min, followed by two washes with 0.2×SSC, 0.1% SDS at 65° C. for 30 min). RT-PCR was performed using the above-mentioned conditions and primers to detect the cDNA fragments in poly-A+RNA samples from human tissues. PCR products were analyzed on an ethidium bromide stained agarose gel. To exclude amplification of a closely related family member, the PCR products were cut out of the gel, cloned into the pGem-T vector, and partially sequenced. In all RT-PCR assays, negative controls were included with water instead of RNA as template in the reverse transcription. To control for RNA quality as well as reverse transcription and PCR conditions, a fragment of EF-1a mRNA was amplified as described.

A mouse multiple tissue Northern blot when probed with HindIII fragment of mCLCA1 ORF revealed the presence of a 3.1 kb transcript in brain and spleen and transcripts of 5 kb and 3.1 kb in heart, lung, liver, and kidney.

For human CLCA1, a single mRNA species of 3.3 kb was detected in Northern blot hybridizations in small intestine and colon mucosa. Similar results were obtained with RT-PCR.

hCLCA2 mRNA was detected in trachea and mammary gland using the 2832 ORF of hCLCA1. While CLCA2 was not detected in the lung by Northern blot hybridization, the more sensitive RT-PCR revealed its expression in lung in addition to trachea and mammary gland suggesting a significantly lower expression level in the lung.

No signals were detected in any of the tissues tested on Northern blots using the 2817 cDNA of hCLCA3. However, by RT-PCR a fragment of the hCLCA3 cDNA could be amplified form all tissues tested, i.e. spleen, lung, trachea, thymus and mammary gland.

EXAMPLE 4

This example demonstrates that Lu-ECAM-1 and the bovine epithelial chloride channel ("Ca-CC") described recently by (Cunningham et al., 1995, J. Biol. Chem. 270: 31016-31026) aredistinct molecules.

1. Genetic Similarity

Sequence alignment of the open reading frame of SEQ ID NO:1 with the CA-CC cDNA shows that the nucleotide sequences share 92% identity at the DNA level. Comparing the deduced amino acid sequence of Lu-ECAM-1 (SEQ ID NO:2) with that of CA-CC shows 88% identity at the amino acid level. However, the differences appear randomly distributed, and thus, Lu-ECAM-1 and CA-CC appear to represent products of different genes.

2. Subunit Differences

As shown in FIGS. 2A, 2B, 3A, and 3B, it is clear that the precursor Lu-ECAM-1 is a protein with an apparent molecular size of either 120 kDa or 130 kDa. The precursor Lu-ECAM-1 gets processed to a 90 kDa Lu-ECAM-1 protein, and to either a 38 kDa or 32 kDa Lu-ECAM-1-associated protein. In contrast, CA-CC is a 140 kDa multimeric complex that can be reduced to a band comprised of 38 kDa subunits in the presence of a reducing agent (Cunningham et al., 1995, supra). This difference in subunit structure is further evidence that Lu-ECAM-1/Lu-ECAM-1 complex is a glycoprotein distinct from CA-CC.

3. Molecular Expression Differences

It is possible that immunohistochemical staining with polyclonal antibody to Lu-ECAM-1 could detect CA-CC if CA-CC shared a cross-reactive epitope with Lu-ECAM-1. To distinguish-Lu-ECAM-1 expression from CA-CC expression in tissues, reverse transcriptase polymerase chain reaction was performed. Messenger RNA (500 ng) from bovine lung tissue, from bovine spleen tissue, from bovine tracheal epithelium, and from cultured bovine aortic endothelial cells was reverse-transcribed with random oligonucleotide primers and reverse transcriptase in a 20 µil reaction volume. Primers specific for Lu-ECAM-1 sequences (primer pairs "L1":SEQ ID NOS: 17 and 18, "L2": SEQ ID NOs: 19 and 20), and primers specific for CA-CC sequences (primer pairs "T1":SEQ ID NOs: 21 and 22, and "T2" SEQ ID NOs: 23 and 24) were confirmed for selectivity by control experiments with a Lu-ECAM-1 CDNA clone. Amplification was performed using 1 µl of the respective cDNA substrate for 35 cycles of amplification in a reaction volume of 50 [Li using 0.5 units of thermostable DNA polymerase, 200, uM of each dNTP, 1.5 mM $MgCl_2$, and 1 µM of the respective primer pair. The cycling protocol was 94° C. for 20 seconds, 55° C. for 10 seconds, and 72° C. for 10 seconds, with a time increment of 2 seconds per cycle for annealing and ° for 10 minutes. Aliquots (5 µl) of each amplification reaction was fractionated on a 1.5% agarose gel, and stained with ethidium bromide.

Figure 4A:
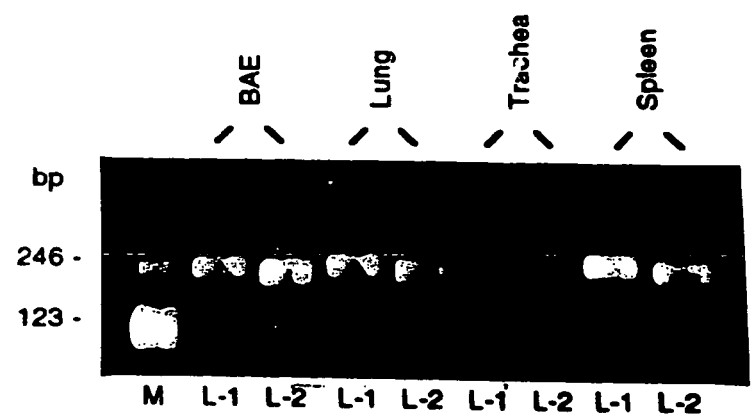
FIG. 4A is a representation of a ethidium bromide stained agarose gel containing the results of reverse transcriptase polymerase chain reaction analysis of bovine aortic endothelial cells ("BAEC"), lung tissue, tracheal epithelium, and spleen tissue using Lu-ECAM-1 specific primer pairs L1,and L2.
Figure 4B:
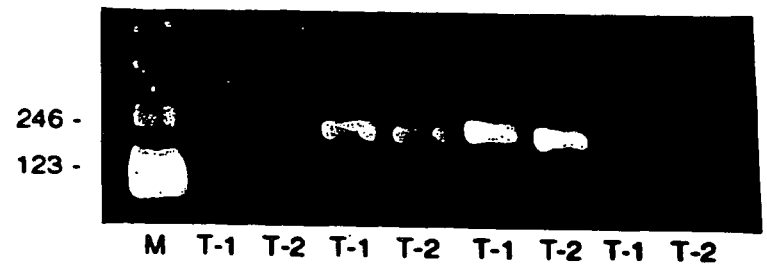
FIG. 4B is a representation of a ethidium bromide stained agarose gel containing the results of reverse transcriptase polymerase chain reaction analysis of bovine aortic endothelial cells ("BAEC"), lung tissue, tracheal epithelium, and spleen tissue using bovine tracheal chloride channel ("CaCC") specific primer pairs T1, and T2.

The calculated size for product amplified using primer pair L1 is 232 bp; the calculated size for product amplified using primer pair L2 is 218 bp; the calculated size for product amplified using primer pair T1 is 231 bp; and the calculated size for product amplified using primer pair T2 is 218 bp. As shown in FIG. 4A, Lu-ECAM-1 is expressed in bovine aortic endothelial cells, lung tissue, and spleen, tissue, but not in tracheal epithelium. In contrast, as shown in FIG. 4B, CA-CC is expressed in lung tissue and tracheal epithelium, but not in bovine aortic endothelial cells nor spleen tissue. These results further support that Lu-ECAM-1 and CA-CC are different molecular entities, with Lu-ECAM-1 being expressed in venular endothelial cells, and CA-CC being expressed in tracheal and bronchial epithelial cells.

EXAMPLE 5

This embodiment illustrates that a nucleic acid molecule comprising a nucleotide sequence encoding CACC-AM, or a variant sequence thereof, or encoding one or more CACC-AM associated proteins, can be inserted into various vectors including phage vectors and plasmids. Successful expression of the protein(s) requires that either the insert comprising the nucleotide sequence, or the vector itself, contain the necessary elements for transcription and translation (expression control elements) which is compatible with, and recognized by the particular host system used for expression. A variety of host systems may be utilized to express the recombinant protein(s), which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology, including methods described above, various promoters and enhancers can be incorporated into the vector or the nucleic acid molecule encoding the recombinant protease, to increase the expression of the recombinant protein(s), provided that this increased expression is compatible with (for example, non-toxic to) the particular host cell system used. The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene or the variant sequence and expression into the recombinant protein. For example, bacterial, phage, or plasmid promoters known in the art from which a high level of transcription has been observed in a host cell system comprising *E. coli* include the lac promoter, trp promoter, tac promoter, reca promoter, ribosomal RNA promoter, the $P_R$ and $P_L$ promoters, lacUV5, ompf, bla, lpp, and the like, may be used to provide transcription of the inserted DNA sequence encoding the recombinant protein.

As known to those skilled in the art, such vectors for expression in mammalian cells can be selected from plasmids, viruses, and retroviruses. For a recent review of vectors useful in gene therapy, see Weichselbaum and Kufe (1997, Lancet, 349:S1O-S12). The features of a vector which make it useful in the methods of the present invention include that it have a selection marker for identifying vector which has inserted therein the nucleotide sequence to be expressed; restriction sites to facilitate cloning; and the ability to enter and/or replicate in mammalian cells. Examples of a preferred vector for the in vivo introduction of-a recombinant vector into mammalian cells include, but are not limited to viral vectors. Virus-based vectors are one preferred vehicle as they infect cells in vivo, wherein during the infection process the viral genetic material is transferred into the cells. A retroviral vector, such as a plasmid containing AAV (Adeno-associated virus) sequences, has been described previously (see for example Chatteijee et al., 1992, Science, 258:1485-1488; U.S. Pat. No. 5,252,479, herein incorporated by reference). Examples of other vectors for the in vitro or in vivo introduction into mammalian cells include retroviral vectors (Miller et al., 1989, BioTechriiques 7:980-990; Korman et al., 1987, Proc. Nati. Acad. Sci. USA 84:2150-54), papovavirus episomes (U.S. Pat. No. 5,624,820, herein incorporated by reference), and adenovirus vectors (U.S. Pat. No. 5,585,362, herein incorporated by reference). Promoters are known to those skilled in the art, and may include viral or viral-like basal promoters like the 5V40 late promoter, the RSV promoter, the CMV immediate early promoter, and a VL3O promoter; and cellular promoters (See, e.g., Larsen et al., 1995, Nucleic Acids Res. 23:1223-1230; Donis et al., 1993, BioTechniques 15:786-787; Donda et al., 1993, Mol. Cell. Endocrinol. 90:R23-26; and Huper et al., 1992, In Vitro Cell Dev. Biol. 28A:730-734).

In one illustration of this embodiment, a nucleotide sequence comprising clone 1 (SEQ ID NO:1) was placed under the control of a tetracycline-regulated promoter in a commercially available plasmid (pTet-Splice; GIBCO). The construction was accomplished in two steps. An amplified product was generated that corresponded to the 3' end of clone 1 cDNA (nucleotide 2391 to nucleotide 2780 of SEQ ID NO:1) using a 5' primer containing an EcoRI restriction site (SEQ ID NO:25) and a 3' primer containing a SpeI restriction site (SEQ ID NO:26). The cycling protocol included 93° C. for 35 seconds, 55° C. for 60 seconds, 72° C. for 3 minutes for 40 cycles followed by a 10 minute incubation at 72° C. using a thermostable DNA polymerase. The product was cleaved with EcoRI and SpeI, then cloned into corresponding restriction sites in the plasmid. The resultant plasmid was selected and then sequenced to confirm absence of mutations. This recombinant plasmid was then cleaved with EcoRI and BglII. To reconstitute the open reading frame encoding Lu-ECAM-1, the 2.3 kb EcoRI/BglII fragment was excised from clone 3 and inserted into the plasmid. The resulting plasmid, pTet-Splice-Lu-ECAM-1, was then co-transfected into HEK293 cells with another plasmid (pTet-tTAK) that encodes a transcriptional activator specific for the pTet-Splice vector. Transfection was done using a transfection reagent (lipofectamine) according to the manufacturers instructions. Cells were harvested 24 hours after the start of transfection. Immunoblot analysis of the cells using polyclonal R41 resulted in the detection of recombinant Lu-ECAM-1 precursor of 120 kDa, and recombinant Lu-ECAM-1-associated protein of 38 kDa. When the cells were probed in immunoblot with anti-peptide antibody CU8, detected was recombinant Lu-ECAM-1 precursor of 120 kDa, and recombinant Lu-ECAM-1 of 90 kDa.

In another embodiment of the invention, mCLCA1 cDNA was cut from the pBluescript vector (Stratagene) with Sacd and PvuI, blunt ended with Klenow Polymerase and inserted into the tetracycline sensitive mammalian expression vector (pTet-splice, Life Technologies, Inc.) at the EcoRV site. HEK293 cells were cotransfected with mCLCA1 cDNA cloned into the pTet-splice along with a vector expressing a tetracycline activator (pTet-tTak) using standard transfection techniques well known to those skilled in the art and as described above (Lipofectamine, Life Technologies, Inc.).

Cells were cotransfected with a reporter vector as described above. In another illustration of this embodiment, human CLCA1, HEK293 cells were transfected with either pcDNA 3.1 containing the CLCA1 insert and a reporter vector (enhanced green fluorescent protein, EGFP, CLONTECH) or the reporter vector alone. Transfection can be carried out by standard techniques known to those skilled in the art including CaPO4 precipitation or Lipofectamine (Life Technologies).

For human CLCA2, HEK293 cells were transfected using Lipofectamine using manufacturer's instructions. For example, 5 ul lipid and 0.5 ul of CLCA2 were cloned into pcDNA 3.1 per 35 mm well in a 2-3 hour incubation. For expression studies, the 2,832 bp CLCA2 ORF was PCR amplified from human trachea poly-A$^+$ RNA (Clontech) following reverse transcription with Superscript RNase H reverse transcriptase (Life Technologies) and random hexamer priming. PCR was performed with Pwo DNA Polymerase (Boehringer; initial denaturation at 94° C. for 3 min, 35 cycles of 94° for 50 s, 58° C. for 30 s, and 72° C. for 2 min with a time increment of 3 s per cycle for each extension step (72° C.), followed by a final extension step of 72° C. for 8 min). Primer sequences were (upstream primer: SEQ ID NO:41, downstream primer: SEQ ID NO:42 with NotI-linkers underlined). PCR products were gel purified, incubated with NotI, and cloned into the expression vector pcDNA3.1 (Invitrogen). Four different PCR products were sequenced to control for potential PCR-induced sequence errors. Cells were simultaneously cotransfected with a reporter vector as described above. Chloride channel conductance activity was recorded after allowing the cells to recover for 24 hours.

The 2817 bp fragment of the hCLCA3 cDNA cloned into pcDNA3.1 was simultaneously transcribed and translated as described for the other CACC-AMs. Samples were analyzed by 10% SDS-PAGE (5 µl of a 25 µl reaction), followed by drying of the gel and exposure to film for 8 h. Protease protection assays were performed as described to ascertain whether hCLCA3 translation products were translocated into the microsomes and thus entered the secretory pathway. In the presence of microsomal membranes in vitro translated and $^{35}S$-labeled wild type hCLCA3 was digested with Proteinase K (Sigma; 100 µg/ml) for 60 min on ice with or without detergent present (0.5% Nonidet-P 40). The reaction was stopped by adding phenylmethylsulfonyl fluoride and the products were analyzed by 10% SDS-PAGE and exposure to film. To allow for immunological detection of the translation products, three immunotagged cDNA clones were constructed (m1 to m3) by inserting a partial sequence of the human c-myc protein (EQKLISEEDL; SEQ ID NO: 47) into the amino termini of the first (m1), the second (m2), or both (m3) ORFS. Generation of these constructs using overlap extension PCR and Pwo DNA polymerase (Boehringer) was as described. Correct sequences of the constructs were verifiedby sequencing. Immunotagged DNA constructs were either in vitro translated as described above or transfected into 70% confluent human embryonic kidney (HEK) 293 or chinese hamster ovary (CHO) cells via the Lipofectamine Plus method (Life Technologies) Cell lysates were harvested after 48 h, resolved via 10% SDS-PAGE, and electroblotted onto nitrocellulose. Blots were probed with mouse-anti-human c-myc antibody 9E10 (1 µg/ml; Calbiochem) as primary antibody, horseradish peroxidase-conjugated goat anti-mouse antibody (0.2 µg/ml) as secondary antibody, and developed using enhanced chemiluminescence (Amersham). Secretion of the recombinant hCLCA3 protein into the culture supernatant was assayed by concentrating the conditioned medium (24 to 48 h after transfection) of HEK293 or CHO cells transfected with construct m3 using ultrafiltration devices with a molecular cutoff at 10 kDa (Ultrafree-15, Biomax-10 filter; Millipore; centrifugation at 2,000 g for 30 min at 4° C.).

EXAMPLE 6

This embodiment demonstrates that the CACC-AMs of the present invention can function as adhesion molecules. As an illustration, a recombinant LU-ECAM-1, encoded by a nucleic acid molecule according to the present invention, has unexpectedly improved biological activity. Recombinant (r) Lu-ECAM-1 and wild type (wt) Lu-ECAM-1 were compared in their adhesion ability to lung-metastatic B16-F10 melanoma cells. Using anti-Lu-ECAM-1 mAb 6D3, wtLu-ECAM-1 was purified from extracts of bovine aortic endothelial cells, and rLu-ECAM-1 was purified from extracts of transfected HEK293 cells. The tumor cell adhesion assay was performed as described previously (Zhu et al., 1992, supra). Briefly, 100 µg/ml in phosphate buffered saline of either wtLu-ECAM-1 or rLu-ECAM-1 was used to coat wells of 96 plates overnight at 4° C. Wells were then washed with tissue culture medium, and each well is seeded with a suspension of tissue culture medium and $2 \times 10^4$ tumor cells which had been radio-labelled. After being spun onto the coated wells at 15 g for 1 minute, and incubated for 10 minutes at 37° C., nonadherent tumor cells were spun off at 150 g for 5 minutes. Adherent tumor cells were then dissolved in 1% SDS and counted in a liquid scintillation counter. Tumor cell attachment is recorded as the percent cells bound of the total cells seeded. Inhibition of tumor cell adhesion is determined by first incubating the Lu-ECAM-1 coated wells with mAb 6D3 (10 µg/ml) for 1 hour at room temperature before the tumor cells are added.

Figure 5:
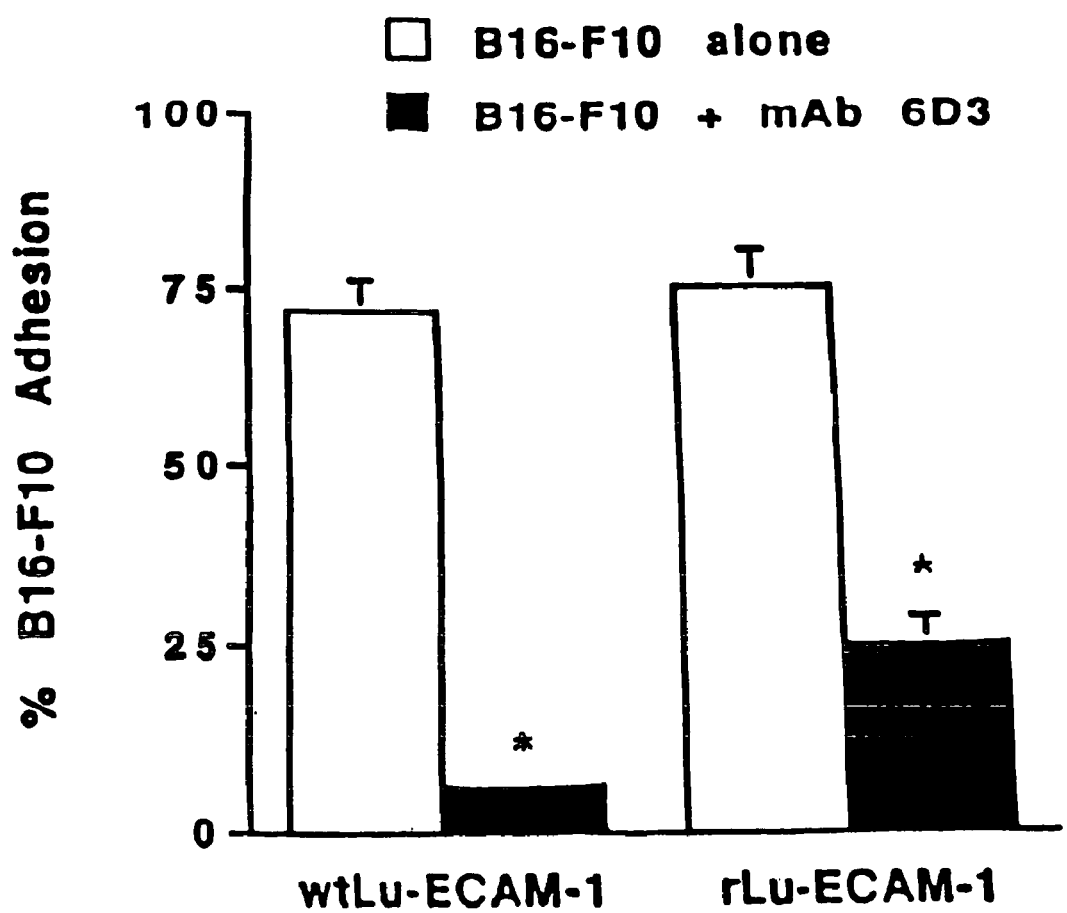
FIG. 5 is a bar graph illustrating lung-metastatic tumor cell adhesion to wild type Lu-ECAM-1 in the presence or absence of anti-Lu-ECAM-1 mAb 6D3; and lung-metastatic tumor cell adhesion to recombinant Lu-ECAM-1 in the presence or absence of anti-LuECAM-1 mAb 6D3.

As shown in FIG. 5, recombinant Lu-ECAM-1 has unexpectedly improved biological activity (e.g., adhesive function to lung-metastatic tumor cells) as compared to wild type Lu-ECAM-1. More particularly, rLu-ECAM-1 supported adhesion of 87% of lung-metastatic tumor cells, whereas wtLu-ECAM-1 supported adhesion of only 43% of lung-metastatic tumor cells. Lung-metastatic tumor cell adhesion to wtLu-ECAM-1 was almost completely blocked by anti-Lu-ECAM-1 mAb 6D3, whereas lung-metastatic tumor cell adhesion to rLu-ECAM-1 was only partially inhibited (66%) by the concentration of anti-Lu-ECAM-1 mAb 6D3 used.

EXAMPLE 7

Figure 9:
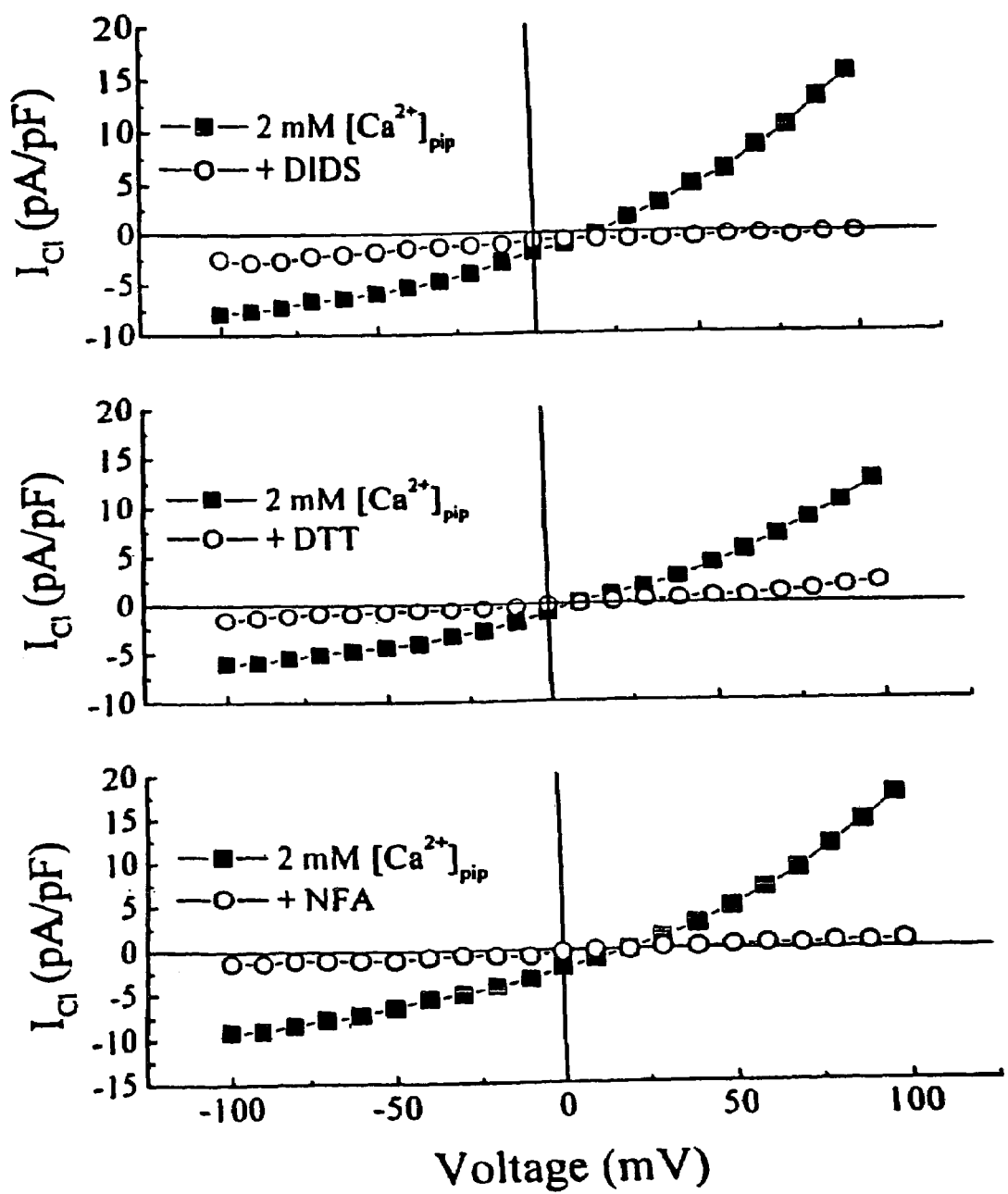
FIG. 9 is a representation of whole cell currents in mCLCA1 transfected HEK293 cells.

A comparison of the amino acid sequence of the CACC-AMs of the present invention is shown in FIG. 9. Sequence alignment and homology searches were carried out by using standard commercial software. For example, BLAST program was used for homology searches in existing data bases, and Megalign of the DNAStar package (Lasergene) was used for multiple sequence alignment. The sequence alignment of the four CACC-AMs of the present invention and the bovine CLCA (Cunningham et al. supra) indicates conservation throughout the entire length of the sequence, without the compartmentalization of more conserved domains. No significant homologies to any other chloride channel proteins were detected.

Table 1 illustrates a comparison of the size of the various mammalian Lu-ECAM-1 proteins and Lu-ECAM-1 associated proteins as encoded-by the respective open reading frames.

TABLE 1

| Species | SEQ ID NO: | Total # of Amino Acids | Predicted Size |
|---|---|---|---|
| bovine | 2 and 3 | 905 a.a. | 90 kD, 32-28 kD |
| human hCLCA1 | 28 | 914 a.a. | 90 kD, 40 kD |
| human hCLCA3 | 30 | 1000 a.a. | 130 kD (processing not known) |
| human hCLCA2 | 32 | 943 a.a. | 130 kD 90 kD, 35 kDa |
| murine mCLCA | 34 | 902 a.a. | 130 kD, 125 kD 90 kD, 32-38 kD |

Table 2 is a comparison among the mammalian Lu-ECAM-1 family showing both an approximated amino acid similarity and an approximated amino acid identity (expressed as "similarity/identity").

TABLE 2

| | bovine (SEQ ID NOs: 2&3) | murine (SEQ ID NO: 34) | human (SEQ ID NO: 28) | human (SEQ ID NO: 30) | human (SEQ ID NO: 32) |
|---|---|---|---|---|---|
| bovine (SEQ ID NOs: 2&3) | 100/100 | 81.3/70.8 | 67.4/52.4 | 85.7/77.4 | 63.7/49.8 |
| murine mCLCA (SEQ ID NO: 34) | — | 100/100 | 67.5/52.7 | 80.9/69.5 | 62.8/48.4 |
| human hCLCA1 (SEQ ID NO: 28) | — | — | 100/100 | 65.3/51.4 | 62.3/44.7 |
| human hCLCA3 (SEQ ID NO: 30) | — | — | — | 100/100 | 62.1/48.2 |
| human hCLCA2 (SEQ ID NO: 32) | — | — | — | — | 100/100 |

Table 3 is a comparison among the mammalian Lu-ECAM-1 gene family showing approximated nucleic acid similarities (expressed in %).

TABLE 3

| | bovine (SEQ ID NO: 1) | murine (SEQ ID NO: 33) | human (SEQ ID NO: 27) | human (SED ID NO: 29) | human (SEQ ID NO: 31) |
|---|---|---|---|---|---|
| bovine (SEQ ID NO: 1) | 100 | 76.7 | 63.1 | 85.9 | 64.4 |
| murine (SEQ ID NO: 33) | — | 100 | 62.6 | 76.1 | 61.2 |
| human (SEQ ID NO: 27) | — | — | 100 | 63.3 | 58.9 |
| human (SEQ ID NO: 29) | — | — | — | 100 | 62.6 |
| human (SEQ ID NO: 31) | — | — | — | — | 100 |

EXAMPLE 8

This embodiment illustrates that the full length cDNAs of the present invention encode calcium sensitive chloride channels. The various cDNAs were used for transfection of a cell line. For electrophysiological studies, cells were also cotransfected with a reporter vector (PEGFP, CLONTECH). Cotransfection with a reporter vector allows for easy identification of transfected cells by visualization under a fluorescent microscope. Whole cell recording was then carried out in the transfected cells to determine the presence of calcium sensitive chloride channels.

Transfected cells were used for electrophysiological recording. Cells were superfused with a bath solution containing 112 mM NMDG-Cl, 30 mM sucrose, 1 mM EGTA, 0.366 mM $CaCl_2$, 2 mM $MgCl_2$, 5 mM N-2-hydroxyxyethanylpiperazine-N-2-ethanesulfonic acid. Whole cell channel activity was recorded in transfected cells by using borosilicate glass electrodes (tip resistance 4-9 M ohms) filled with the bath solution. Recordings were carried out in the presence or absence of a calcium channel inhibitors (DIDS, niflumic acid and DTT). To determine the effect of ionomycin on channel activity, electrodes filled with standard bath solution containing either 5 mM ATP and 1 mM EGTA in the presence of low intracellular calcium. After gigaohm seal formation, cells were clamped at +20 mV. Whole cell currents were recorded at room temperature, sampled at 5-10 kHz and filtered at 1-2 kHz. The I-V relationship was determined using 300 ms voltage steps from a holding potential of +20 mV to potentials from −100 to +100 mV at 10 mV intervals. To normalize measured membrane currents to membrane currents to membrane capacitance, the capacitive current transient recorded in response to a 10 mV hyperpolarizing pulse was integrated and divided by the given voltage to give total membrane capacitance ($C_m$) for each cell.

Figure 10:
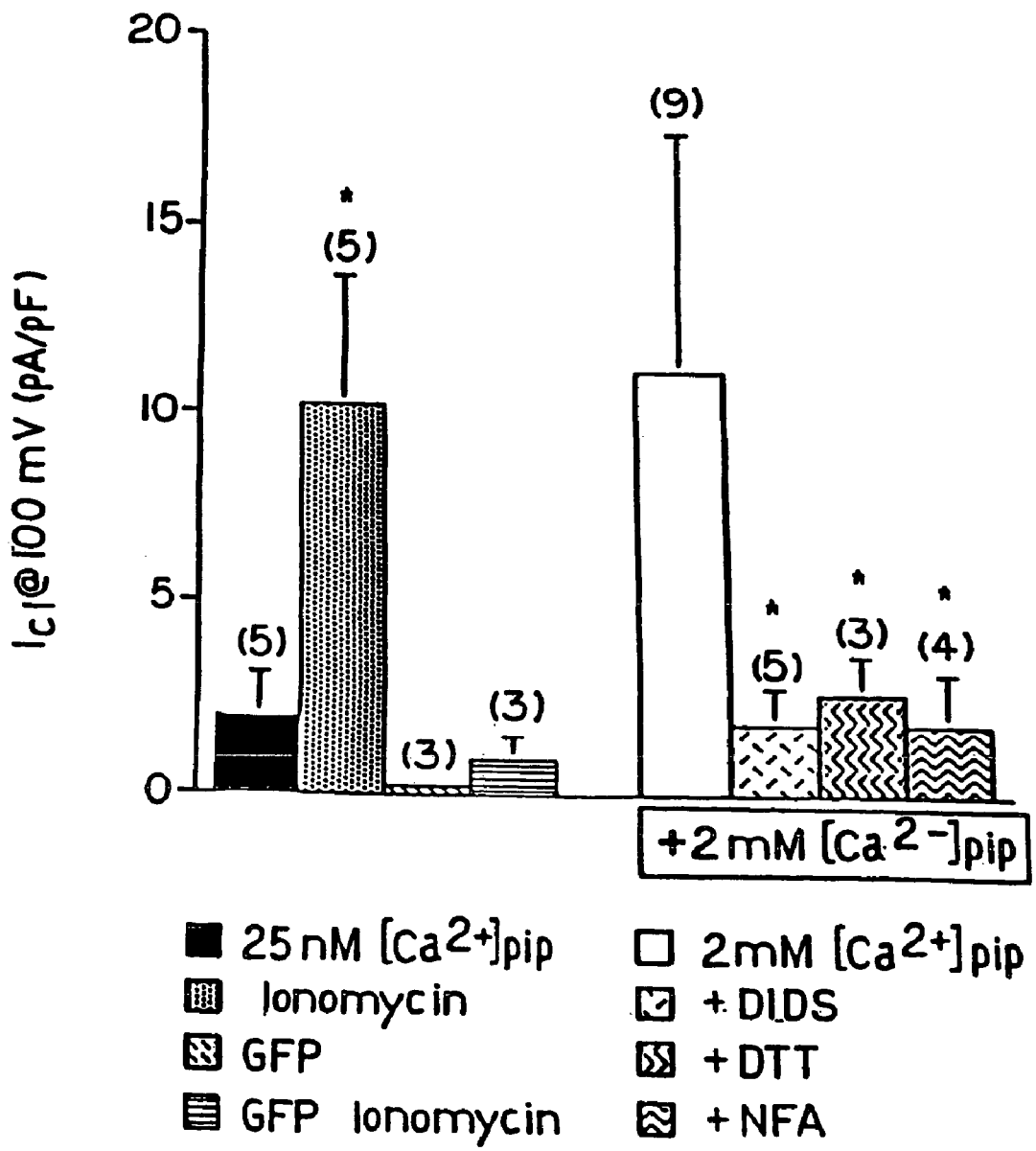
FIG. 10 is an illustration of the summary the effects of inhibitors on mCLCA1 current expression.

As shown in FIG. 9, expression of mCLCA1 in HEK293 cells was associated with the appearance of a novel $Ca^{2+}$ sensitive Cl— channel as determined by whole cell recordings in the presence and absence of the $Ca^{2+}$ ionophore ionomycin (2 uM). As shown in FIG. 9b, at low intracellular free Ca2+ concentrations, the basal current at +100 mV in mCLCA1-transfected cells was 2.05±1.09 pA/pF. With ionomycin the current increased to 10.23±3.46 pA/pF. No significant effect of these manipulations was seen in non-transfected or control-transfected cells. Basal currents in the presence of 2 mM Ca2+ in transfected cells averaged 12.01±6.31 pA/pF. Perfusion of 300 uM DIDS reduced the current to 1.84±0.96. A similar effect was seen with NFA and DTT. These results indicate that the expression of mCLCA1 in HEK293 cells is associated with the appearance of a Ca2+ sensitive chloride conductance. Under whole cell conditions, the current was outwardly rectified and inhibited by the anion channel blockers DIDS and NFA as well as the reducing agent DTT. This data is summarized in FIG. 10.

Figure 11:
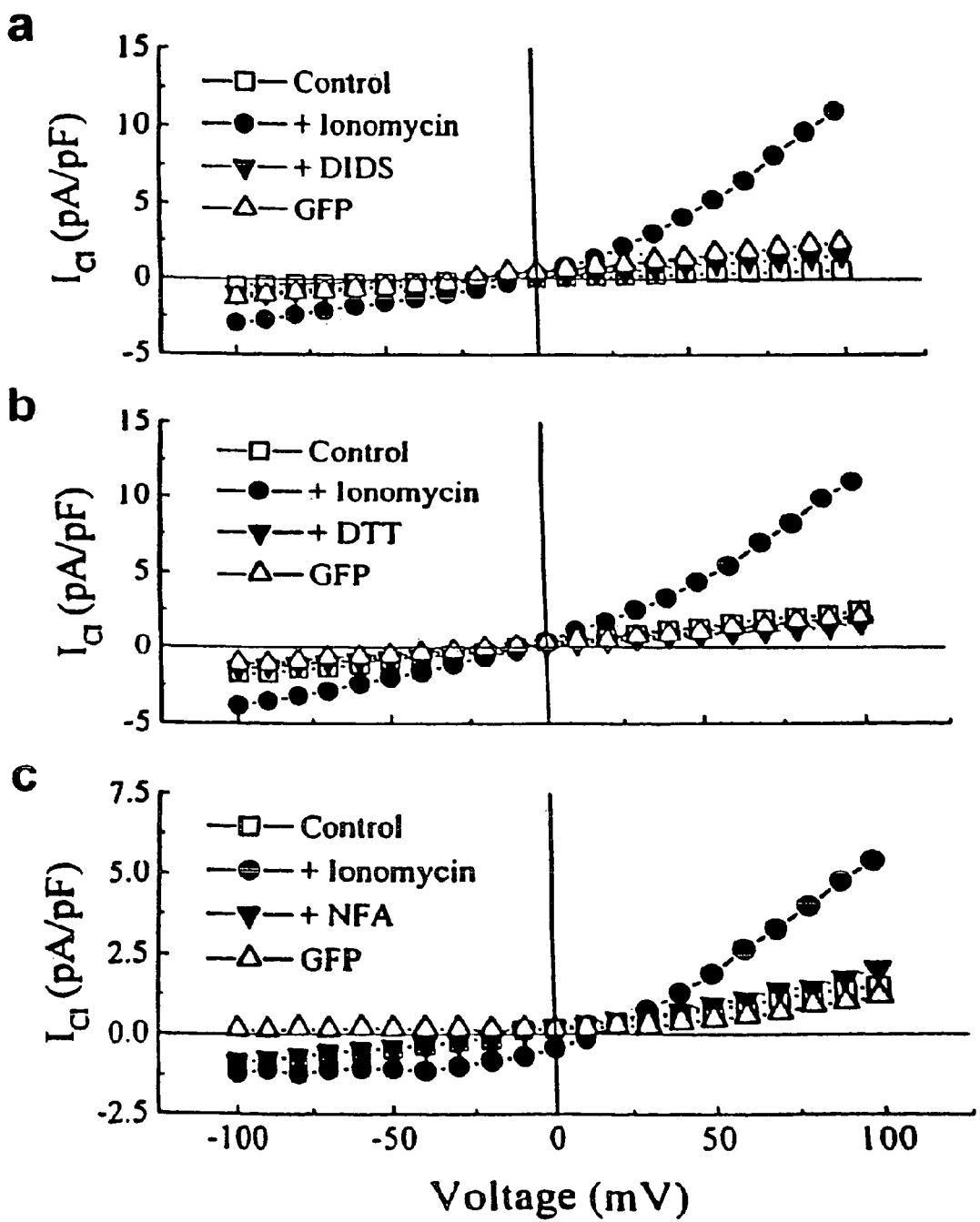
FIG. 11 is a representation of whole cell currents in hCLCA1-transfected HEK293 cells.
Figure 12:
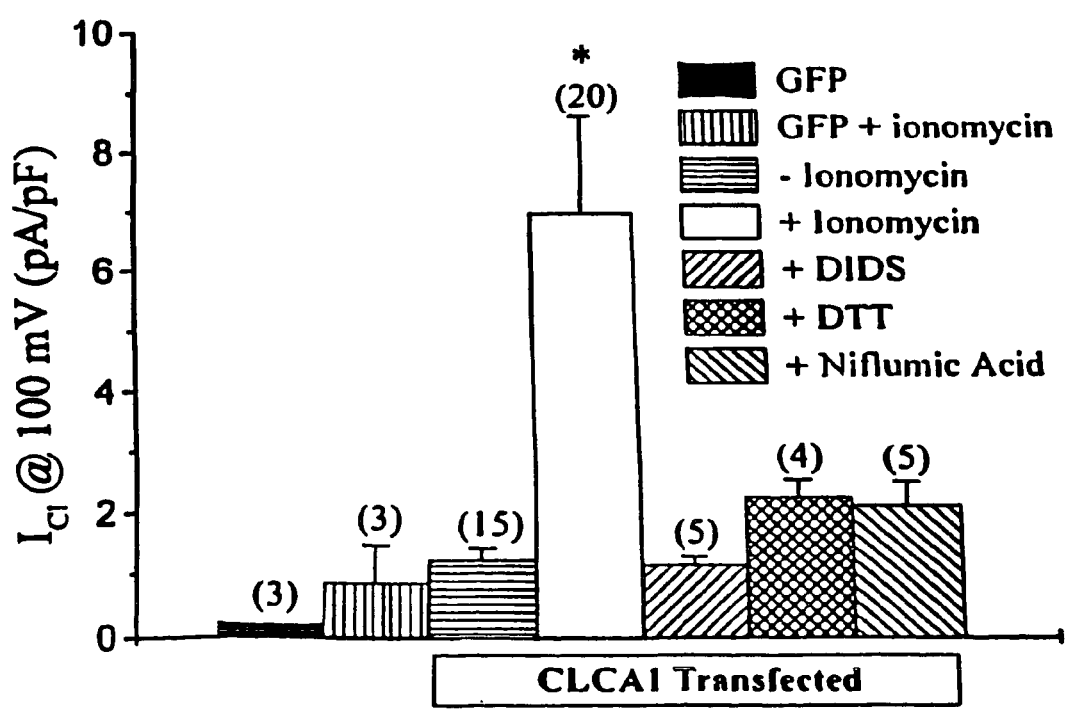
FIG. 12 is an illustration of the summary the effects of inhibitors on hCLCA1 current expression.

Whole cell recording of cells transfected with hCLCA1 cDNA demonstrated the induction of calcium sensitive chloride channels(FIG. 11). External perfusion of ionomycin (2 uM) was associated with an increase in the maximally activated current at +100 mV from 0.65 to 11.06 pA/pF. The current voltage relationship was outwardly rectified and reversed at 0 mV under symmetrical recording conditions. No effect of ionomycin was observed on non-transfected cells or control transfected cells. Addition of DIDS, DTT or niflumic acid reduced the currents to 1.63, 1.67 and 2.07 pA/pF respectively Cell attached patch recordings of single channels confirmed the presence of calcium sensitive anion channel (data not shown). This data is summarized in FIG. 12.

Figure 13A:
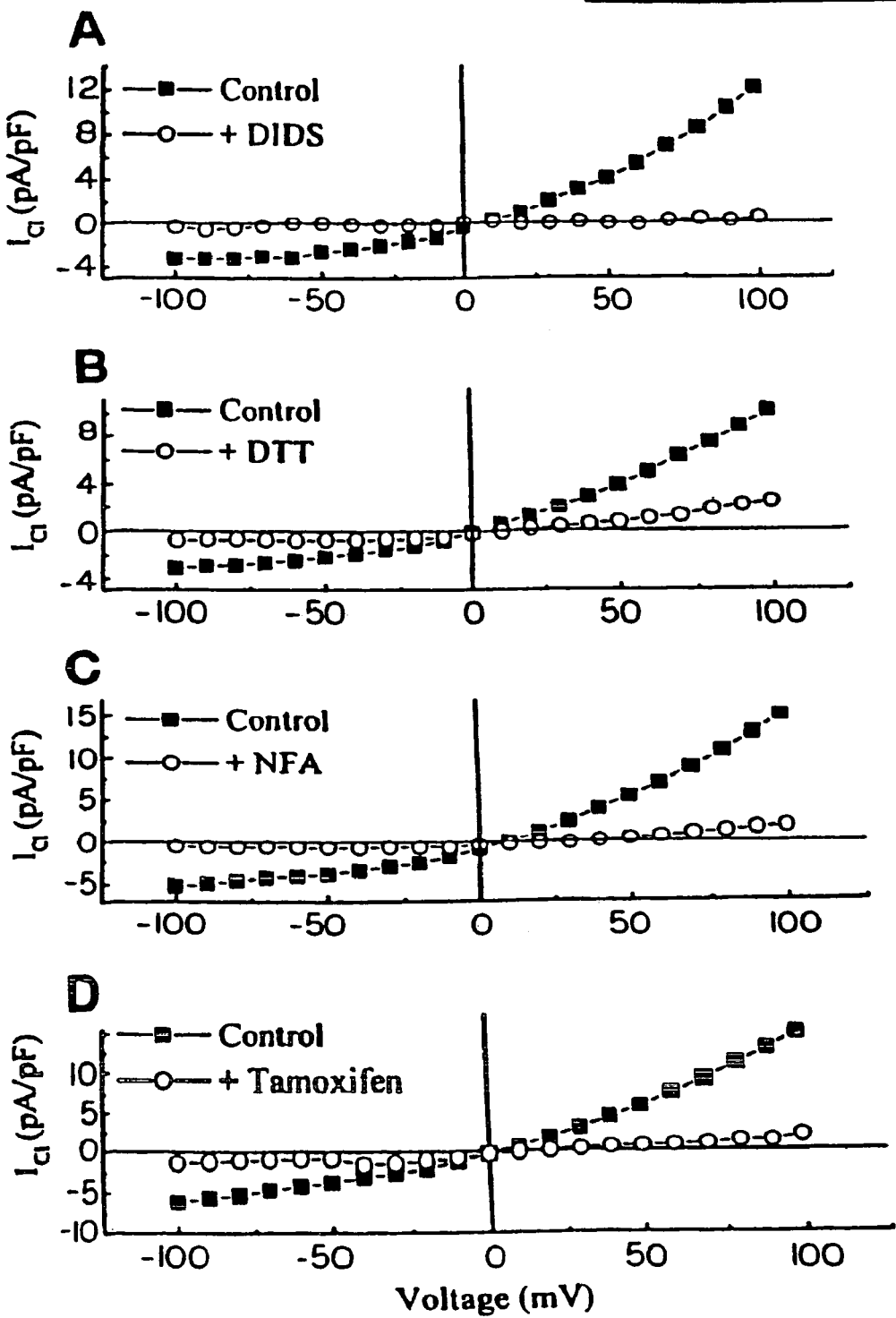
FIGS. 13A and 13B illustrate electrophysiological analysis of hCLCA2.
Figure 13B:
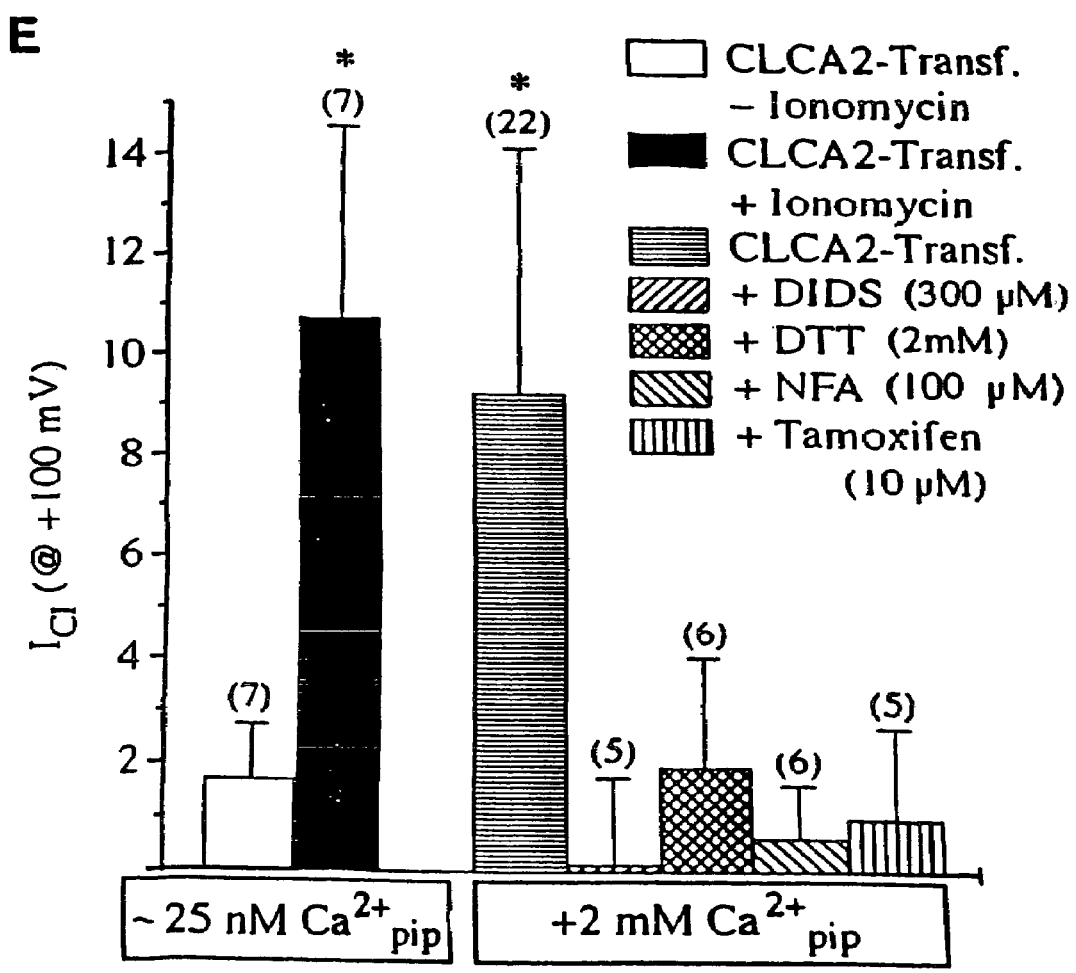

Whole cell recordings of hCLCA2 transfected HEK293 cells exhibited s slightly outwardly rectifying current/voltage relationship that was absent from control cells (transfected with vector alone; FIG. 13). This current was sensitive to DIDS (300 uM), DTT (2 mM), niflumic acid (100 uM), and tamoxifen (10 uM). When the pipet solution contained low Ca2=(about 25 nM) with 2 mM Ca2+ in the bath, perfusion of the Ca2+ ionophore ionomycin (4 uM) through the bath also activated the current (FIG. 13e).

These results indicate that the expression of CACC/AM molecules disclosed herein and their variants is associated with the appearance of calcium sensitive chloride channels.

EXAMPLE 9

This embodiment illustrates uses of the sequences according to the present invention. In one embodiment of the present invention, an individual having a primary tumor having lung-metastatic capabilities is treated with an anti-adhesion therapy comprising administering to the individual a therapeutically effective amount of a composition comprising either antibody raised to rLu-ECAM-1 or recombinant Lu-ECAM-1 complex, or a vector for expressing a soluble form of rLu-ECAM-1 or rLu-ECAM-1 complex which can then bind to the lung-metastatic tumor cells. Either composition may function to prevent lung-metastatic tumor cell adhesion to the lung venule endothelial cells, thereby preventing colonization by the metastatic tumor cells. As known to those skilled in the art, an effective amount of a therapeutic composition may depend on the route of administration (e.g., intravenous or other route known in the art), and physiological factors including the age, size, and rate of metabolism of the individual to be treated.

Another embodiment of the present invention is a method for providing calcium-dependent chloride conductance channels to mammalian cells. Recombinant Lu-ECAM-1 or rLu-ECAM-1 complex may form a chloride channel which may affect chloride secretion, and hence fluid secretion, from the cell. It may be that the chloride ion channel is coupled to the adhesion process involving the binding of Lu-ECAM-1 to a ligand, as similarly observed for the adherence and growth of lymphatic endothelial cells (Martin et al., 1996, supra). Thus, in mammalian cells in which the membrane chloride ion channels are deficient in number or function (e.g., in airway epithelial cells of cystic fibrosis patients), a method of providing to mammalian cells a calcium-dependent chloride conductance channel, rLu-ECAM-1 or rLu-ECAM-1 complex, comprises administering directly to the lung endothelial and/or epithelial cells (in vitro or in vivo) an expression vector. The expression vector contains a nucleic acid molecule(or a variant thereof) operably linked to expression control sequences, wherein the nucleic acid molecule encodes either rLu-ECAM-1 or rLu-ECAM-1 complex, with the resultant expression vector being introduced into the mammalian cell, and a functional calcium-dependent chloride conductance channel produced in the mammalian cells which contain the expression vector. The cells targeted for chloride conductance channel production may include airway cells selected from the group consisting of tracheal, bronchial or lung cells. If the cells are transfected in vitro, the transfected cells may then be introduced in vivo into the area of the lungs of the individual which is deficient in chloride channel function.

EXAMPLE 10

This Example describes the antibodies used where noted in the Examples that follow Example 10. Antibodies against the $\beta_4$ integrin ectodomain were mouse α-human monoclonal antibody (mAb) 3E1 (from Dr. E. Engvall, The Burnham Institute, La Jolla, Calif.), rabbit α-human polyclonal antibody (pAb) H-101 (Santa Cruz Biotechnology, Santa Cruz, Calif.), and rat α-mouse mAb346-11A (BD Pharmingen), and against the $\beta_4$ cytoplasmic domain rabbit α-human pAb1922 (Chemicon, Temecula, Calif.). Mouse α-human $\beta_1$ integrin mAb (clone 18) was from BD Pharmingen, and α-human $\beta_3$ mSb25E11 was from Chemicon. Mouse mAb9E10 was against the Myc protein tag (Calbiochem), mouse mAb(F-7) was against the HA tag (Santa Cruz Biotechnology), and rabbit pAb(B-14) and mouse rnAb(Z-5) were against glutathione S-transferase (GST) (Santa Cruz Biotechnology). Horseradish peroxidase-conjugated goat α-mouse, α-rat, and α-rabbit IgG antibodies were from Jackson ImmunoResearch Laboratories (West Grove, Pa.). Anti-bCLCA2 (Lu-ECAM-1) mAb6D3 was produced in BALB/c mice as previously described (Zhu et al. (1991) Proc. Natl. Acad. Sci. U.S.A. 88, 9568-9572; Zhuet al (1991) J. Histochem. Cytochem. 39, 1137-1142) and selected for blocking the adhesion of lung-metastatic cancer cells (e.g. R3230AC-MET; and B16-F10) to bCLCA2-expressing bovine aortic endothelial cells. The antibody cross-reacts with mCLCA1 Rat plasma fibronectin was from Invitrogen. Purified $\beta_1$ ($\alpha_5$ $\beta_1$) and $\beta_3$ ($\alpha_v$ $\beta_3$) integrins were purchased from Chemicon. Human placental and EHS laminins as well as all other reagents were from Sigma. Genemed Synthesis, Inc. (South San Francisco, Calif.) prepared synthetic peptides of $\beta_4$(184-203) and $\beta_1$(207-213).

EXAMPLE 11

This Example describes the construction of plasmids containing GST-bCLCA2 fragments and plasmids containing integrin fragments. To generate GST fusion proteins from bCLCA2 fragments that together span the length of the 90-kDa bCLCA2 proteins, bCLCA2 cDNA was cut with unique restriction enzymes: (i) GST-HX, HindIII and XhoI; (ii) GST-HV, HindIII and PvuII; (iii) GST-HP, HindIII and PstI; (iv) GST-NE, NdeI and EcoRV; (v) GST-VX, PvuII and XhoI; (vi) GST-PX, PstI and XhoI; and (vii) GST-BX, BstXI and XhoI. Blunt-ended restriction fragments were electrophoretically purified and ligated at either SmaI or blunted EcoRI sites to linearized pGEX-2T vector (Amersham Biosciences).

To construct the GST-$\beta_4$BM$_{hCLCA2(90)}$ (SEQ ID NO:48) (harboring the $\beta_4$-binding Motif of hCLCA2), PROTOMAT was used to search for conserved motifs in the 90- and 35-kDa subunits of hCLCA2. Identified sequences AFS-RISSGTG, (SEQ ID NO:50) located at amino acids 479-488 of the 90-kDa hCLCA2 subunit ($\beta_4$BM$_{hCLCA2(90)}$), and GFSRVSSGGS (SEQ ID NO:51), located at amino acids 730-739 of the 35-kDa hCLCA2 subunit ($\beta_4$BM$_{hCLCA2(35)}$; SEQ ID NO:49) both tagged at their C termini with hemagglutinin (HA), were generated by primer extension with Taq polymerase and inserted into the EcoRI and HindIII sites of pGEX-KG. ($\beta_4$BM$_{hCLCA2(35)}$ is SEQ ID NO:49).

The specific determining loop (SDL) sequences of the $\beta_4$ integrin subunit (amino acids 184-203) and the $\beta_1$ integrin subunit (amino acids 197-219), tagged at the C terminus with HA, were generated by PCR and inserted into the EcoRI and HindIII sites of pGEX-KG to generate $\beta_4$(184-203) and $\beta_1$(197-219) GST fusion constructs, respectively.

To generate $\beta_{(4-1-4)}$ chimeric integrin, amino acids 184-203 of the SDL of the $\beta_4$ I-domain were substituted for the corresponding sequence of the $\beta_1$ integrin (amino acids 197-219) by PCR using the unique restriction sites NdeI in the RcCMV vector backbone and BspMI in the $\beta_4$ cDNA with the high fidelity DNA polymerase Herculase (Stratagene, La Jolla, Calif.). The sequence of the chimeric integrin was verified.

EXAMPLE 12

This example describes the cell lines and transfection procedures used in Examples below. The MDA-MB-231L breast cancer cell line was from Dr. J. A. Price (The University of Texas M. D. Anderson Cancer Center, Houston, Tex.), 4T1 was from Dr. F. R. Miller (Karmanlos Cancer Institute, Detroit, Mich.), and human embryo kidney (HEK) 293 cells were from ATCC (Manassas, Va.). All cell lines were grown in Dulbecco's modified Eagle's medium supplemented with 10% heat-inactivated fetal bovine serum. HEK293 cells were transiently transfected with Myc-tagged hCLCA2, $\alpha_6$, $\alpha_6+\beta_4$, and $\alpha_6+\beta_{4-1-4}$, or vector alone using LipofectAMINE™ Plus as described by the manufacturer (Invitrogen). Transfection rates assessed by green fluorescent protein co-transfection were 40-50%. Cells were used in the various assays 48 h after transfection unless otherwise stated.

EXAMPLE 13

This Example demonstrates the purification of GST fusion proteins. GST-bCLCA2 fragments, GST-$\beta_4$(184-203)-HA, GST-$\beta_1$(197-219)-HA, GST-$\beta_4$BM$_{hCLCA2(90)}$-HA, and GST-$\beta_4$BM$_{hCLCA(35)}$-HA fusion proteins were purified according to the manufacturer's instructions (New England Biolabs, Beverly, Mass.). Briefly, 2 liters of *Escherichia coli* culture were centrifuged after a 2-h isopropyl-$\beta$-D-thiogalactoside induction (0.3 mM). Cell pellets were sonicated in 100 ml of column buffer (CB; 20 mM Tris-HCl, pH 7.4, 200 mM NaCl, 1 mM EDTA) and then centrifuged at 19,000 rpm (at 4° C. for 20 min). Supernatants were diluted 1:3 with CB and passed through a glutathione-agarose column. Columns were washed with 10 volumes of CB and eluted with 10 mM glutathione in CB. The purity of the elutes was evaluated by Coomassie Blue staining of SDS-polyacrylamide gels and Western blotting with $\alpha$-GST and/or $\alpha$-HA pAbs. Protein concentrations were measured by the Bradford method (Bio-Rad). Alternatively, HA-tagged GST fusion proteins were purified with $\alpha$-HA mAb-conjugated protein G-agarose beads. Control GST fusion proteins were P14 and PEDA derived from fibronectin (FN) III (14) (amino acids 2045-2062) and FNIII$_{EDA}$ (amino acids 1774-1791), respectively using procedures well known to those skilled in the art.

EXAMPLE 14

This Example demonstrates the purification of hCLCA2 and $\beta_4$ integrin. Myc-tagged hCLCA2 was immunopurified from transfected HEK393 cells 48 h after transfection, and the $\beta_4$ integrin was immunopurified from MDA-MB-231L cells as described previously using techniques well known to those skilled in the art. Cells were lysed in Tris-buffered saline (TBS) lysis buffer (50 mM Tris-HCl, pH 7.4, 150 mM NaCl, 1 mM phenylmethylsulfonyl fluoride, 0.01% aprotinin, 1 mM benzamidine, and 1% octyl-$\beta$-glucoside (OG)) (for 1 h at 4° C.), and lysates were centrifuged at 15,000 rpm (for 20 min at 4° C.) to remove insoluble materials. Precleared supernatants were mixed with $\alpha$-Myc mAb9E10 (hCLCA2) or $\alpha$-$\beta_4$ mAb3E1, respectively, and incubated for 4 h at 4° C. Protein G-Sepharose beads were then added to the reaction mixtures and incubated overnight at 4° C. Immune complexes were washed extensively with cold TBS lysis buffer (0.5% OG), and bound protein (hCLCA2 and $\beta_4$ integrin) was collected in 100 mM Tris-HCl, pH 8.0, containing 150 mM NaCl, 100 mM glycine, and 0.5% OG. The purity was determined by SDS-PAGE followed by silver staining and/or Western blotting with $\alpha$-Myc mAB9E1 0 or rabbit $\alpha$-$\beta_4$ pAbH101, respectively (4, 10). The 35-kDa subunit of hCLCA2 was purified from extracts of HEK293 cells that had been transfected with a double tagged hCLCA2 cDNA construct containing a Myc tag at its N terminus and an HA tag at its C terminus. The 35-kDa protein was purified by $\alpha$-HA immunoaffinity chromatography, while the 90-kDa hCLCA2 protein was purified by $\alpha$-Myc immunoaffinity chromatography from the flow-through of the $\alpha$-HA column.

EXAMPLE 15

This Example discloses methods for performing ELISA assays in the Examples below. An ELISA was used according to standard methods to measure the binding of GST-$\beta_4$BM$_{hCLCA2(90)}$-HA to the $\beta$ integrins $\beta_4$, $\beta_1$, and $\beta_3$. Wells of microtitration plates were coated with integrins, the control substrate fibronectin, or the blocking agent BSA (all at 10 μg/ml) overnight at 4° C. After blocking with 3% skim milk (for 2 h at room temperature) and several washes with phosphate-buffered saline, GST-$\beta_4$BM$_{hCLCA2(90)}$-HA was added at various concentrations and incubated for 1 h at room temperature. Bound GST-$\beta_4$BM$_{hCLCA2(90)}$-HA was determined colorimetrically using $\alpha$-HA mAbF-7, horseradish peroxidase-conjugated goat $\alpha$-mouse IgG antibody, and the horseradish peroxidase substrate o-phenylenediamine. For ELISA binding studies between GST-$\beta_4$BM$_{hCLCA2(90)}$-HA and GST-$\beta_4$-HA, GST-$\beta_4$-HA was biotinylated, and GST-$\beta_4$BM$_{hCLCA2(90)}$-HA-bound GST-$\beta_4$-HA was detected by streptavidin-horseradish peroxidase as described previously (37).

EXAMPLE 16

This Example discloses the methods of performing pull-down assays. Pull-down assays were performed according to standard methods known to those skilled in the art (i.e., Puzon-McLaughlin, W., and Takada, Y. (1996) J. Biol. Chem. 271, 20438-20443). In brief, immunopurified full-length $\beta_4$ integrin, GST-$\beta_4$(184-203)-HA, and GST-$\beta_1$(197-219) were immobilized on protein G-Sepharose beads conjugated with $\alpha$-$\beta_4$ pAb1922 or glutathione-conjugated agarose beads, respectively. Beads with bound $\beta_4$ or GST fusion proteins were washed extensively with lysis buffer containing 1 mM MnCl$_2$ and 0.5% OG (washing buffer) and then incubated overnight at 4° C. with cell lysates or immunopurified hCLCA2 from Myc-hCLCA2-transfected HEK293 cells, both in TBS lysis buffer containing 1 mM MnCl$_2$ at a final detergent concentration of 0.5% OG (4, 40). Conversely, beads conjugated with $\alpha$-Myc mAb9E10 and bound hCLCA2-Myc or glutathione-conjugated agarose beads with bound GST-$\beta_4$BM$_{hCLCA2(90)}$-HA or GST-$\beta_4$BM$_{hCLCA2(35)}$-HA were used to pull down the $\beta_4$ integrin from lysates of HEK293 cells co-transfected with the $\alpha_6$ and $\beta_4$ integrin subunits or surface-biotinylated MDA-MB-231 cells (both cell lysates were prepared in the same 0.5% OG-containing buffer as above). For detection of bound protein, beads were washed extensively with washing buffer and boiled in SDS sample buffer, and bound material was detected by SDS-PAGE and Western blotting.

EXAMPLE 17

This Example demonstrates fluorescence activated cell sorting (FACS) analyses and adhesion and lung colony assays. FACS analyses, adhesion assays, and lung colony assays were performed according to procedures well known to those skilled in the art. (See, i.e., Abdel-Ghany, et al. (2001) J. Biol. Chem. 276, 25438-25446; Cheng et al. (2003) J. Biol. Chem. 278, 24600-24607.) Briefly, tumor cell binding of GST-CLCA$_{(90)}$-$\beta_4$BM was determined by incubating MDA-MB-231 cells (or 4T1) in end-over-end culture with GST-$\beta_4$BM$_{hCLCA2(90)}$-HA for 20 min at room temperature in Dulbecco's modified Eagle's medium containing 1% BSA. After washing, tumor cells were stained with α-HA mAb (or mIgG as control) and subjected to FACS analysis. $\beta_4$/CLCA adhesion inhibition experiments were conducted with both hCLCA- and $\beta_4$-derived polypeptides. Human CLCA2-derived polypeptides (GST-$\beta_4$BM$_{hCLCA2(90)}$-HA and GST-$\beta_4$BM$_{hCLCA2(35)}$-HA) or control polypeptides (GST-P14-HA and GST-PEDA-HA) were preincubated with tumor cells for 20 min, and tumor cell adhesion to hCLCA2-coated dishes was performed in the presence or absence of polypeptide. $\beta_4$-derived polypeptides ($\beta_4$(184-203) (synthetic), GST-$\beta_4$(184-203)-HA, $\beta_1$(197-219) (synthetic), and GST-$\beta_1$(197-219)-HA (controls)) were incubated with hCLCA2-coated dishes for 30 min at 37° C., and tumor cell adhesion was determined in the presence or absence of polypeptide. Polypeptides were used at the indicated concentrations. Lung colony inhibition assays were performed with hCLCA2-derived polypeptides (GST-$\beta_4$BM$_{hCLBA2(90)}$-HA and GST-P14-HA (control) (37)). Tumor cells (1×10$^5$ cells/mouse) were incubated with hCLCA2 polypeptide (for 20 min at 37° C.) prior to intravenous injection together with polypeptide (0.5 mg/mouse). Female Scid/beige (MDA-MB-231) and BALB/c (4T1) 4-week-old mice were used (eight mice/experimental condition).

EXAMPLE 18

This Example demonstrates that CLCA proteins contain binding domains for $\beta_4$-expressing tumor cells. To identify the CLCA sequence that is responsible for the $\beta_4$/CLCA-mediated adhesion of lung-metastatic human (MDA-MB-231) and mouse (4T1) breast cancer cells, we first examined the binding behavior of the $\beta_4$/CLCA adhesion-blocking mAb6D3 using a series of polypeptides encompassing the length of the 90-kDa subunit of the CLCA prototype bCLCA2 (Lu-ECAM-1) (FIG. 15A). Polypeptides were prepared as GST fusion proteins in E. coli as described in Example 11, and the fusion proteins were purified as described in Example 13 on a glutathione column (FIG. 15B). Antibody 6D3 was able to bind and immunoprecipitate the fusion proteins GST-HX, GST-VX, GST-PX, and GST-BX but not GST-HV, GST-HP, and GST-NE (FIG. 15C). The shortest bCLCA2 fragment recognized by mAb6D3 was GST-BX, localizing the antibody-binding domain to the second extracellular domain of bCLCA2 (Elble et al. (1997) J. Biol. Chem. 272, 27853-27861). Next we examined whether the same bCLCA2 fragments that supported binding of the $\beta_4$/CLCA adhesion-blocking antibody also harbor the binding domain for $\beta_4$-expressing MDA-MB-231 cells. To do so, we coated wells of microtitration plates with GST-BX, GST-PX, GST-NE, and GST-HP and seeded coated wells with MDA-MB-231 cells. Analogous to the binding characteristics of the adhesion-blocking antibody, MDA-MB-231 bound to GST-PX and GST-BX but not to GST-HP and GST-NE (FIG. 15D). Binding of MDA-MB-231 to GST-PX and GST-BX was equally as strong as the adhesion to the 90-kDa natural processing product of bCLCA2. Unexpectedly, adhesion of MDA-MB-231 as well as mAb6D3 (data not shown) was not restricted to the 90-kDa protein but was also mediated by the 35-kDa subunit of bCLCA2 (FIG. 15D). Curious whether this adhesion behavior was specific for bCLCA2 or extended to other CLCA proteins, we tested the adhesion of the 90- and 35-kDa subunits of hCLCA2 for adhesion to MDA-MB-231 cells. Both products bound the cancer cells (FIG. 15D) but not mAb6D3, which is consistent with its specificity for bCLCA2 and mCLCA1. Identical binding data were also obtained for other lung-metastatic cancer cell lines including 4T1, B16-F10, and CSML-100 using the 90- and 35-kDa subunits of either bCLCA2 (Lu-ECAM-1) or hCLCA2 in static adhesion assays (data not shown).

EXAMPLE 19

The Example demonstrates identification of the $\beta_4$ Integrin-binding Motif of CLCAs. We examined whether the 90- and 35-kDa subunits of hCLCA2 (and bCLCA2) harbor a common binding motif for the $\beta_4$ integrin by using the PROTOMAT motif search program. The sequences AFS-RISSGTG (SEQ ID NO: 50) in the 90-kDa and GFS-RVSSGGS (SEQ ID NO: 51) in the 35-kDa subunits of hCLCA2 were identified as the single, common motif (FIG. 16A). The first sequence is located at amino acid residues 479-488 of hCLCA2, placing it within the GST-BX fragment of bCLCA2 (AFSRISSRSG) (SEQ ID NO: 50) recognized in Example 18 as the shortest bCLCA2 fragment to mediate binding of lung-metastatic cancer cells (FIG. 15D). The second sequence is located at amino acids 740-749 of hCLCA2 located near the N terminus of the 35-kDa hCLCA2. To prove that this motif is binding MDA-MB-231 cells via the $\beta_4$ integrin, we generated a HA-tagged GST fusion protein of the 90-kDa $\beta_4$-binding motif of hCLCA2 (termed $\beta_4$BM$_{hCLCA2(90)}$) as described in Example 11 and tested its binding ability for the $\beta_4$ integrin by ELISA as described in Example 15.

Figure 17A:
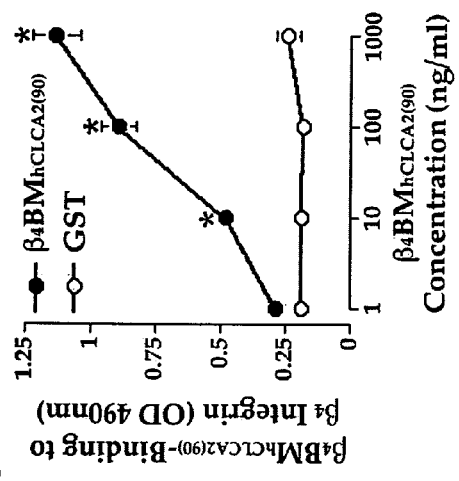
FIG. 17A is a graphical representation of results from an adhesion assay indicating $\beta_4BM_{hCLCA2(90)}$, but not GST, adheres to $\beta_4$ integrin-coated dishes (15 μg/ml) in a dose-dependent manner (assay medium: phosphate-buffered saline+1 mm MnCl$_2$).
Figure 17B:
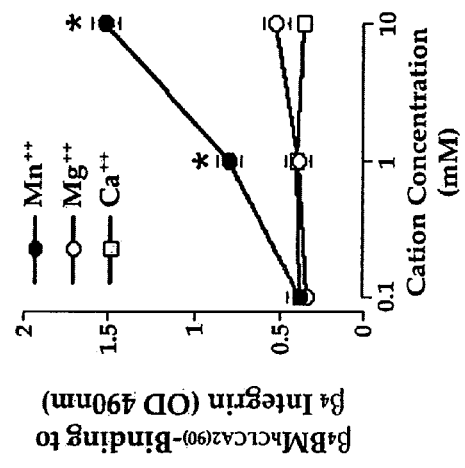
FIG. 17B is a graphical representation of results demonstrating Mn$^{2+}$, but not Mg$^{2+}$ and Ca$^{2+}$, promotes adhesion of $\beta_4BM_{hCLCA2(90)}$ (50 ng/ml) to $\beta_4$ integrin (15 μg/ml). *, p<0.01 relative to GST control.

$\beta_4$BM$_{hCLCA2(90)}$ bound to immobilized $\beta_4$ integrin but not to $\beta_1$ integrin, $\beta_3$ integrin, fibronectin, or BSA. The same result (FIG. 16B) was achieved in the pull-down assays performed as described in Example 16. Immobilized on glutathione-conjugated agarose beads, $\beta_4$BM$_{hCLCA2(90)}$ pulled down $\beta_4$ but not $\beta_1$ and $\beta_3$ from solutes (FIG. 16C), and, in reverse, $\beta_4$ integrin but not $\beta_1$ integrin, immobilized by anti-integrin antibodies on protein G-conjugated agarose beads, pulled down soluble $\beta_4$BM$_{hCLCA2(90)}$ (FIG. 16D). Identical results were obtained with the 35-kDa $\beta_4$-binding motif of hCLCA2 (termed $\beta_4$BM$_{hCLCA2(35)}$) (data not shown). To test whether the adhesion of $\beta_4$BM$_{hCLCA2(90)}$ to $\beta_4$ integrin was dose-dependent, we coated wells of microtitration plates with a standard concentration of immunopurified $\beta_4$ integrin (10 µg/ml) and determined the adhesion of increasing concentrations of $\beta_4$BM$_{hCLCA2(90)}$ by ELISA. Our data showed a linear increase in adhesion of $\beta_4$BM$_{hCLCA2(90)}$ from 1 to 1,000 ng (FIG. 17A). This adhesion was dependent upon the presence of Mn$^{2+}$, but not Mg$^{2+}$ or Ca$^{2+}$, in the assay medium (FIG. 17B).

EXAMPLE 20

This Example demonstrates that $\beta_4BM_{hCLCA2(90)}$ binds to lung-metastatic cancer cells and inhibits adhesion to cells expressing hCLCA2. To establish hCLCA290-$\beta_4$BM as a $\beta_4$/hCLCA2 adhesion-blocking polypeptide, we first examined the ability of the polypeptide to bind to the surface of lung-metastatic MDA-MB-231 cancer cells as described in Example 17 and as follows. $\beta_4BM_{hCLCA2(90)}$ was incubated with tumor cells for 20 min at room temperature, and bound polypeptide was detected by $\alpha$-GST antibody and quantified by FACS analysis. Data showed strong binding of $\beta_4BM_{hCLCA2(90)}$ to tumor cell surfaces, while the control polypeptide P14 did not adhere (FIG. 18A, a). The FACS histogram generated by bound $\beta_4BM_{hCLCA2(90)}$ was similar to that generated by $\alpha$-$\beta_4$ antibody staining of MDA-MB-231 cells (FIG. 18A, b), concurring with the interaction between $\beta_4BM_{hCLCA2(90)}$ and the $\beta_4$ integrin. In accordance, $\beta_4BM_{hCLCA2(90)}$ as well as $\beta_4BM_{hCLCA2(35)}$ immobilized on the well bottom of microtitration plates supported adhesion of MDA-MB-231 cancer cells to the same extent as full-length, immunopurified hCLCA2, while BSA and GST did not support tumor cell adhesion (FIG. 18B). Finally $\beta_4BM_{hCLCA2(90)}$ and $\beta_4BM_{hCLCA2(35)}$ were tested for their abilities to block the adhesion of lung-metastatic MDA-MB-231 cells to hCLCA2-coated wells in vitro. Both $\beta_4BM_{hCLCA2(90)}$ and $\beta_4BM_{hCLCA2(35)}$, preincubated with hCLCA2-coated wells for 20 min at room temperature, completely blocked the adhesion of MDA-MB-231 cells to hCLCA2 (FIG. 18C). The control polypeptides P14 and PEDA were unable to block tumor cell adhesion to hCLCA2. Identical results were obtained for lung-metastatic 4T1 murine breast cancer cells (data not shown).

EXAMPLE 21

Figure 19A:
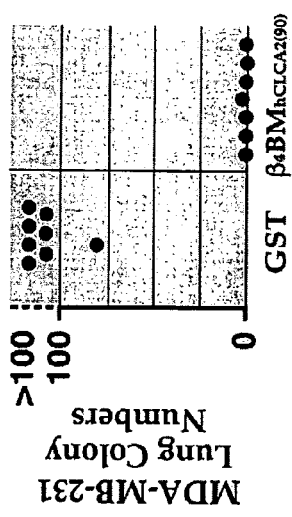
FIG. 19A is a graphical representation of MDA-MB-231 lung colony numbers. MDA-MB-231 breast cancer cells incubated for 20 min with $\beta_4BM_{hCLCA2(90)}$ or GST were injected into the lateral tail vein of 4-week-old, female Scid/beige mice (1×10$^5$ tumor cells/300 μg of $\beta_4BM_{hCLCA2(90)}$/0.2 ml of Dulbecco's modified Eagle's medium/mouse). A total of eight mice (2×4) per test condition were injected. Mice were sacrificed 8 weeks later, and lung colonies were counted and tabulated.
Figure 19B:
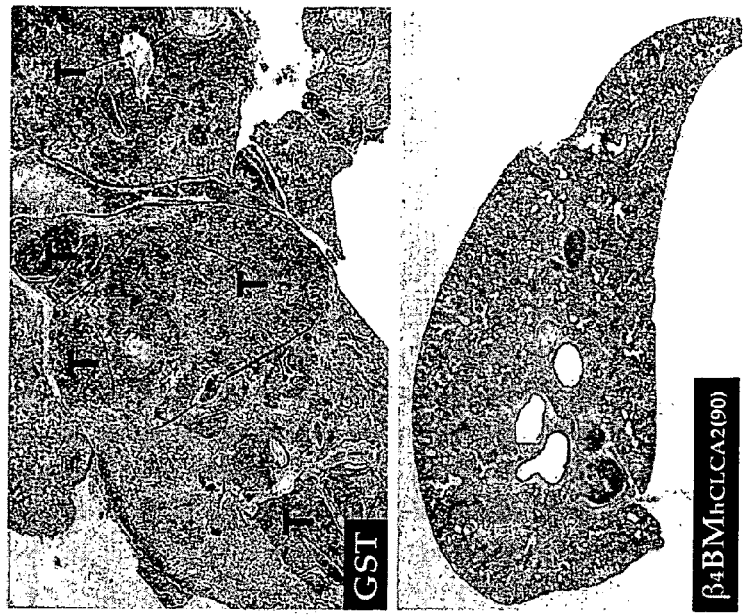
FIG. 19B is a representation of gross and histological views of the lungs of test animals showing multiple tumor colonies in mice injected with GST and normal tumor-free lungs in mice injected with $\beta_4BM_{hCLCA2(90)}$. T, tumor.

This Example demonstrates that $\beta_4BM_{hCLCA2(90)}$ blocks lung colonization of MDA-MB-231 cells in vivo. To examine the effect of the $\beta_4BM_{hCLCA2(90)}$-GST fusion protein on lung colonization of MDA-MB-231 cells, we incubated MDA-MB-231 cells for 20 min with $\beta_4BM_{hCLCA2(90)}$ and then injected tumor cells together with the fusion protein into the lateral tail vein of 4-week-old, female Scid/beige mice ($2\times10^5$ tumor cells/300 µg of $\beta_4BM_{hCLCA2(90)}$/0.2 ml of Dulbecco's modified Eagle's medium/mouse). Control mice received tumor cells preincubated with GST administered at the same dose. Eight weeks later, animals in the control group exhibited signs of respiratory distress, and the experiment was terminated. Autopsy and lung colony counting revealed a median number of >100 (from 77 to >100) tumor colonies in the control group and zero (from 0 to 2) colonies in the $\beta_4BM_{hCLCA2(90)}$-treated animal group (FIG. 19A). Gross examination of the lungs showed numerous tumor nodules throughout the lungs as well as in mediastinal and bronchial lymph nodes in GST-treated mice and normal, tumor-free lung in seven of eight $\beta_4BM_{hCLCA2(90)}$-treated mice. Histological examination of the lungs confirmed the gross findings. There was massive tumor involvement in the lungs of GST-treated mice but no evidence of metastatic disease in seven of eight $\beta_4BM_{hCLCA2(90)}$-treated mice. The remaining $\beta_4BM_{hCLCA2(90)}$-treated mouse had two small lung colonies. This outcome was not the result of diminished growth and survival rates of tumor cells exposed to $\beta_4BM_{hCLCA2(90)}$ polypeptide (data not shown).

EXAMPLE 22

This Example demonstrates the determination that the specific determining loop of the $\beta_4$ integrin harbors the a domain to which the CLCA $\beta_4$ binding domain binds. To identify the $\beta_4$ sequence that interacted with hCLCA2, we generated a GST-$\beta_4$(184-203)-HA fusion protein (GST-$\beta_4$ for short) that corresponded to a predicted loop of the $\beta_1$ and $\beta_3$ integrins shown to be involved in ligand binding (FIG. 20A). This sequence comprises the N-terminal two-thirds of the SDL region of the $\beta_4$ integrin subunit. The corresponding sequence of the $\beta_1$ integrin was used to prepare a control GST fusion protein (GST-$\beta_1$(197-219)-HA (GST-$\beta_1$ for short)). These fusion proteins were tested first for their ability to bind hCLCA2 in a modified ELISA. Wells of microtitration plates were coated with GST-$\beta_4$, GST-$\beta_1$, or GST (all at 10 µg/ml), and coated wells were probed for hCLCA2 adhesion. Human CLCA2 adhesion to GST-$\beta_4$-coated wells was more pronounced than the binding of hCLCA2 to high protein-binding plastic, while GST-$\beta_1$- and GST-coated wells did not support hCLCA2 binding (FIG. 20B). These binding data were confirmed in pull-down assays in which GST-$\beta_4$ and GST-$\beta_1$ bound to glutathione-agarose beads were tested for their abilities to pull down hCLCA2 from lysates of hCLCA2-Myc-transfected HEK293 cells. Only GST-$\beta_4$ but not GST-$\beta_1$ was able to pull down hCLCA2 (FIG. 20C). To examine whether GST-$\beta_4$ and $\beta_4BM_{hCLCA2(90)}$ were the interacting binding domains of the $\beta_4$ integrin subunit and hCLCA2, microtitration plates were coated with skim milk (blocking agent), $\beta_4BM_{hCLCA2(90)}$, or the control polypeptide PEDA. Biotinylated GST-$\beta_4$ selectively bound to $\beta_4BM_{hCLCA2(90)}$ but not to PEDA (FIG. 20D). GST-$\beta_1$ did not bind to any of the three substrates (data not shown). Similarly the chimeric $\beta_4$ protein $\beta_{4-1-4}$ in which the C-terminal two-thirds of the $\beta_4$ SDL domain were replaced with the corresponding region of the $\beta_1$ integrin subunit failed to bind to hCLCA2 (FIG. 20E). Finally synthetic peptides of $\beta_4$(184-203) and $\beta_1$(207-213) were evaluated for their ability to block the adhesion of MDA-MB-231 and 4T1 breast cancer cells to hCLCA2 and mCLCA1, respectively. Adhesion assays were performed as described in Example 17. (See also, Abdel-Ghany et al., (2001) J. Biol. Chem. 276, 25438-25446; Tsuruta, et al. (2003) J. Biol. Chem. 278, 38707-38714). In brief, wells of microtitration plates were coated with substrate (hCLCA2 (FIG. 21A), mCLCA1 (FIG. 21D), EHS laminin (FIG. 21C and FIG. 21E), or placental laminin (FIG. 21B)) overnight at 4° C. at the indicated concentration, then seeded with MDA-MB-231 (FIG. 21A, FIG. 21B, and FIG. 21C) or 4T1 (FIG. 21D and FIG. 21E) breast cancer cells, and incubated for 20 min at 37° C. The number of bound tumor cells was determined by a standard colorimetric method. Polypeptide $\beta_4$(184-203) and $\beta_1$(197-219) were added to substrate-coated wells and incubated for 30 min at room temperature. Polypeptides were either removed by washing prior to the addition of tumor cells (adhesion blocking) or were present throughout the tumor cell adhesion assay (adhesion competition). A complete inhibition of adhesion (by blocking or competition) was observed for both MDA-MB-231 and 4T1 cells with the $\beta_4$ polypeptide but not the $\beta_1$ polypeptide. Thus, the $\beta_4$ polypeptide, but not the $\beta_1$ polypeptide, blocked adhesion of both MDA-MB-231 and 4T1 cells to the respective human and mouse CLCA proteins (FIG. 21, A and D). Polypeptides were equally efficient in their inhibitory activities when they were preincubated with CLCA-coated wells prior to seeding of tumor cells or when they were present throughout the adhesion assay. Polypeptides had no effect on the binding of tumor cells to placental (FIG. 21B) and EHS (FIG. 21, C and E) laminins.

EXAMPLE 23

This Example demonstrates that the 90-kda protein of hCLCA1 harbors a disrupted β₄BM and fails to bind β₄ integrin. In contrast to the highly conserved β₄BMs of the 90-kDa subunits of hCLCA2, mCLCA5, mCLCA1, and bCLCA2, the hCLCA1 90-kDa hCLCA1 protein exhibited a disrupted β₄BM (see underlined deviations from hCLCA2 FIG. 22A). However, hCLCA1 contains a relatively well conserved β₄BM motif (CFSRTSSGGS) (SEQ ID NO:52) in its 35-kDa processing product (SEQ ID NO:53) (FIG. 22A). Thus, β₄ integrin should not be able to bind to the 90-kDa hCLCA1 protein but might bind to the unprocessed 125-kDa and the processed 35-kDa proteins of hCLCA1. To examine this premise, we tested the binding of the 90-kDa fragment with that of the full-length, unprocessed hCLCA1 prepared from Myc-hCLCA1-transfected HEK293 cells for β₄ binding and MDA-MB-231 adhesion (FIG. 22B and FIG. 22C). We transfected HEK293 cells with Myc-tagged hCLCA1 and purified the protein by -Myc immunoaffinity chromatography. Four fractions were collected from the affinity column. Fractions 1 and 4 contained only the 90-kDa processing product, while fractions 2 and 3 contained the 90-kDa processing product as well as the 125-kDa full-length, unprocessed hCLCA1 (the untagged 35-kDa hCLCA1 was lost in the column flow-through) (FIG. 22B). To test these fractions for adhesion of MDA-MB-231 cells, wells of microtitration plates were coated with the four fractions, then seeded, and incubated for 20 min with MDA-MB-231 cells. Tumor cells strongly bound to fractions 2 and 3 but failed to bind to fractions 1 and 4, indicating that they did not recognize the disrupted "β₄BM" sequence but recognized the sequence of the conserved β₄BM in the 35-kDa fragment of full-length hCLCA1 protein (FIG. 22C). A pull-down assay using GST-4 immobilized on glutathione-agarose beads confirmed these data showing the inability of β₄ to pull down the 90-kDa hCLCA1 but an excellent pull-down of the 90-kDa hCLCA2 (FIG. 22D).

Having described the preferred embodiments of the present invention, it will be apparent to one of ordinary skill in the art that various modifications may be made to the disclosed embodiments, and that such modifications are intended to be within the scope of the present invention.

---

We claim:

1. An isolated and purified polypeptide which is a 90 kDa fragment of SEQ ID NO: 32, wherein said fragment comprises the amino acid sequence of SEQ ID NO: 61 and binds to B4 integrin.

2. The polypeptide of claim 1, wherein the fragment has the sequence of SEQ ID NO: 48.

3. An isolated and purified polypeptide which is a 35 kDa fragment of SEQ ID NO: 32, wherein said fragment comprises the amino acid sequence of SEQ ID NO: 651 and binds to B4 integrin.

4. The polypeptide of claim 3, wherein the fragment has the sequence of SEQ ID NO: 49.

5. An isolated peptide of 10 amino acids comprising SEQ ID NO:61.

6. The peptide of claim 5 wherein the peptide sequence is selected from the group consisting of SEQ ID NO:50, SEQ ID NO:51 and SEQ ID NO:52.

* * * * *

SEQUENCE LISTING

```
<160> NUMBER OF SEQ ID NOS: 63

<210> SEQ ID NO 1
<211> LENGTH: 3317
<212> TYPE: DNA
<213> ORGANISM: Unknown
<220> FEATURE:
<223> OTHER INFORMATION: sequence encoding Lu-ECAM-1 and Lu-ECAM-1
      associated protein from bovine endothelial cells

<400> SEQUENCE: 1
ggattccagg gtctccagca ttgcctgaat ctggatgtag gtttactgta              50
acatgtgcaa aa atg gtg ctc tgt ctg aat gtt att ctg ttc cta act       98 ttg cat ctc ttg cct gga atg aaa agt tca atg gta aat ttg att       143 aac aat ggg tat gat ggc att gtc att gca att aac ccc agt gtg       188 cca gaa gat gaa aaa ctc att gaa aac ata aag gaa atg gta act       233 gaa gct tct act tac ctg ttt cat gcc acc aaa cga aga gtt tat       278 ttc agg aat gtg agc att tta att cca atg acc tgg aaa tca aaa       323 tct gag tac ttc ata cca aaa caa gaa tca tat gac cag gca gat       368 gtc ata gtt gct aat ccc tat cta aaa tat gga gat gat ccc tat       413 aca ctt caa tat gga agg tgt gga gaa aaa gga aaa tat ata cat       458 ttt act cca aac ttc ttg ttg act aat aat ttc cac atc tat ggg       503 tcc cga ggc aga gta ttt gtc cat gag tgg gcc cat ctc cgc tgg       548 gga ata ttt gat gag tat aat gtg gac cag cca ttc tat att tcc       593 aga aag aac act att gaa gca aca aga tgt tca act cat att act       638 ggt att aat gtg gtt ttc aag aaa tgc cct gga ggc agc tgt ata       683 aca agt cta tgc aga cgt gac tca cag aca ggg ctg tat gaa gca       728
```

-continued

| | |
|---|---|
| aaa tgt aca ttc ctt cca aaa aaa tcc cag act gca aag gaa tcc | 773 |
| att atg ttt atg cca agt ctc cat tct gtg act gaa ttt tgt aca | 818 |
| gaa aaa aca cac aat aca gaa gct cca aac cta caa aac aaa atg | 863 |
| tgc aat ggc aaa agc aca tgg gat gta atc atg aac tct gtt gac | 908 |
| ttt cag aat aca tct ccc atg aca gaa atg aat cca ccg act cat | 953 |
| cct aca ttt tca ttg ctc aag tcc aaa cag cgg gta gtc tgt ttg | 998 |
| gta ctt gat aaa tct gga agc atg tct gca gaa gac cgt ctc ttt | 1043 |
| caa atg aat caa gca gca gaa cta tac ttg att caa gtt att gaa | 1088 |
| aag gga tct tta gtt ggg atg gtt aca ttt gac agt gtt gct gaa | 1133 |
| atc caa aat cat cta aca aga ata act gat gat aat gtt tac caa | 1178 |
| aag atc acc gca aaa ctg cct caa gta gct aat ggt gga act tca | 1223 |
| att tgt aga ggg ctc aaa gca gga ttc cag gca att atc cac agt | 1268 |
| gac cag agt act tct ggt tct gaa atc ata cta tta act gat ggg | 1313 |
| gaa gat aat gaa ata aat tca tgc ttt gag gat gta aaa cga agt | 1358 |
| ggt gca atc atc cac acc att gct ctg gga ccc tct gct gcc aaa | 1403 |
| gaa ctg gag aca ttg tca aat atg aca gga gga tat cgt ttt ttt | 1448 |
| gcc aat aaa gac ata act ggc ctt act aat gct ttc agt aga att | 1493 |
| tca tct aga agt gga agc atc act cag cag gct att cag ttg gaa | 1538 |
| agc aaa gcc ttg aaa att aca gga agg aaa aga gta aac ggc aca | 1583 |
| gtg cct gta gac agt aca gtt gga aat gac act ttc ttt gtt gtc | 1628 |
| aca tgg aca ata caa aaa cca gaa att gtt ctc caa gat cca aaa | 1673 |
| gga aag aaa tat aaa acc tcg gat ttc aaa gaa gat aag tta aat | 1718 |
| att cga tct gct cgt ctg caa ata cct ggt att gca gag aca ggt | 1763 |
| act tgg act tac agc ctt cta aat aat cat gcc agc tct caa atg | 1808 |
| cta aca gtg aca gtg acc act cga gca aga agt cct act ata ccc | 1853 |
| cca gta att gca aca gct cac atg agt caa cat aca gca cat tat | 1898 |
| cct agc cca atg att gtt tat gca caa gtc agt caa ggg ttt ttg | 1943 |
| cct gta ctg gga atc agt gta ata gcc att ata gaa acc gaa gat | 1988 |
| gga cat caa gta aca ttg gag ctc tgg gac aat ggt gca ggt cgt | 2033 |
| gat act gtc aag aat gat ggc atc tac tca aga tac ttt aca gat | 2078 |
| tac tat gga aat ggt aga tac agt tta aaa gta cat gca cag gca | 2123 |
| aga aac aac acg gct agg cta aat tta aga caa cca cag aac aaa | 2168 |
| gtt cta tat gtt cca ggc tac gtt gaa aac ggt aaa att ata ctg | 2213 |
| aac cca ccc aga cct gaa gtc aaa gat gac ctg gca aaa gct aaa | 2258 |
| ata gaa gac ttt agc aga cta acc tct gga ggg tca ttt act gta | 2303 |
| tca gga gct cct cct cct ggt aat cac cct tct gtg ttc cca ccc | 2348 |
| agt aaa att aca gat ctt gag gct aag ttc aaa gaa gat tat att | 2393 |
| caa ctt tca tgg aca gcc cct ggc aat gtc cta gat aaa gga aaa | 2438 |
| gcc aac agc tac att ata aga ata agt aag agt ttc atg gat cgt | 2483 |
| caa gaa gat ttt gac aat gcg act tta gtg aat act tct aat cta | 2528 |

-continued

| | |
|---|---|
| ata cct aag gag gcc gga tca aaa gaa aat ttt gaa ttt aag cca | 2573 |
| gaa cat ttt aga gta gaa aat ggc acc aaa ttc tat att tca gtc | 2618 |
| caa gcc atc aac gaa gcc aat ctc atc tca gag gtt tct cac att | 2663 |
| gta caa gca atc aaa ttt att cct cta cca gaa gac agt gtc cat | 2708 |
| gat ctg ggt acc aag att tct gaa atc act ctg gca att tta gga | 2753 |
| tta cca atg att ttc tct gta ttt taaactagga attgtgtcag | 2797 |
| cactgataac caatgttata catagttggt acacatttat ttaggattta | 2847 |
| attcgctatt ttcttgttct tcagtagcta aattgtgtcc aaccttgcga | 2897 |
| ctgcaggact gcagcatgcc aggtttccct gtccatcacc aactcccaga | 2947 |
| gcttgctcaa atccatgttc atttgagtca gtaatgctaa ctatctcatc | 2997 |
| ctctactgcc ctcttctctg tttaccttca atctttcccc agcattagga | 3047 |
| tcttttccaa tgagtcagct cttagcatcg ggtggccaaa atattggcat | 3097 |
| tttcagcaac agttcttcaa atgaaatatc cagggtgatt tctcttagga | 3147 |
| tagactggtg actgacagtt caagggacac tctggagtct tctccagcac | 3197 |
| cgcaccgcag tttgaaagaa ccagttcttt ggtactcagc cttctttata | 3247 |
| gtccaatgct cacatctatc atgactcctg gaaaaaccat agctttgaga | 3297 |
| aatggatctt tgttgggaaa | 3317 |

<210> SEQ ID NO 2
<211> LENGTH: 905
<212> TYPE: PRT
<213> ORGANISM: Unknown
<220> FEATURE:
<223> OTHER INFORMATION: Lu-ECAM-1 precursor from bovine endothelial
     cells

<400> SEQUENCE: 2

```
Met Val Leu Cys Leu Asn Val Ile Leu Phe Leu Thr Leu His Leu
    -20             -15             -10

Leu Pro Gly Met Lys Ser Ser Met Val Asn Leu Ile Asn Asn Gly
    -5               1              5

Tyr Asp Gly Ile Val Ile Ala Ile Asn Pro Ser Val Pro Glu Asp
10              15              20

Glu Lys Leu Ile Glu Asn Ile Lys Glu Met Val Thr Glu Ala Ser
25              30              35

Thr Tyr Leu Phe His Ala Thr Lys Arg Arg Val Tyr Phe Arg Asn
40              45              50

Val Ser Ile Leu Ile Pro Met Thr Trp Lys Ser Lys Ser Glu Tyr
55              60              65

Phe Ile Pro Lys Gln Glu Ser Tyr Asp Gln Ala Asp Val Ile Val
70              75              80

Ala Asn Pro Tyr Leu Lys Tyr Gly Asp Asp Pro Tyr Thr Leu Gln
85              90              95

Tyr Gly Arg Cys Gly Glu Lys Gly Lys Tyr Ile His Phe Thr Pro
100             105             110

Asn Phe Leu Leu Thr Asn Asn Phe His Ile Tyr Gly Ser Arg Gly
115             120             125

Arg Val Phe Val His Glu Trp Ala His Leu Arg Trp Gly Ile Phe
130             135             140
```

-continued

```
Asp Glu Tyr Asn Val Asp Gln Pro Phe Tyr Ile Ser Arg Lys Asn
145                 150                 155

Thr Ile Glu Ala Thr Arg Cys Ser Thr His Ile Thr Gly Ile Asn
160                 165                 170

Val Val Phe Lys Lys Cys Pro Gly Gly Ser Cys Ile Thr Ser Leu
175                 180                 185

Cys Arg Arg Asp Ser Gln Thr Gly Leu Tyr Glu Ala Lys Cys Thr
190                 195                 200

Phe Leu Pro Lys Lys Ser Gln Thr Ala Lys Glu Ser Ile Met Phe
205                 210                 215

Met Pro Ser Leu His Ser Val Thr Glu Phe Cys Thr Glu Lys Thr
220                 225                 230

His Asn Thr Glu Ala Pro Asn Leu Gln Asn Lys Met Cys Asn Gly
235                 240                 245

Lys Ser Thr Trp Asp Val Ile Met Asn Ser Val Asp Phe Gln Asn
250                 255                 260

Thr Ser Pro Met Thr Glu Met Asn Pro Pro Thr His Pro Thr Phe
265                 270                 275

Ser Leu Leu Lys Ser Lys Gln Arg Val Val Cys Leu Val Leu Asp
280                 285                 290

Lys Ser Gly Ser Met Ser Ala Glu Asp Arg Leu Phe Gln Met Asn
295                 300                 305

Gln Ala Ala Glu Leu Tyr Leu Ile Gln Val Ile Glu Lys Gly Ser
310                 315                 320

Leu Val Gly Met Val Thr Phe Asp Ser Val Ala Glu Ile Gln Asn
325                 330                 335

His Leu Thr Arg Ile Thr Asp Asp Asn Val Tyr Gln Lys Ile Thr
340                 345                 350

Ala Lys Leu Pro Gln Val Ala Asn Gly Gly Thr Ser Ile Cys Arg
355                 360                 365

Gly Leu Lys Ala Gly Phe Gln Ala Ile Ile His Ser Asp Gln Ser
370                 375                 380

Thr Ser Gly Ser Glu Ile Ile Leu Leu Thr Asp Gly Glu Asp Asn
385                 390                 395

Glu Ile Asn Ser Cys Phe Glu Asp Val Lys Arg Ser Gly Ala Ile
400                 405                 410

Ile His Thr Ile Ala Leu Gly Pro Ser Ala Ala Lys Glu Leu Glu
415                 420                 425

Thr Lys Ser Asn Met Thr Gly Gly Tyr Arg Phe Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
460                 465                 470

Leu Lys Ile Thr Gly Arg Lys Arg Val Asn Gly Thr Val Pro Val
475                 480                 485

Asp Ser Thr Val Gly Asn Asp Thr Phe Phe Val Val Thr Trp Thr
490                 495                 500

Ile Gln Lys Pro Glu Ile Val Leu Gln Asp Pro Lys Gly Lys Lys
505                 510                 515

Tyr Lys Thr Ser Asp Phe Lys Glu Asp Lys Leu Asn Ile Arg Ser
520                 525                 530

Ala Arg Leu Gln Ile Pro Gly Ile Ala Glu Thr Gly Thr Trp Thr
```

```
                     535                 540                 545

Tyr Ser Leu Leu Asn His Ala Ser Ser Gln Met Leu Thr Val
550                 555                 560

Thr Val Thr Thr Arg Ala Arg Ser Pro Thr Ile Pro Pro Val Ile
565                 570                 575

Ala Thr Ala His Met Ser Gln His Thr Ala His Tyr Pro Ser Pro
580                 585                 590

Met Ile Val Tyr Ala Gln Val Ser Gln Gly Phe Leu Pro Val Leu
595                 600                 605

Gly Ile Ser Val Ile Ala Ile Ile Glu Thr Glu Asp Gly His Gln
610                 615                 620

Val Thr Leu Glu Leu Trp Asp Asn Gly Ala Gly Arg Asp Thr Val
625                 630                 635

Lys Asn Asp Gly Ile Tyr Ser Arg Tyr Phe Thr Asp Tyr Tyr Gly
640                 645                 650

Asn Gly Arg Tyr Ser Leu Lys Val His Ala Gln Ala Arg Asn Asn
655                 660                 665

Thr Ala Arg Leu Asn Leu Arg Gln Pro Gln Asn Lys Val Leu Tyr
670                 675                 680

Val Pro Gly Tyr Val Glu Asn Gly Lys Ile Ile Leu Asn Pro Pro
685                 690                 695

Arg Pro Glu Val Lys Asp Asp Leu Ala Lys Ala Lys Ile Glu Asp
700                 705                 710

Phe Ser Arg Leu Thr Ser Gly Gly Ser Phe Thr Val Ser Gly Ala
715                 720                 725

Pro Pro Gly Asn His Pro Ser Val Phe Pro Ser Lys Ile
730                 735                 740

Thr Asp Leu Glu Ala Lys Phe Lys Glu Asp Tyr Ile Gln Leu Ser
745                 750                 755

Trp Thr Ala Pro Gly Asn Val Leu Asp Lys Gly Lys Ala Asn Ser
760                 765                 770

Tyr Ile Ile Arg Ile Ser Lys Ser Phe Met Asp Arg Gln Glu Asp
775                 780                 785

Phe Asp Asn Ala Thr Leu Val Asn Thr Ser Asn Leu Ile Pro Lys
790                 795                 800

Glu Ala Gly Ser Lys Glu Asn Phe Glu Phe Lys Pro Glu His Phe
805                 810                 815

Arg Val Glu Asn Gly Thr Lys Phe Tyr Ile Ser Val Gln Ala Ile
820                 825                 830

Asn Glu Ala Asn Leu Ile Ser Glu Val Ser His Ile Val Gln Ala
835                 840                 845

Ile Lys Phe Ile Pro Leu Pro Glu Asp Ser Val His Asp Leu Gly
850                 855                 860

Thr Lys Ile Ser Glu Ile Thr Leu Ala Ile Leu Gly Leu Pro Met
865                 870                 875

Ile Phe Ser Val Phe
880             884

<210> SEQ ID NO 3
<211> LENGTH: 203
<212> TYPE: PRT
<213> ORGANISM: Unknown
<220> FEATURE:
<223> OTHER INFORMATION: Lu-ECAM-1 associated protein from bovine
      endothelial cells
```

<400> SEQUENCE: 3

| Val | Leu | Tyr | Val | Pro | Gly | Tyr | Val | Glu | Asn | Gly | Lys | Ile | Ile | Leu |
|---|---|---|---|---|---|---|---|---|---|---|---|---|---|---|
| 1 | | | | 5 | | | | | 10 | | | | | 15 |

| Asn | Pro | Pro | Arg | Pro | Glu | Val | Lys | Asp | Asp | Leu | Ala | Lys | Ala | Lys |
|---|---|---|---|---|---|---|---|---|---|---|---|---|---|---|
| | | | | 20 | | | | | 25 | | | | | 30 |

| Ile | Glu | Asp | Phe | Ser | Arg | Leu | Thr | Ser | Gly | Gly | Ser | Phe | Thr | Val |
|---|---|---|---|---|---|---|---|---|---|---|---|---|---|---|
| | | | | 35 | | | | | 40 | | | | | 45 |

| Ser | Gly | Ala | Pro | Pro | Pro | Gly | Asn | His | Pro | Ser | Val | Phe | Pro | Pro |
|---|---|---|---|---|---|---|---|---|---|---|---|---|---|---|
| | | | | 50 | | | | | 55 | | | | | 60 |

| Ser | Lys | Ile | Thr | Asp | Leu | Glu | Ala | Lys | Phe | Lys | Glu | Asp | Tyr | Ile |
|---|---|---|---|---|---|---|---|---|---|---|---|---|---|---|
| | | | | 65 | | | | | 70 | | | | | 75 |

| Gln | Leu | Ser | Trp | Thr | Ala | Pro | Gly | Asn | Val | Leu | Asp | Lys | Gly | Lys |
|---|---|---|---|---|---|---|---|---|---|---|---|---|---|---|
| | | | | 80 | | | | | 85 | | | | | 90 |

| Ala | Asn | Ser | Tyr | Ile | Ile | Arg | Ile | Ser | Lys | Ser | Phe | Met | Asp | Arg |
|---|---|---|---|---|---|---|---|---|---|---|---|---|---|---|
| | | | | 95 | | | | | 100 | | | | | 105 |

| Gln | Glu | Asp | Phe | Asp | Asn | Ala | Thr | Leu | Val | Asn | Thr | Ser | Asn | Leu |
|---|---|---|---|---|---|---|---|---|---|---|---|---|---|---|
| | | | | 110 | | | | | 115 | | | | | 120 |

| Ile | Pro | Lys | Glu | Ala | Gly | Ser | Lys | Glu | Asn | Phe | Glu | Phe | Lys | Pro |
|---|---|---|---|---|---|---|---|---|---|---|---|---|---|---|
| | | | | 125 | | | | | 130 | | | | | 135 |

| Glu | His | Phe | Arg | Val | Glu | Asn | Gly | Thr | Lys | Phe | Tyr | Ile | Ser | Val |
|---|---|---|---|---|---|---|---|---|---|---|---|---|---|---|
| | | | | 140 | | | | | 145 | | | | | 150 |

| Gln | Ala | Ile | Asn | Glu | Ala | Asn | Leu | Ile | Ser | Glu | Val | Ser | His | Ile |
|---|---|---|---|---|---|---|---|---|---|---|---|---|---|---|
| | | | | 155 | | | | | 160 | | | | | 165 |

| Val | Gln | Ala | Ile | Lys | Phe | Ile | Pro | Leu | Pro | Glu | Asp | Ser | Val | His |
|---|---|---|---|---|---|---|---|---|---|---|---|---|---|---|
| | | | | 170 | | | | | 175 | | | | | 180 |

| Asp | Leu | Gly | Thr | Lys | Ile | Ser | Glu | Ile | Thr | Leu | Ala | Ile | Leu | Gly |
|---|---|---|---|---|---|---|---|---|---|---|---|---|---|---|
| | | | | 185 | | | | | 190 | | | | | 195 |

| Leu | Pro | Met | Ile | Phe | Ser | Val | Phe |
|---|---|---|---|---|---|---|---|
| | | | | 200 | | | 203 |

```
<210> SEQ ID NO 4
<211> LENGTH: 26
<212> TYPE: DNA
<213> ORGANISM: Artificial sequence
<220> FEATURE:
<223> OTHER INFORMATION: Amplification primer

<400> SEQUENCE: 4
aatttaagcc agaacatttt agagta                                          26

<210> SEQ ID NO 5
<211> LENGTH: 23
<212> TYPE: DNA
<213> ORGANISM: Artificial sequence
<220> FEATURE:
<223> OTHER INFORMATION: Amplification primer

<400> SEQUENCE: 5
gaaaatggca ccaaattcta tat                                             23

<210> SEQ ID NO 6
<211> LENGTH: 23
<212> TYPE: DNA
<213> ORGANISM: Artificial sequence
<220> FEATURE:
<223> OTHER INFORMATION: Amplification primer

<400> SEQUENCE: 6
```

-continued atatagaatt tggtgccatt ttc   23

<210> SEQ ID NO 7
<211> LENGTH: 19
<212> TYPE: DNA
<213> ORGANISM: Artificial sequence
<220> FEATURE:
<223> OTHER INFORMATION: Amplification primer

<400> SEQUENCE: 7
tagaagtatt cactaaagt   19

<210> SEQ ID NO 8
<211> LENGTH: 28
<212> TYPE: DNA
<213> ORGANISM: Artificial Sequence
<220> FEATURE:
<223> OTHER INFORMATION: Amplification primer

<400> SEQUENCE: 8
tactgtctac aggcactgtg ccgtttac   28

<210> SEQ ID NO 9
<211> LENGTH: 18
<212> TYPE: DNA
<213> ORGANISM: Artificial sequence
<220> FEATURE:
<223> OTHER INFORMATION: Amplification primer

<400> SEQUENCE: 9
ggaatatttg atgagtat   18

<210> SEQ ID NO 10
<211> LENGTH: 18
<212> TYPE: DNA
<213> ORGANISM: Artificial sequence
<220> FEATURE:
<223> OTHER INFORMATION: Amplification primer

<400> SEQUENCE: 10
attcatttga aagagacg   18

<210> SEQ ID NO 11
<211> LENGTH: 795
<212> TYPE: PRT
<213> ORGANISM: Unknown
<220> FEATURE:
<223> OTHER INFORMATION: Variant of Lu-ECAM-1 from bovine endothelial
      cells

<400> SEQUENCE: 11

Met Val Leu Cys Leu Asn Val Ile Leu Phe Leu Thr Leu His Leu
    -20             -15                 -10

Leu Pro Gly Met Lys Ser Ser Met Val Asn Leu Ile Asn Asn Gly
    -5               1               5

Tyr Asp Gly Ile Val Ile Ala Ile Asn Pro Ser Val Pro Glu Asp
10              15                  20

Glu Lys Leu Ile Glu Asn Ile Lys Glu Met Val Thr Glu Ala Ser
25              30                  35

Thr Tyr Leu Phe His Ala Thr Lys Arg Arg Val Tyr Phe Arg Asn
40              45                  50

Val Ser Ile Leu Ile Pro Met Thr Trp Lys Ser Lys Ser Glu Tyr
55              60                  65

-continued

```
Phe Ile Pro Lys Gln Glu Ser Tyr Asp Gln Ala Asp Val Ile Val
 70                  75                  80

Ala Asn Pro Tyr Leu Lys Tyr Gly Asp Asp Pro Tyr Thr Leu Gln
 85                  90                  95

Tyr Gly Arg Cys Gly Glu Lys Gly Lys Tyr Ile His Phe Thr Pro
100                 105                 110

Asn Phe Leu Leu Thr Asn Asn Phe His Ile Tyr Gly Ser Arg Gly
115                 120                 125

Arg Val Phe Val His Glu Trp Ala His Leu Arg Trp Gly Ile Phe
130                 135                 140

Asp Glu Tyr Asn Val Asp Gln Pro Phe Tyr Ile Ser Arg Lys Asn
145                 150                 155

Thr Ile Glu Ala Thr Arg Cys Ser Thr His Ile Thr Gly Ile Asn
160                 165                 170

Val Val Phe Lys Lys Cys Pro Gly Gly Ser Cys Ile Thr Ser Leu
175                 180                 185

Cys Arg Arg Asp Ser Gln Thr Gly Leu Tyr Glu Ala Lys Cys Thr
190                 195                 200

Phe Leu Pro Lys Lys Ser Gln Thr Ala Lys Glu Ser Ile Met Phe
205                 210                 215

Met Pro Ser Leu His Ser Val Thr Glu Phe Cys Thr Glu Lys Thr
220                 225                 230

His Asn Thr Glu Ala Pro Asn Leu Gln Asn Lys Met Cys Asn Gly
235                 240                 245

Lys Ser Thr Trp Asp Val Ile Met Asn Ser Val Asp Phe Gln Asn
250                 255                 260

Thr Ser Pro Met Thr Glu Met Asn Pro Pro Thr His Pro Thr Phe
265                 270                 275

Ser Leu Leu Lys Ser Lys Gln Arg Val Val Cys Leu Val Leu Asp
280                 285                 290

Lys Ser Gly Ser Met Ser Ala Glu Asp Arg Leu Phe Gln Met Asn
295                 300                 305

Gln Ala Ala Glu Leu Tyr Leu Ile Gln Val Ile Glu Lys Gly Ser
310                 315                 320

Leu Val Gly Met Val Thr Phe Asp Ser Val Ala Glu Ile Gln Asn
325                 330                 335

His Leu Thr Arg Ile Thr Asp Asp Asn Val Tyr Gln Lys Ile Thr
340                 345                 350

Ala Lys Leu Pro Gln Val Ala Asn Gly Gly Thr Ser Ile Cys Arg
355                 360                 365

Gly Leu Lys Ala Gly Phe Gln Ala Ile Ile His Ser Asp Gln Ser
370                 375                 380

Thr Ser Gly Ser Glu Ile Ile Leu Leu Thr Asp Gly Glu Asp Asn
385                 390                 395

Glu Ile Asn Ser Cys Phe Glu Asp Val Lys Arg Ser Gly Ala Ile
400                 405                 410

Ile His Thr Ile Ala Leu Gly Pro Ser Ala Ala Lys Glu Leu Glu
415                 420                 425

Thr Lys Ser Asn Met Thr Gly Gly Tyr Arg Phe Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
```

```
                460             465             470
Leu Lys Ile Thr Gly Arg Lys Arg Val Asn Gly Thr Val Pro Val
475                     480                 485

Asp Ser Thr Val Gly Asn Asp Thr Phe Phe Val Val Thr Trp Thr
490                     495                 500

Ile Gln Lys Pro Glu Ile Val Leu Gln Asp Pro Lys Gly Lys Lys
505                     510                 515

Tyr Lys Thr Ser Asp Phe Lys Glu Asp Lys Leu Asn Ile Arg Ser
520                     525                 530

Ala Arg Leu Gln Ile Pro Gly Ile Ala Glu Thr Gly Thr Trp Thr
535                     540                 545

Tyr Ser Leu Leu Asn Asn His Ala Ser Ser Gln Met Leu Thr Val
550                     555                 560

Thr Val Thr Thr Arg Ala Arg Ser Pro Thr Ile Pro Pro Val Ile
565                     570                 575

Ala Thr Ala His Met Ser Gln His Thr Ala His Tyr Pro Ser Pro
580                     585                 590

Met Ile Val Tyr Ala Gln Val Ser Gln Gly Phe Leu Pro Val Leu
595                     600                 605

Gly Ile Ser Val Ile Ala Ile Ile Glu Thr Glu Asp Gly His Gln
610                     615                 620

Val Thr Leu Glu Leu Trp Asp Asn Gly Ala Gly Arg Asp Thr Val
625                     630                 635

Lys Asn Asp Gly Ile Tyr Ser Arg Tyr Phe Thr Asp Tyr Tyr Gly
640                     645                 650

Asn Gly Arg Tyr Ser Leu Lys Val His Ala Gln Ala Arg Asn Asn
655                     660                 665

Thr Ala Arg Leu Asn Leu Arg Gln Pro Gln Asn Lys Val Leu Tyr
670                     675                 680

Val Pro Gly Tyr Val Glu Asn Gly Lys Ile Ile Leu Asn Pro Pro
685                     690                 695

Arg Pro Glu Val Lys Asp Asp Leu Ala Lys Ala Lys Ile Glu Asp
700                     705                 710

Phe Ser Arg Leu Thr Ser Gly Gly Ser Phe Thr Val Ser Gly Ala
715                     720                 725

Pro Pro Pro Gly Asn His Pro Ser Val Phe Pro Pro Ser Lys Ile
730                     735                 740

Thr Asp Leu Glu Ala Lys Phe Lys Glu Asp Tyr Ile Gln Leu Ser
745                     750                 755

Trp Thr Ala Pro Gly Asn Val Leu Asp Lys Gly Lys Ala Glu Ser
760                     765             770                 774

<210> SEQ ID NO 12
<211> LENGTH: 821
<212> TYPE: PRT
<213> ORGANISM: Unknown
<220> FEATURE:
<223> OTHER INFORMATION: Variant of Lu-ECAM-1 from bovine endothelial
      cells

<400> SEQUENCE: 12

Met Val Leu Cys Leu Asn Val Ile Leu Phe Leu Thr Leu His Leu
    -20                 -15                 -10

Leu Pro Gly Met Lys Ser Ser Met Val Asn Leu Ile Asn Asn Gly
    -5                  1                   5
```

-continued

```
Tyr Asp Gly Ile Val Ile Ala Ile Asn Pro Ser Val Pro Glu Asp
 10              15                  20

Glu Lys Leu Ile Glu Asn Ile Lys Glu Met Val Thr Glu Ala Ser
 25              30                  35

Thr Tyr Leu Phe His Ala Thr Lys Arg Arg Val Tyr Phe Arg Asn
 40              45                  50

Val Ser Ile Leu Ile Pro Met Thr Trp Lys Ser Lys Ser Glu Tyr
 55              60                  65

Phe Ile Pro Lys Gln Glu Ser Tyr Asp Gln Ala Asp Val Ile Val
 70              75                  80

Ala Asn Pro Tyr Leu Lys Tyr Gly Asp Asp Pro Tyr Thr Leu Gln
 85              90                  95

Tyr Gly Arg Cys Gly Glu Lys Gly Lys Tyr Ile His Phe Thr Pro
100             105                 110

Asn Phe Leu Leu Thr Asn Asn Phe His Ile Tyr Gly Ser Arg Gly
115             120                 125

Arg Val Phe Val His Glu Trp Ala His Leu Arg Trp Gly Ile Phe
130             135                 140

Asp Glu Tyr Asn Val Asp Gln Pro Phe Tyr Ile Ser Arg Lys Asn
145             150                 155

Thr Ile Glu Ala Thr Arg Cys Ser Thr His Ile Thr Gly Ile Asn
160             165                 170

Val Val Phe Lys Lys Cys Pro Gly Gly Ser Cys Ile Thr Ser Leu
175             180                 185

Cys Arg Arg Asp Ser Gln Thr Gly Leu Tyr Glu Ala Lys Cys Thr
190             195                 200

Phe Leu Pro Lys Lys Ser Gln Thr Ala Lys Glu Ser Ile Met Phe
205             210                 215

Met Pro Ser Leu His Ser Val Thr Glu Phe Cys Thr Glu Lys Thr
220             225                 230

His Asn Thr Glu Ala Pro Asn Leu Gln Asn Lys Met Cys Asn Gly
235             240                 245

Lys Ser Thr Trp Asp Val Ile Met Asn Ser Val Asp Phe Gln Asn
250             255                 260

Thr Ser Pro Met Thr Glu Met Asn Pro Pro Thr His Pro Thr Phe
265             270                 275

Ser Leu Leu Lys Ser Lys Gln Arg Val Val Cys Leu Val Leu Asp
280             285                 290

Lys Ser Gly Ser Met Ser Ala Glu Asp Arg Leu Phe Gln Met Asn
295             300                 305

Gln Ala Ala Glu Leu Tyr Leu Ile Gln Val Ile Glu Lys Gly Ser
310             315                 320

Leu Val Gly Met Val Thr Phe Asp Ser Val Ala Glu Ile Gln Asn
325             330                 335

His Leu Thr Arg Ile Thr Asp Asp Asn Val Tyr Gln Lys Ile Thr
340             345                 350

Ala Lys Leu Pro Gln Val Ala Asn Gly Gly Thr Ser Ile Cys Arg
355             360                 365

Gly Leu Lys Ala Gly Phe Gln Ala Ile Ile His Ser Asp Gln Ser
370             375                 380

Thr Ser Gly Ser Glu Ile Ile Leu Leu Thr Asp Gly Glu Asp Asn
385             390                 395

Glu Ile Asn Ser Cys Phe Glu Asp Val Lys Arg Ser Gly Ala Ile
```

```
                400             405             410
Ile His Thr Ile Ala Leu Gly Pro Ser Ala Lys Glu Leu Glu
415                 420                 425

Thr Lys Ser Asn Met Thr Gly Gly Tyr Arg Phe Phe Ala Asn Lys
430                 435                 440

Asp Ile Thr Gly Leu Thr Asn Ala Phe Ser Arg Ile Ser Ser Arg
445                 450                 455

Ser Gly Ser Ile Thr Gln Gln Ala Ile Gln Leu Glu Ser Lys Ala
460                 465                 470

Leu Lys Ile Thr Gly Arg Lys Arg Val Asn Gly Thr Val Pro Val
475                 480                 485

Asp Ser Thr Val Gly Asn Asp Thr Phe Phe Val Val Thr Trp Thr
490                 495                 500

Ile Gln Lys Pro Glu Ile Val Leu Gln Asp Pro Lys Gly Lys Lys
505                 510                 515

Tyr Lys Thr Ser Asp Phe Lys Glu Asp Lys Leu Asn Ile Arg Ser
520                 525                 530

Ala Arg Leu Gln Ile Pro Gly Ile Ala Glu Thr Gly Thr Trp Thr
535                 540                 545

Tyr Ser Leu Leu Asn Asn His Ala Ser Ser Gln Met Leu Thr Val
550                 555                 560

Thr Val Thr Thr Arg Ala Arg Ser Pro Thr Ile Pro Pro Val Ile
565                 570                 575

Ala Thr Ala His Met Ser Gln His Thr Ala His Tyr Pro Ser Pro
580                 585                 590

Met Ile Val Tyr Ala Gln Val Ser Gln Gly Phe Leu Pro Val Leu
595                 600                 605

Gly Ile Ser Val Ile Ala Ile Ile Glu Thr Glu Asp Gly His Gln
610                 615                 620

Val Thr Leu Glu Leu Trp Asp Asn Gly Ala Gly Arg Asp Thr Val
625                 630                 635

Lys Asn Asp Gly Ile Tyr Ser Arg Tyr Phe Thr Asp Tyr Tyr Gly
640                 645                 650

Asn Gly Arg Tyr Ser Leu Lys Val His Ala Gln Ala Arg Asn Asn
655                 660                 665

Thr Ala Arg Leu Asn Leu Arg Gln Pro Gln Asn Lys Val Leu Tyr
670                 675                 680

Val Pro Gly Tyr Val Glu Asn Gly Lys Ile Ile Leu Asn Pro Pro
685                 690                 695

Arg Pro Glu Val Lys Asp Asp Leu Ala Lys Ala Lys Ile Glu Asp
700                 705                 710

Phe Ser Arg Leu Thr Ser Gly Gly Ser Phe Thr Val Ser Gly Ala
715                 720                 725

Pro Pro Pro Gly Asn His Pro Ser Val Phe Pro Ser Lys Ile
730                 735                 740

Thr Asp Leu Glu Ala Lys Phe Lys Glu Asp Tyr Ile Gln Leu Ser
745                 750                 755

Trp Thr Ala Pro Gly Asn Val Leu Asp Lys Gly Lys Ala Ala Ser
760                 765                 770

Gly Ser Phe Pro Met Ser Arg Phe Ser His Gln Val Ala Lys Val
775                 780                 785

Leu Glu Leu Gln Leu Gln His Gln Ser Phe Gln
790                 795                 800
```

<210> SEQ ID NO 13
<211> LENGTH: 342
<212> TYPE: PRT
<213> ORGANISM: Unknown
<220> FEATURE:
<223> OTHER INFORMATION: Variant of Lu-ECAM-1 from bovine endothelial cells

<400> SEQUENCE: 13

```
Met Val Leu Cys Leu Asn Val Ile Leu Phe Leu Thr Leu His Leu
    -20                 -15                 -10

Leu Pro Gly Met Lys Ser Ser Met Val Asn Leu Ile Asn Asn Gly
     -5                   1               5

Tyr Asp Gly Ile Val Ile Ala Ile Asn Pro Ser Val Pro Glu Asp
 10              15              20

Glu Lys Leu Ile Glu Asn Ile Lys Glu Met Val Thr Glu Ala Ser
 25              30              35

Thr Tyr Leu Phe His Ala Thr Lys Arg Arg Val Tyr Phe Arg Asn
 40              45              50

Val Ser Ile Leu Ile Pro Met Thr Trp Lys Ser Lys Ser Glu Tyr
 55              60              65

Phe Ile Pro Lys Gln Glu Ser Tyr Asp Gln Ala Asp Val Ile Val
 70              75              80

Ala Asn Pro Tyr Leu Lys Tyr Gly Asp Asp Pro Tyr Thr Leu Gln
 85              90              95

Tyr Gly Arg Cys Gly Glu Lys Gly Lys Tyr Ile His Phe Thr Pro
100             105             110

Asn Phe Leu Leu Thr Asn Asn Phe His Ile Tyr Gly Ser Arg Gly
115             120             125

Arg Val Phe Val His Glu Trp Ala His Leu Arg Trp Gly Ile Phe
130             135             140

Asp Glu Tyr Asn Val Asp Gln Pro Phe Tyr Ile Ser Arg Lys Asn
145             150             155

Thr Ile Glu Ala Thr Arg Cys Ser Thr His Ile Thr Gly Ile Asn
160             165             170

Val Val Phe Lys Lys Cys Pro Gly Gly Ser Cys Ile Thr Ser Leu
175             180             185

Cys Arg Arg Asp Ser Gln Thr Gly Leu Tyr Glu Ala Lys Cys Thr
190             195             200

Phe Leu Pro Lys Lys Ser Gln Thr Ala Lys Glu Ser Ile Met Phe
205             210             215

Met Pro Ser Leu His Ser Val Thr Glu Phe Cys Thr Glu Lys Thr
220             225             230

His Asn Thr Glu Ala Pro Asn Leu Gln Asn Lys Met Cys Asn Gly
235             240             245

Lys Ser Thr Trp Asp Val Ile Met Asn Ser Val Asp Phe Gln Asn
250             255             260

Thr Ser Pro Met Thr Glu Met Asn Pro Pro Thr His Pro Thr Phe
265             270             275

Ser Leu Leu Lys Ser Lys Gln Arg Val Val Cys Leu Val Leu Asp
280             285             290

Lys Ser Gly Ser Met Ser Ala Glu Asp Ile Tyr Leu Leu Ala Leu
295             300             305

Leu Ile Lys Ile Phe Lys Leu Ile Gly Asn Thr Ile
```

```
<210> SEQ ID NO 14
<211> LENGTH: 335
<212> TYPE: DNA
<213> ORGANISM: Artificial sequence
<220> FEATURE:
<223> OTHER INFORMATION: Oligonucleotide probe

<400> SEQUENCE: 14
caacagctac attataagaa taagtaagag tttcatggat cgtcaagaag              50
attttgacaa tgcgacttta gtgaatactt ctaatctaat acctaaggag             100
gccggatcaa agaaaattt tgaatttaag ccagaacatt ttagagtaga              150
aaatggcacc aaattctata tttcagtcca agccatcaac gaagccaatc             200
tcatctcaga ggtttctcac attgtacaag caatcaaatt tattcctcta             250
ccagaagaca gtgtccatga tctgggtacc aagatttctg aaatcactct             300
ggcaatttta ggattaccaa tgattttctc tgtat                             335

<210> SEQ ID NO 15
<211> LENGTH: 17
<212> TYPE: PRT
<213> ORGANISM: Artificial sequence
<220> FEATURE:
<223> OTHER INFORMATION: Synthetic peptide

<400> SEQUENCE: 15

Glu Asp Glu Lys Leu Ile Glu Asn Ile Lys Glu Met Val Thr Glu
                 5                  10                  15
Ala Ser
    17

<210> SEQ ID NO 16
<211> LENGTH: 17
<212> TYPE: PRT
<213> ORGANISM: Artificial sequence
<220> FEATURE:
<223> OTHER INFORMATION: synthetic peptide

<400> SEQUENCE: 16

Gln Asp Pro Lys Gly Lys Lys Tyr Lys Thr Ser Asp Phe Lys Glu
 1               5                  10                  15
Asp Lys
    17

<210> SEQ ID NO 17
<211> LENGTH: 24
<212> TYPE: DNA
<213> ORGANISM: Artificial Sequence
<220> FEATURE:
<223> OTHER INFORMATION: Amplification primer

<400> SEQUENCE: 17
atgttcaact catattactg gtat                                          24

<210> SEQ ID NO 18
<211> LENGTH: 20
<212> TYPE: DNA
<213> ORGANISM: Artificial sequence
<220> FEATURE:
<223> OTHER INFORMATION: Amplification primer

<400> SEQUENCE: 18
```

-continued tgtaggtttg gagcttctgt                                               20

<210> SEQ ID NO 19
<211> LENGTH: 20
<212> TYPE: DNA
<213> ORGANISM: Artificial Sequence
<220> FEATURE:
<223> OTHER INFORMATION: Amplification primer

<400> SEQUENCE: 19
cacagacagg gctgtatgaa                                               20

<210> SEQ ID NO 20
<211> LENGTH: 23
<212> TYPE: DNA
<213> ORGANISM: Artificial Sequence
<220> FEATURE:
<223> OTHER INFORMATION: Amplification Primer

<400> SEQUENCE: 20
ggagatgtat tctgaaagtc aac                                           23

<210> SEQ ID NO 21
<211> LENGTH: 24
<212> TYPE: DNA
<213> ORGANISM: Artificial Sequence
<220> FEATURE:
<223> OTHER INFORMATION: Amplification primer

<400> SEQUENCE: 21
atgttcaact catattactg gtac                                          24

<210> SEQ ID NO 22
<211> LENGTH: 20
<212> TYPE: DNA
<213> ORGANISM: Artificial Sequence
<220> FEATURE:
<223> OTHER INFORMATION: Amplification primer

<400> SEQUENCE: 22
tgtaggtttg gagcttccac                                               20

<210> SEQ ID NO 23
<211> LENGTH: 20
<212> TYPE: DNA
<213> ORGANISM: Artificial Sequence
<220> FEATURE:
<223> OTHER INFORMATION: Amplification primer

<400> SEQUENCE: 23
cacagacagg gctgtatgag                                               20

<210> SEQ ID NO 24
<211> LENGTH: 23
<212> TYPE: DNA
<213> ORGANISM: Artificial Sequence
<220> FEATURE:
<223> OTHER INFORMATION: Amplification primer

<400> SEQUENCE: 24
ggagatgtat tttgaaagtc agt                                           23

<210> SEQ ID NO 25
<211> LENGTH: 32
<212> TYPE: DNA
<213> ORGANISM: Artificial Sequence

```
<220> FEATURE:
<223> OTHER INFORMATION: Amplification primer

<400> SEQUENCE: 25
actgaattca gcagactaac ctctggaggg tc                                32

<210> SEQ ID NO 26
<211> LENGTH: 32
<212> TYPE: DNA
<213> ORGANISM: Artificial Sequence
<220> FEATURE:
<223> OTHER INFORMATION: Amplification primer

<400> SEQUENCE: 26
tctactagta gctttagcta ctgaagaaca ag                                32

<210> SEQ ID NO 27
<211> LENGTH: 3007
<212> TYPE: DNA
<213> ORGANISM: Homo sapiens

<400> SEQUENCE: 27
taacccgcat tttccaaaga gaggaatcac agggagatgt acagca atg ggg         52 cca ttt aag agt tct gtg ttc atc ttg att ctt cac ctt cta gaa        97 ggg gcc ctg agt aat tca ctc att cag ctg aac aac aat ggc tat        142 gaa ggc att gtc gtt gca atc gac ccc aat gtg cca gaa gat gaa        187 aca ctc att caa caa ata aag gac atg gtg acc cag gca tct ctg        232 tat ctg ttt gaa gct aca gga aag cga ttt tat ttc aaa aat gtt        277 gcc att ttg att cct gaa aca tgg aag aca aag gct gac tat gtg        322 aga cca aaa ctt gag acc tac aaa aat gct gat gtt ctg gtt gct        367 gag tct act cct cca ggt aat gat gaa ccc tac act gag cag atg        412 ggc aac tgt gga gag aag ggt gaa agg atc cac ctc act cct gat        457 ttc att gca gga aaa aag tta gct gaa tat gga cca caa ggt aag        502 gca ttt gtc cat gag tgg gct cat cta cga tgg gga gta ttt gac        547 gag tac aat aat gat gag aaa ttc tac tta tcc aat gga aga ata        592 caa gca gta aga tgt tca gca ggt att act ggt aca aat gta gta        637 aag aag tgt cag gga ggc agc tgt tac acc aaa aga tgc aca ttc        682 aat aaa gtt aca gga ctc tat gaa aaa gga tgt gag ttt gtt ctc        727 caa tcc cgc cag acg gag aag gct tct ata atg ttt gca caa cat        772 gtt gat tct ata gtt gaa ttc tgt aca gaa caa aac cac aac aaa        817 gaa gct cca aac aag caa atc aaa aaa tgc aat ctc cga agc aca        862 tgg gaa gtg atc cgt gat tct gag gac ttt aag aaa acc act cct        907 atg aca aca cag cca cca aat ccc acc ttc tca ttg ctg cag att        952 gga caa aga att gtg tgt tta gtc ctt gac aaa tct gga agc atg        997 gcg act ggt aac cgc ctc aat cga ctg aat caa gca ggc cag ctt        1042 ttc ctg ctg cag aca gtt gag ctg ggg tcc tgg gtt ggg atg gtg        1087 aca ttt gac agt gct gcc cat gta caa gtg aac tca ata cag ata        1132 aac agt ggc agt gac agg gac aca ctc gcc aaa aga tta cct gca        1177
```

| | |
|---|---|
| gca gct tca gga ggg acg tcc atc tgc agc ggg ctt cga tcg gca | 1222 |
| ttt act gtg att agg aag aaa tat cca act gat gga tct gaa att | 1267 |
| gtg ctg ctg acg gat ggg gaa gac aac act ata agt ggg tgc ttt | 1312 |
| aac gag gtc aaa caa agt ggt gcc atc atc cac aca gtc gct ttg | 1357 |
| ggg ccc tct gca gct caa gaa cta gag gag ctg tcc aaa atg aca | 1402 |
| gga ggt tta cag aca tat gct tca gat caa gtt cag aac aat ggc | 1447 |
| ctc att gat gct ttt ggg gcc ctt tca tca gga aat gga gct gtc | 1492 |
| tct cag cgc tcc atc cag ctt gag agt aag gga tta acc ctc cag | 1537 |
| aac agc cag tgg atg aat ggc aca gtg atc gtg gac agc acc gtg | 1582 |
| gga aag gac act ttg ttt ctt atc acc tgg aca acg cag cct ccc | 1627 |
| caa atc ctt ctc tgg gat ccc agt gga cag aag caa ggt ggc ttt | 1672 |
| gta gtg gac aaa aac acc aaa atg gcc tac ctc caa atc cca ggc | 1717 |
| att gct aag gtt ggc act tgg aaa tac agt ctg caa gca agc tca | 1762 |
| caa acc ttg acc ctg act gtc acg tcc cgt gcg tcc aat gct acc | 1807 |
| ctg cct cca att aca gtg act tcc aaa acg aac aag gac acc agc | 1852 |
| aaa ttc ccc agc cct ctg gta gtt tat gca aat att cgc caa gga | 1897 |
| gcc tcc cca att ctc agg gcc agt gtc aca gcc ctg att gaa tca | 1942 |
| gtg aat gga aaa aca gtt acc ttg gaa cta ctg gat aat gga gca | 1987 |
| ggt gct gat gct act aag gat gac ggt gtc tac tca agg tat ttc | 2032 |
| aca act tat gac acg aat ggt aga tac agt gta aaa gtg cgg gct | 2077 |
| ctg gga gga gtt aac gca gcc aga cgg aga gtg ata ccc cag cag | 2122 |
| agt gga gca ctg tac ata cct ggc tgg att gag aat gat gaa ata | 2167 |
| caa tgg aat cca cca aga cct gaa att aat aag gat gat gtt caa | 2212 |
| cac aag caa gtg tgt ttc agc aga aca tcc tcg gga ggc tca ttt | 2257 |
| gtg gct tct gat gtc cca aat gct ccc ata cct gat ctc ttc cca | 2302 |
| cct ggc caa atc acc gac ctg aag gcg gaa att cac ggg ggc agt | 2347 |
| ctc att aat ctg act tgg aca gct cct ggg gat gat tat gac cat | 2392 |
| gga aca gct cac aag tat atc att cga ata agt aca agt att ctt | 2437 |
| gat ctc aga gac aag ttc aat gaa tct ctt caa gtg aat act act | 2482 |
| gct ctc atc cca aag gaa gcc aac tct gag gaa gtc ttt ttg ttt | 2527 |
| aaa cca gaa aac att act ttt gaa aat ggc aca gat ctt ttc att | 2572 |
| gct att cag gct gtt gat aag gtc gat ctg aaa tca gaa ata tcc | 2617 |
| aac att gca cga gta tct ttg ttt att cct cca cag act ccg cca | 2662 |
| gag aca cct agt cct gat gaa acg tct gct cct tgt cct aat att | 2707 |
| cat atc aac agc acc att cct ggc att cac att tta aaa att atg | 2752 |
| tgg aag tgg ata gga gaa ctg cag ctg tca ata gcc tagggctgaa | 2798 |
| tttttgtcag ataataaaaa taaatcattc atccttttttt ttgattataa | 2848 |
| aatttttttaa aatgtatttt agaattcctg tagggggcga tatactaaat | 2898 |
| gtatatagta catttatact aaatgtattc ctgtaggggg cgatatacta | 2948 |
| aatgtatttt agaattcctg tagggggcga taaaataaaa tgctaaacaa | 2998 | ctggggaaa 3007

<210> SEQ ID NO 28
<211> LENGTH: 914
<212> TYPE: PRT
<213> ORGANISM: Homo sapiens

<400> SEQUENCE: 28

Met Gly Pro Phe Lys Ser Ser Val Phe Ile Leu Ile Leu His Leu
1               5                   10                  15

Leu Glu Gly Ala Leu Ser Asn Ser Leu Ile Gln Leu Asn Asn Asn
                20                  25                  30

Gly Tyr Glu Gly Ile Val Val Ala Ile Asp Pro Asn Val Pro Glu
                35                  40                  45

Asp Glu Thr Leu Ile Gln Gln Ile Lys Asp Met Val Thr Gln Ala
                50                  55                  60

Ser Leu Tyr Leu Phe Glu Ala Thr Gly Lys Arg Phe Tyr Phe Lys
                65                  70                  75

Asn Val Ala Ile Leu Ile Pro Glu Thr Trp Lys Thr Lys Ala Asp
                80                  85                  90

Tyr Val Arg Pro Lys Leu Glu Thr Tyr Lys Asn Ala Asp Val Leu
                95                  100                 105

Val Ala Glu Ser Thr Pro Pro Gly Asn Asp Glu Pro Tyr Thr Glu
                110                 115                 120

Gln Met Gly Asn Cys Gly Glu Lys Gly Glu Arg Ile His Leu Thr
                125                 130                 135

Pro Asp Phe Ile Ala Gly Lys Lys Leu Ala Glu Tyr Gly Pro Gln
                140                 145                 150

Gly Lys Ala Phe Val His Glu Trp Ala His Leu Arg Trp Gly Val
                155                 160                 165

Phe Asp Glu Tyr Asn Asn Asp Glu Lys Phe Tyr Leu Ser Asn Gly
                170                 175                 180

Arg Ile Gln Ala Val Arg Cys Ser Ala Gly Ile Thr Gly Thr Asn
                185                 190                 195

Val Val Lys Lys Cys Gln Gly Gly Ser Cys Tyr Thr Lys Arg Cys
                200                 205                 210

Thr Phe Asn Lys Val Thr Gly Leu Tyr Glu Lys Gly Cys Glu Phe
                215                 220                 225

Val Leu Gln Ser Arg Gln Thr Glu Lys Ala Ser Ile Met Phe Ala
                230                 235                 240

Gln His Val Asp Ser Ile Val Glu Phe Cys Thr Glu Gln Asn His
                245                 250                 255

Asn Lys Glu Ala Pro Asn Lys Gln Asn Gln Lys Cys Asn Leu Arg
                260                 265                 270

Ser Thr Trp Glu Val Ile Arg Asp Ser Glu Asp Phe Lys Lys Thr
                275                 280                 285

Thr Pro Met Thr Thr Gln Pro Pro Asn Pro Thr Phe Ser Leu Leu
                290                 295                 300

Gln Ile Gly Gln Arg Ile Val Cys Leu Val Leu Asp Lys Ser Gly
                305                 310                 315

Ser Met Ala Thr Gly Asn Arg Leu Asn Arg Leu Asn Gln Ala Gly
                320                 325                 330

Gln Leu Phe Leu Leu Gln Thr Val Glu Leu Gly Ser Trp Val Gly
                335                 340                 345

```
Met Val Thr Phe Asp Ser Ala Ala His Val Gln Ser Glu Leu Ile
                350                 355                 360

Gln Ile Asn Ser Gly Ser Asp Arg Asp Thr Leu Ala Lys Arg Leu
                365                 370                 375

Pro Ala Ala Ala Ser Gly Gly Thr Ser Ile Cys Ser Gly Leu Arg
                380                 385                 390

Ser Ala Phe Thr Val Ile Arg Lys Lys Tyr Pro Thr Asp Gly Ser
                395                 400                 405

Glu Ile Val Leu Leu Thr Asp Gly Glu Asp Asn Thr Ile Ser Gly
                410                 415                 420

Cys Phe Asn Glu Val Lys Gln Ser Gly Ala Ile Ile His Thr Val
                425                 430                 435

Ala Leu Gly Pro Ser Ala Ala Gln Glu Leu Glu Glu Leu Ser Lys
                440                 445                 450

Met Thr Gly Gly Leu Gln Thr Tyr Ala Ser Asp Gln Val Gln Asn
                455                 460                 465

Asn Gly Leu Ile Asp Ala Phe Gly Ala Leu Ser Ser Gly Asn Gly
                470                 475                 480

Ala Val Ser Gln Arg Ser Ile Gln Leu Glu Ser Lys Gly Leu Thr
                485                 490                 495

Leu Gln Asn Ser Gln Trp Met Asn Gly Thr Val Ile Val Asp Ser
                500                 505                 510

Thr Val Gly Lys Asp Thr Leu Phe Leu Ile Thr Trp Thr Thr Gln
                515                 520                 525

Pro Pro Gln Ile Leu Leu Trp Asp Pro Ser Gly Gln Lys Gln Gly
                530                 535                 540

Gly Phe Val Val Asp Lys Asn Thr Lys Met Ala Tyr Leu Gln Ile
                545                 550                 555

Pro Gly Ile Ala Lys Val Gly Thr Trp Lys Tyr Ser Leu Gln Ala
                560                 565                 570

Ser Ser Gln Thr Leu Thr Leu Thr Val Thr Ser Arg Ala Ser Asn
                575                 580                 585

Ala Thr Leu Pro Pro Ile Thr Val Thr Ser Lys Thr Asn Lys Asp
                590                 595                 600

Thr Ser Lys Phe Pro Ser Pro Leu Val Val Tyr Ala Asn Ile Arg
                605                 610                 615

Gln Gly Ala Ser Pro Ile Leu Arg Ala Ser Val Thr Ala Leu Ile
                620                 625                 630

Glu Ser Val Asn Gly Lys Thr Val Thr Leu Gln Leu Leu Asp Asn
                635                 640                 645

Gly Ala Gly Ala Asp Ala Thr Lys Asp Asp Gly Val Tyr Ser Arg
                650                 655                 660

Tyr Phe Thr Thr Tyr Asp Thr Asn Gly Arg Tyr Ser Val Lys Val
                665                 670                 675

Arg Ala Leu Gly Gly Val Asn Ala Ala Arg Arg Val Ile Pro
                680                 685                 690

Gln Gln Ser Gly Ala Leu Tyr Ile Pro Gly Trp Ile Glu Asn Asp
                695                 700                 705

Glu Ile Gln Trp Asn Pro Pro Arg Pro Glu Ile Asn Lys Asp Asp
                710                 715                 720

Val Gln His Lys Gln Val Cys Phe Ser Arg Thr Ser Ser Gly Gly
                725                 730                 735
```

-continued

```
Ser Phe Val Ala Ser Asp Val Pro Asn Ala Pro Ile Pro Asp Leu
            740                 745                 750

Phe Pro Pro Gly Gln Ile Thr Asp Leu Lys Ala Glu Ile His Gly
            755                 760                 765

Gly Ser Leu Ile Asn Leu Thr Trp Thr Ala Pro Gly Asp Asp Tyr
            770                 775                 780

Asp His Gly Thr Ala His Lys Tyr Ile Ile Arg Ile Ser Thr Ser
            785                 790                 795

Ile Leu Asp Leu Arg Asp Lys Phe Asn Glu Ser Leu Gln Val Asn
            800                 805                 810

Thr Thr Ala Leu Ile Pro Lys Glu Ala Asn Ser Glu Glu Val Phe
            815                 820                 825

Leu Phe Lys Pro Glu Asn Ile Thr Phe Glu Asn Gly Thr Asp Leu
            830                 835                 840

Phe Ile Ala Ile Gln Ala Val Asp Lys Val Asp Leu Lys Ser Glu
            845                 850                 855

Ile Ser Asn Ile Ala Arg Val Ser Leu Phe Ile Pro Pro Gln Thr
            860                 865                 870

Pro Pro Glu Thr Pro Ser Pro Asp Glu Thr Ser Ala Pro Cys Pro
            875                 880                 885

Asn Ile His Ile Asn Ser Thr Ile Pro Gly Ile His Ile Leu Lys
            890                 895                 900

Ile Met Trp Lys Trp Ile Gly Glu Leu Gln Leu Ser Ile Ala
            905                 910             914
```

<210> SEQ ID NO 29
<211> LENGTH: 3418
<212> TYPE: DNA
<213> ORGANISM: Homo sapiens

<400> SEQUENCE: 29

| | |
|---|---|
| tttgtttaac atgcaaga atg gtg ttc agt ctg aag gtg att ctc ttc | 48 |
| cta tcc ttg ctt ctc tcg cct gta ttg aaa agc tca ctg gta act | 93 |
| ttg aat aac aat gga tat gat ggc att gtg att gca att aat ccc | 138 |
| agt gta cca gaa gat gaa aaa ctc att caa aac ata aag gaa atg | 183 |
| gta act gaa gca tct act cac ctg ttt cat gcc acc aaa caa aga | 228 |
| gct tat ttc agg aat gta agc att tta att cca atg acc tac aaa | 273 |
| tca aaa tct gag tac tta atc cca aaa caa gaa aca tat gac cag | 318 |
| gca gat gtc ata gtt gct gat ctt tac ctg aaa tac gga gat gat | 363 |
| ccc tat aca ctt caa tat gga caa tgt gga gat aaa gga caa tat | 408 |
| ata cat ttt act cca aac ttc ttg ttg act aat aac ttg gct acc | 453 |
| tat ggg cct cga ggt aaa gta ttt gtc cat ggg tgg gcc cat ctc | 498 |
| cgg tgg gga gta ttt gat gag tat aat gtg gac cag cca ttc tat | 543 |
| att tcc aga aga aac act act gaa gca aca aga tgt tcc act cgt | 588 |
| att act gtt tac atg gtt ttg aac gaa tgc aag ggg gcc agc tgt | 633 |
| ata gca cga cca ttc aga cgt gac tca cag aca ggg ctg tat gaa | 678 |
| gca aaa tgt aca ttt atc cca aag aga tcc cag act gcc aag gaa | 723 |
| tcc att gtg ttt atg caa aat ctt gat tct gtg act gaa ttt gt | 768 |
| act gaa aaa aca cac aat aaa gaa gct cca aac cta tat aac aaa | 813 |

| | |
|---|---|
| atg tgc aat cac aga agc aca tgg gat gta atc atg agc tct gaa | 858 |
| gat ttt cag cat tta tct ccc atg aca gaa ata aat tta cct cgt | 903 |
| cct aca ttt tca ttg ctc aag tcc aaa cag cgt gta gtc tgt ttg | 948 |
| gta ctt gat aaa tct gga agc atg aat gca gaa gac cgt ctc ttt | 993 |
| cga atg aat caa gca gca gaa ttg tac ttg att caa att att gaa | 1038 |
| aag gga tcc ttg gtt ggg ttg gtc aca ttt gac agt ttt gct aaa | 1083 |
| atc caa agt aag ctc ata aaa ata att gat gat aac act tac caa | 1128 |
| aag atc act gca aac ctg cct caa gaa gct gat ggt ggc act tca | 1173 |
| att tgc agg gga ctc aaa gca gga ttt cag gca att ccc cag agt | 1218 |
| aat cag agt act ttc ggt tct gaa atc ata tta cta aca gat ggg | 1263 |
| gaa gat tat caa ata agc tta tgc ttt gga gag gta aaa caa agt | 1308 |
| ggc aca gtc atc cac acc att gct ctg ggg ccg tct gct gac gaa | 1353 |
| gaa ctg gag acc ctg tca aat atg aca gga tta cat aag gga cac | 1398 |
| tgt tat act gaa agt tca tat agt gct ggg aag ttc atc ttt tgt | 1443 |
| gga cat cgt ttt tat gcc cat aaa aac ata aat ggc ctt att gat | 1488 |
| gct ttc agc aga att tca tct aga agt ggc agc atc tct cag cag | 1533 |
| gct ctt cag ttg gaa agt aaa act ttg aat atc cca gcg aag aaa | 1578 |
| tgg ata aat ggt aca gtg cct gtg gat agt aca gtt aga aat gat | 1623 |
| act tcc ttt gtt gtc aca tgg acg ata caa aag cca gca ata att | 1668 |
| ctt caa gat cca aaa gga aaa aaa tat act acc tca gat ttt caa | 1713 |
| gaa ggt gaa cta aat att cgg tct gcc cgt ctt cga ata cca ggt | 1758 |
| att gca gag aca ggc act tgg act tac agc gtt cga aac aat cat | 1803 |
| acc aaa tct caa ttg cta act gtg aca atg acc act cga gca aga | 1848 |
| agc cct acc aca ctc cca gta att gca act gct cac atg agt caa | 1893 |
| aat aca gct cat tac cct agc cca gtg att gtt tat gca tgt gtc | 1938 |
| agt caa ggg ttt ctt cct gtt ctg gga tca aat gta aca gcc att | 1983 |
| ata gaa aat gaa gag gga cat caa gta aca ttg gag ctc tgc gac | 2028 |
| aat ggc gca ggt gct gat tct gtc aag aat gat ggc atc tac tca | 2073 |
| agg tat ttt aca gat tac cat gga aat ggt aga tac agt tta aaa | 2118 |
| gtg ctt acc cag gca aga aaa aac aca gct agg cta agt caa caa | 2163 |
| cag aat aaa gct ctg tat gta ccg cgc tat gct gaa aat gga aaa | 2208 |
| att ata ctg aac cca tcc aaa cct gaa gtc aca gat gat gtg gaa | 2253 |
| gga gct caa aca gac gac ttc agc aga ctc acc tct gga ggg tcg | 2298 |
| ttt act gta tca gga gtg cct cct aat ggt aat cat tct cag gtg | 2343 |
| ttc tca cct ggt aaa att gta gac ctc gag gct aag ttt caa gga | 2388 |
| gat cat att caa ctt tca tgg act gcc cct ggc aag gtc ctc gat | 2433 |
| aaa gga aga gct gag agc tac att ata aga ata agt aaa cat ttc | 2478 |
| ctg gac ctc caa gaa gat ttt gat aaa gct gct tta ata aat act | 2523 |
| tct ggt ctg ata cct aag gag cct ggt tca gta gaa agt ttt gaa | 2568 |

-continued

| | |
|---|---|
| ttt aaa cca gaa cct tct aaa ata gag aat ggt acg aca ttc tat | 2613 |
| att gca att caa gcc atc cat gaa gcc aat gtc acc tca gag gtt | 2658 |
| tca aac att gca caa gca act aac ttt att cct cca cag gaa ccc | 2703 |
| agc att cct gat ctg ggt acc aat att tct gca atc agt ttg gca | 2748 |
| att ttt gga tta gct gta att tta tct ata ttt tat act aga aat | 2793 |
| tat att aga act caa att caa tgt tat aca tac ttg gta aac att | 2838 |
| tat tta aaa ttt aat tta cta tac tta ttg tct att ata aag ctc | 2883 |
| att ata ata tat aaa gtg aag tac aaa agt tgt aag ttt cct aat | 2928 |
| tac ttg att aat tat tac tat ttg agt tat tat atg tta atc aaa | 2973 |
| atg agt ata tca ttt cct gtc tgg aat aat cca ctc att aat ttt | 3018 |
| taatatgaaa agatatatat ttgtacttgt aagcatttta agaaacattt | 3068 |
| ttaaagtgtg ctacaaattc atttggtgta ctaacatcaa aatgtatcca | 3118 |
| agccatttaa aaatatttta tatatacata gtagcaaata gttttataga | 3168 |
| tttatttgta tcgcattttt tattacaaat gaatatttca tgtttatata | 3218 |
| agctgtaatc aaaaaggact agtagtagta gtaaggaagt caaatttgtt | 3268 |
| ttttatcat tgattataag tggtatattt gttttttgtc attgattaaa | 3318 |
| agtgatttta gccctaggcc cgaaatgact agcaaatatc attttctgta | 3368 |
| tgaattgtgg aacatcacaa taaaattatt tctgtgctga tgctaaaaaa | 3418 |

<210> SEQ ID NO 30
<211> LENGTH: 1000
<212> TYPE: PRT
<213> ORGANISM: Homo sapiens

<400> SEQUENCE: 30

Met Val Phe Ser Leu Lys Val Ile Leu Phe Leu Ser Leu Leu Leu
1               5                   10                  15

Ser Pro Val Leu Lys Ser Ser Leu Val Thr Leu Asn Asn Asn Gly
                20                  25                  30

Tyr Asp Gly Ile Val Ile Ala Ile Asn Pro Ser Val Pro Glu Asp
                35                  40                  45

Glu Lys Leu Ile Gln Asn Ile Lys Glu Met Val Thr Gln Ala Ser
                50                  55                  60

Thr His Leu Phe His Ala Thr Lys Gln Arg Ala Tyr Phe Arg Asn
65              70                  75

Val Ser Ile Leu Ile Pro Met Thr Tyr Lys Ser Lys Ser Glu Tyr
                80                  85                  90

Leu Ile Pro Lys Gln Glu Thr Tyr Asp Gln Ala Asp Val Ile Val
                95                  100                 105

Ala Asp Leu Tyr Leu Lys Tyr Gly Asp Asp Pro Tyr Thr Leu Gln
                110                 115                 120

Tyr Gly Gln Cys Gly Asp Lys Gly Gln Tyr Ile His Phe Thr Pro
                125                 130                 135

Asn Phe Leu Leu Thr Asn Asn Leu Ala Thr Tyr Gly Pro Arg Gly
                140                 145                 150

Lys Val Phe Val His Gly Trp Ala His Leu Arg Trp Gly Val Phe
                155                 160                 165

Asp Glu Tyr Asn Val Asp Gln Pro Phe Tyr Ile Ser Arg Arg Asn
                170                 175                 180

```
Thr Thr Glu Ala Thr Arg Cys Ser Thr Arg Ile Thr Val Tyr Met
            185                 190                 195

Val Leu Asn Glu Cys Lys Gly Ala Ser Cys Ile Ala Arg Pro Phe
            200                 205                 210

Arg Arg Asp Ser Gln Thr Gly Leu Tyr Glu Ala Lys Cys Thr Phe
            215                 220                 225

Ile Pro Lys Arg Ser Gln Thr Ala Lys Glu Ser Ile Val Phe Met
            230                 235                 240

Gln Asn Leu Asp Ser Val Thr Glu Phe Cys Thr Glu Lys Thr His
            245                 250                 255

Asn Lys Glu Ala Pro Asn Leu Tyr Asn Lys Met Cys Asn His Arg
            260                 265                 270

Ser Thr Trp Asp Val Ile Met Ser Ser Glu Asp Phe Gln His Leu
            275                 280                 285

Ser Pro Met Thr Glu Ile Asn Leu Pro Arg Pro Thr Phe Ser Leu
            290                 295                 300

Leu Lys Ser Lys Gln Arg Val Val Cys Leu Val Leu Asp Lys Ser
            305                 310                 315

Gly Ser Met Asn Ala Glu Asp Arg Leu Phe Arg Met Asn Gln Ala
            320                 325                 330

Ala Glu Leu Tyr Leu Ile Gln Ile Ile Glu Lys Gly Ser Leu Val
            335                 340                 345

Gly Leu Val Thr Phe Asp Ser Phe Ala Lys Ile Gln Ser Lys Leu
            350                 355                 360

Ile Lys Ile Ile Asp Asp Asn Thr Tyr Gln Lys Ile Thr Ala Asn
            365                 370                 375

Leu Pro Gln Glu Ala Asp Gly Gly Thr Ser Ile Cys Arg Gly Leu
            380                 385                 390

Lys Ala Gly Phe Gln Ala Ile Pro Gln Ser Asn Gln Ser Thr Phe
            395                 400                 405

Gly Ser Glu Ile Ile Leu Leu Thr Asp Gly Glu Asp Tyr Gln Ile
            410                 415                 420

Ser Leu Cys Phe Gly Glu Val Lys Gln Ser Gly Thr Val Ile His
            425                 430                 435

Thr Ile Ala Leu Gly Pro Ser Ala Asp Glu Glu Leu Glu Thr Leu
            440                 445                 450

Ser Asn Met Thr Gly Leu His Lys Gly His Cys Tyr Thr Glu Ser
            455                 460                 465

Ser Tyr Ser Ala Gly Lys Phe Ile Phe Cys Gly His Arg Phe Tyr
            470                 475                 480

Ala His Lys Asn Ile Asn Gly Leu Ile Asp Ala Phe Ser Arg Ile
            485                 490                 495

Ser Ser Arg Ser Gly Ser Ile Ser Gln Gln Ala Leu Gln Leu Glu
            500                 505                 510

Ser Lys Thr Leu Asn Ile Pro Ala Lys Lys Trp Ile Asn Gly Thr
            515                 520                 525

Val Pro Val Asp Ser Thr Val Arg Asn Asp Thr Ser Phe Val Val
            530                 535                 540

Thr Trp Thr Ile Gln Lys Pro Ala Ile Ile Leu Gln Asp Pro Lys
            545                 550                 555

Gly Lys Lys Tyr Thr Thr Ser Asp Phe Gln Glu Gly Glu Leu Asn
            560                 565                 570
```

-continued

```
Ile Arg Ser Ala Arg Leu Arg Ile Pro Gly Ile Ala Glu Thr Gly
            575                 580                 585

Ile Trp Thr Tyr Ser Val Arg Asn Asn His Thr Lys Ser Gln Leu
            590                 595                 600

Leu Thr Val Thr Met Thr Thr Arg Ala Arg Ser Pro Thr Thr Leu
            605                 610                 615

Pro Val Ile Ala Thr Ala His Ser Met Gln Asn Thr Ala His Tyr
            620                 625                 630

Pro Ser Pro Val Ile Val Tyr Ala Cys Val Ser Gln Gly Phe Leu
            635                 640                 645

Pro Val Leu Gly Ile Asn Val Thr Ala Ile Ile Glu Asn Glu Glu
            650                 655                 660

Gly His Gln Val Thr Leu Glu Leu Cys Asp Asn Gly Ala Gly Ala
            665                 670                 675

Asp Ser Val Lys Asn Asp Gly Ile Tyr Ser Arg Tyr Phe Thr Asp
            680                 685                 690

Tyr His Gly Asn Gly Arg Tyr Ser Leu Lys Val Leu Thr Gln Ala
            695                 700                 705

Arg Lys Asn Thr Ala Arg Leu Ser Gln Gln Asn Lys Ala Leu
            710                 715                 720

Tyr Val Pro Arg Tyr Ala Glu Asn Gly Lys Ile Ile Leu Asn Pro
            725                 730                 735

Ser Lys Pro Glu Val Thr Asp Asp Val Glu Gly Ala Gln Thr Asp
            740                 745                 750

Asp Phe Ser Arg Leu Thr Ser Gly Gly Ser Phe Thr Val Ser Gly
            755                 760                 765

Val Pro Pro Asn Gly Asn His Ser Gln Val Phe Ser Pro Gly Lys
            770                 775                 780

Ile Val Asp Leu Glu Ala Lys Phe Gln Gly Asp His Ile Gln Leu
            785                 790                 795

Ser Trp Thr Ala Pro Gly Lys Val Leu Asp Lys Gly Arg Ala Glu
            800                 805                 810

Ser Tyr Ile Ile Arg Ile Ser Lys His Phe Leu Asp Leu Gln Glu
            815                 820                 825

Asp Phe Asp Lys Ala Ala Leu Ile Asn Thr Ser Gly Leu Ile Pro
            830                 835                 840

Lys Glu Pro Gly Ser Val Glu Ser Phe Glu Phe Lys Pro Glu Pro
            845                 850                 855

Ser Lys Ile Glu Asn Gly Thr Thr Phe Tyr Ile Ala Ile Gln Ala
            860                 865                 870

Ile His Glu Ala Asn Val Thr Ser Glu Val Ser Asn Ile Ala Gln
            875                 880                 885

Ala Thr Asn Phe Ile Pro Pro Gln Glu Pro Ser Ile Pro Asp Leu
            890                 895                 900

Gly Thr Asn Ile Ser Ala Ile Ser Leu Ala Ile Phe Gly Leu Ala
            905                 910                 915

Val Ile Leu Ser Ile Phe Tyr Thr Arg Asn Tyr Ile Arg Thr Gln
            920                 925                 930

Ile Gln Cys Tyr Thr Tyr Leu Val Asn Ile Tyr Leu Lys Phe Asn
            935                 940                 945

Leu Leu Tyr Leu Leu Ser Ile Ile Lys Leu Ile Ile Tyr Lys
            950                 955                 960

Val Lys Tyr Lys Ser Cys Lys Phe Pro Asn Tyr Leu Ile Asn Tyr
```

```
                965                 970                 975
Tyr Tyr Leu Ser Tyr Tyr Met Leu Ile Lys Met Ser Ile Ser Phe
                    980                 985                 990

Pro Val Trp Asn Asn Pro Leu Ile Asn Phe
                995                 1000

<210> SEQ ID NO 31
<211> LENGTH: 2970
<212> TYPE: DNA
<213> ORGANISM: Homo sapiens

<400> SEQUENCE: 31
acctaaaacc ttgcaagttc aggaagaaac catctgcatc catattgaaa            50
acctgacaca atgtatgcag caggctcagt gtgagtgaac tggaggcttc           100 tctacaac atg acc caa agg agc att gca ggt cct att tgc aac        144 ctg aag ttt gtg act ctc ctg gtt gcc tta agt tca gaa ctc cca     189 ttc ctg gga gct gga gta cag ctt caa gac aat ggg tat aat gga    234 ttg ctc att gca att aat cct cag gta cct gag aat cag aac ctc    279 atc tca aac att aag gaa atg ata act gaa gct tca ttt tac cta    324 ttt aat gct acc aag aga aga gta ttt ttc aga aat ata aag att    369 tta ata cct gcc aca tgg aaa gct aat aat aac agc aaa ata aaa    414 caa gaa tca tat gaa aag gca aat gtc ata gtg act gac tgg tat    459 ggg gca cat gga gat gat cca tac acc cta caa tac aga ggg tgt    504 gga aaa gag gga aaa tac att cat ttc aca cct aat ttc cta ctg    549 aat gat aac tta aca gct ggc tac gga tca cga ggc cga gtg ttt    594 gtc cat gaa tgg gcc cac ctc cgt tgg ggt gtg ttc gat gag tat    639 aac aat gac aaa cct ttc tac ata aat ggg caa aat caa att aaa    684 gtg aca agg tgt tca tct gac atc aca ggc att ttt gtg tgt gaa    729 aaa ggt cct tgc ccc caa gaa aac tgt att att agt aag ctt ttt    774 aaa gaa gga tgc acc ttt atc tac aat agc acc caa aat gca act    819 gca tca ata atg ttc atg caa agt tta tct tct gtg gtt gaa ttt    864 tgt aat gca agt acc cac aac caa gaa gca cca aac cta cag aac    909 cag atg tgc agc ctc aga agt gca tgg gat gta atc aca gac tct    954 gct gac ttt cac cac agc ttt ccc atg aat ggg act gag ctt cca    999 cct cct ccc aca ttc tcg ctt gta cag gct ggt gac aaa gtg tc   1044 tgt tta gtg ctg gat gtg tcc agc aag atg gca gag gct gac aga   1089 ctc ctt caa cta caa caa gcc gca gaa ttt tat ttg atg cag att   1134 gtt gaa att cat acc ttc gtg ggc att gcc agt ttc gac agc aaa   1179 gga gag atc aga gcc cag cta cac caa att aac agc aat gat gat   1224 cga aag ttg ctg gtt tca tat ctg ccc acc act gta tca gct aaa   1269 aca gac atc agc att tgt tca ggg ctt aag aaa gga ttt gag gtg   1314 gtt gaa aaa ctg aat gga aaa gct tat ggc tct gtg atg ata tta   1359 gtg acc agc gga gat gat aag ctt ctt ggc aat gc tta ccc act   1404 gtg ctc agc agt ggt tca aca att cac tcc att gcc ctg ggt tca   1449
```

| | |
|---|---|
| tct gca gcc cca aat ctg gag gaa tta tca cgt ctt aca gga ggt | 1494 |
| tta aag ttc ttt gtt cca gat ata tca aac tcc aat agc atg att | 1539 |
| gat gct ttc agt aga att tcc tct gga act gga gac att ttc cag | 1584 |
| caa cat att cag ctt gaa agt aca ggt gaa aat gtc aaa cct cac | 1629 |
| cat caa ttg aaa aac aca gtg act gtg gat aat act gtg ggc aac | 1674 |
| gac act atg ttt cta gtt acg tgg cag gcc agt ggt cct cct gag | 1719 |
| att ata tta ttt gat cct gat gga cga aaa tac tac aca aat aat | 1764 |
| ttt atc acc aat cta act ttt cgg aca gct agt ctt tgg att cca | 1809 |
| gga aca gct aag cct ggg cac tgg act tac acc ctg aac aat acc | 1854 |
| cat cat tct ctg caa gcc ctg aaa gtg aca gtg acc tct cgc gcc | 1899 |
| tcc aac tca gct gtg ccc cca gcc act gtg gaa gcc ttt gtg aa | 1944 |
| aga gac agc ctc cat ttt cct cat cct gtg atg att tat gcc aat | 1989 |
| gtg aaa cag gga ttt tat ccc att ctt aat gcc act gtc act gcc | 2034 |
| aca gtt gag cca gag act gga gat cct gtt acg ctg aga ctc ctt | 2079 |
| gat gat gga gca ggt gct gat gtt ata aaa aat gat gga att tac | 2124 |
| tcg agg tat ttt ttc tcc ttt gct gca aat ggt aga tat agc ttg | 2169 |
| aaa gtg cat gtc aat cac tct ccc agc ata agc acc cca gcc cac | 2214 |
| tct att cca ggg agt cat gct atg tat gta cca ggt tac aca gca | 2259 |
| aac ggt aat att cag atg aat gct cca agg aaa tca gta ggc aga | 2304 |
| aat gag gag gag cga aag tgg ggc ttt agc cga gtc agc tca gga | 2349 |
| ggc tcc ttt tca gtg ctg gga gtt cca gct ggc ccc cac cct gat | 2394 |
| gtg ttt cca cca tgc aaa att att gac ctg gaa gct gta aaa gta | 2439 |
| gaa gag gaa ttg acc cta tct tgg aca gca cct gga gaa gac ttt | 2484 |
| gat cag ggc cag gct aca agc tat gaa ata aga atg agt aaa agt | 2529 |
| cta cag aat atc caa gat gac ttt aac aat gct att tta gta aat | 2574 |
| aca tca aag cga aat cct cag caa gct ggc atc agg gag ata ttt | 2619 |
| acg ttc tca ccc cag att tcc acg aat gga cct gaa cat cag cca | 2664 |
| aat gga gaa aca cat gaa agc cac aga att tat gtt gca ata cga | 2709 |
| gca atg gat agg aac tcc tta cag tct gct gta tct aac att gcc | 2754 |
| cag gcg cct ctg ttt att ccc ccc aat tct gat cct gta cct gcc | 2799 |
| aga gat tat ctt ata ttg aaa gga gtt tta aca gca atg ggt ttg | 2844 |
| ata gga atc att tgc ctt att ata gtt gtg aca cat cat act tta | 2889 |
| agc agg aaa aag aga gca gac aag aaa gag aat gga aca aaa tta | 2934 |
| tta taaataaata tccaaagtgt cttccttctc aaa | 2970 |

<210> SEQ ID NO 32
<211> LENGTH: 943
<212> TYPE: PRT
<213> ORGANISM: Homo sapiens

<400> SEQUENCE: 32

Met Thr Gln Arg Ser Ile Ala Gly Pro Ile Cys Asn Leu Lys Phe
1               5                   10                  15

-continued

Val Thr Leu Leu Val Ala Leu Ser Ser Glu Leu Pro Phe Leu Gly
            20                  25                  30

Ala Gly Val Gln Leu Gln Asp Asn Gly Tyr Asn Gly Leu Leu Ile
            35                  40                  45

Ala Ile Asn Pro Gln Val Pro Glu Asn Gln Asn Leu Ile Ser Asn
            50                  55                  60

Ile Lys Glu Met Ile Thr Glu Ala Ser Phe Tyr Leu Phe Asn Ala
            65                  70                  75

Thr Lys Arg Arg Val Phe Phe Arg Asn Ile Lys Ile Leu Ile Pro
            80                  85                  90

Ala Thr Trp Lys Ala Asn Asn Asn Ser Lys Ile Lys Gln Glu Ser
            95                 100                 105

Tyr Glu Lys Ala Asn Val Ile Val Thr Asp Trp Tyr Gly Ala His
           110                 115                 120

Gly Asp Asp Pro Tyr Thr Leu Gln Tyr Arg Gly Cys Gly Lys Glu
           125                 130                 135

Gly Lys Tyr Ile His Phe Thr Pro Asn Phe Leu Leu Asn Asp Asn
           140                 145                 150

Leu Thr Ala Gly Tyr Gly Ser Arg Gly Arg Val Phe Val His Glu
           155                 160                 165

Trp Ala His Leu Arg Trp Gly Val Phe Asp Glu Tyr Asn Asn Asp
           170                 175                 180

Lys Pro Phe Tyr Ile Asn Gly Gln Asn Gln Ile Lys Val Thr Arg
           185                 190                 195

Cys Ser Ser Asp Ile Thr Gly Ile Phe Val Cys Glu Lys Gly Pro
           200                 205                 210

Cys Pro Gln Glu Asn Cys Ile Ile Ser Lys Leu Phe Lys Glu Gly
           215                 220                 225

Cys Thr Phe Ile Tyr Asn Ser Thr Gln Asn Ala Thr Ala Ser Ile
           230                 235                 240

Met Phe Met Gln Ser Leu Ser Ser Val Val Glu Phe Cys Asn Ala
           245                 250                 255

Ser Thr His Asn Gln Glu Ala Pro Asn Leu Gln Asn Gln Met Cys
           260                 265                 270

Ser Leu Arg Ser Ala Trp Asp Val Ile Thr Asp Ser Ala Asp Phe
           275                 280                 285

His His Ser Phe Pro Met Asn Gly Thr Glu Leu Pro Pro Pro
           290                 295                 300

Thr Phe Ser Leu Val Gln Ala Gly Asp Lys Val Val Cys Leu Val
           305                 310                 315

Leu Asp Val Ser Ser Lys Met Ala Glu Ala Asp Arg Leu Leu Gln
           320                 325                 330

Leu Gln Gln Ala Ala Glu Phe Tyr Leu Met Gln Ile Val Glu Ile
           335                 340                 345

His Thr Phe Val Gly Ile Ala Ser Phe Asp Ser Lys Gly Glu Ile
           350                 355                 360

Arg Ala Gln Leu His Gln Ile Asn Ser Asn Asp Asp Arg Lys Leu
           365                 370                 375

Leu Val Ser Tyr Leu Pro Thr Thr Val Ser Ala Lys Thr Asp Ile
           380                 385                 390

Ser Ile Cys Ser Gly Leu Lys Lys Gly Phe Glu Val Val Glu Lys
           395                 400                 405

-continued

```
Leu Asn Gly Lys Ala Tyr Gly Ser Val Met Ile Leu Val Thr Ser
            410                 415                 420

Gly Asp Asp Lys Leu Leu Gly Asn Cys Leu Pro Thr Val Leu Ser
            425                 430                 435

Ser Gly Ser Thr Ile His Ser Ile Ala Leu Gly Ser Ser Ala Ala
            440                 445                 450

Pro Asn Leu Glu Glu Leu Ser Arg Leu Thr Gly Gly Leu Lys Phe
            455                 460                 465

Phe Val Pro Asp Ile Ser Asn Ser Asn Ser Met Ile Asp Ala Phe
            470                 475                 480

Ser Arg Ile Ser Ser Gly Thr Gly Asp Ile Phe Gln Gln His Ile
            485                 490                 495

Gln Leu Glu Ser Thr Gly Glu Asn Val Lys Pro His His Gln Leu
            500                 505                 510

Lys Asn Thr Val Thr Val Asp Asn Thr Val Gly Asn Asp Ile Met
            515                 520                 525

Phe Leu Val Thr Trp Gln Ala Ser Gly Pro Pro Glu Ile Ile Leu
            530                 535                 540

Phe Asp Pro Asp Gly Arg Lys Tyr Tyr Thr Asn Asn Phe Thr Thr
            545                 550                 555

Asn Leu Thr Phe Arg Thr Ala Ser Leu Trp Ile Pro Gly Thr Ala
            560                 565                 570

Lys Pro Gly His Trp Thr Tyr Thr Leu Asn Asn Thr His His Ser
            575                 580                 585

Leu Gln Ala Leu Lys Val Thr Val Thr Ser Arg Ala Ser Asn Ser
            590                 595                 600

Ala Val Pro Pro Ala Thr Val Glu Ala Phe Val Glu Arg Asp Ser
            605                 610                 615

Leu His Phe Pro His Pro Val Met Ile Tyr Ala Asn Val Lys Gln
            620                 625                 630

Gly Phe Tyr Pro Ile Ile Asn Ala Thr Val Thr Ala Thr Val Glu
            635                 640                 645

Pro Glu Thr Gly Asp Pro Val Thr Leu Arg Leu Leu Asp Asp Gly
            650                 655                 660

Ala Gly Ala Asp Val Ile Lys Asn Asp Gly Ile Tyr Ser Arg Tyr
            665                 670                 675

Phe Phe Ser Phe Ala Ala Asn Gly Arg Tyr Ser Leu Lys Val His
            680                 685                 690

Val Asn His Ser Pro Ser Ile Ser Thr Pro Ala His Ser Ile Pro
            695                 700                 705

Gly Ser His Ala Met Tyr Val Pro Gly Tyr Thr Ala Asn Gly Asn
            710                 715                 720

Ile Gln Met Asn Ala Pro Arg Lys Ser Val Gly Arg Asn Glu Glu
            725                 730                 735

Glu Arg Lys Trp Gly Phe Ser Arg Val Ser Ser Gly Gly Ser Phe
            740                 745                 750

Ser Val Leu Gly Val Pro Ala Gly Pro His Pro Asp Val Phe Pro
            755                 760                 765

Pro Cys Lys Ile Ile Asp Leu Glu Ala Val Lys Val Glu Glu Glu
            770                 775                 780

Leu Thr Leu Ser Trp Thr Ala Pro Gly Glu Asp Phe Asp Gln Gly
            785                 790                 795

Gln Ala Thr Ser Tyr Glu Ile Arg Met Ser Lys Ser Leu Gln Asn
```

```
                    800                 805                 810
Ile Gln Asp Asp Phe Asn Asn Ala Ile Leu Val Asn Thr Ser Lys
            815                 820                 825
Arg Asn Pro Gln Gln Ala Gly Ile Arg Glu Ile Phe Thr Phe Ser
            830                 835                 840
Pro Gln Ile Ser Thr Asn Gly Pro Glu His Gln Pro Asn Gly Glu
            845                 850                 855
Thr His Glu Ser His Arg Ile Tyr Val Ala Ile Arg Ala Met Asp
            860                 865                 870
Arg Asn Ser Leu Gln Ser Ala Val Ser Asn Ile Ala Gln Ala Pro
            875                 880                 885
Leu Phe Ile Pro Pro Asn Ser Asp Pro Val Pro Ala Arg Asp Tyr
            890                 895                 900
Leu Ile Leu Lys Gly Val Leu Thr Ala Met Gly Leu Ile Gly Ile
            905                 910                 915
Ile Cys Leu Ile Ile Val Val Thr His His Thr Leu Ser Arg Lys
            920                 925                 930
Lys Arg Ala Asp Lys Lys Glu Asn Gly Thr Lys Leu Leu
            935                 940     943

<210> SEQ ID NO 33
<211> LENGTH: 3022
<212> TYPE: DNA
<213> ORGANISM: Mus musculus

<400> SEQUENCE: 33
actggagcag tgcgacc atg gtg cca ggg ctg cag gtc ctt ctg ttc        47
ctc acc ctg cat ctc ctg cag aac aca gag agc tcc atg gtg cat       92
ctc aac agc aat gga tac gag ggt gtg gtc att gcc att aac ccc      137
agt gtg cca gag gac gaa agg ctc atc cca agc ata aag gaa atg      182
gta act caa gct tct acc tac ctg ttt gaa gcc agc caa gga aga      227
gtt tat ttc agg aac ata agc ata tta gtc ccg atg acc tgg aag      272
tcg aaa tct gag tac tta atg cca aaa cga gaa tcg tac gac aaa      317
gca gac gtc ata gtt gcg gat cct cac ctg caa cat gga gac gac      362
ccc tac acc ctt cag tat gga cag tgt ggg gac aga gga cag tac      407
ata cac ttc act cca aac ttc cta ctc act gat aac ttg cgt atc      452
tat gga ccc cga ggc aga gtc ttt gtc cat gag tgg gcc cat ctc      497
cgg tgg gga gta ttt gat gag tat aac gtg gac cgg tca ctt tac      542
att tct aga aag aac act ata gaa gca aca agg tgc tcc gcc agc      587
atc aca ggc aag aag gtg gtc cac gag tgt cag aga ggc agc tgt      632
gtg aca agg gcg tgc cgg cgt gac tcg aag aca cgg ctg tat gaa      677
ccc aaa tgt aca ttt atc cca gac aaa ata cag aca gct ggg gcc      722
tcc ata atg ttc atg caa aac ctc aat tct gtg gtt gaa ttt tgc      767
aca gaa aat aac cac aat gca gaa gcc cca aac cta caa aac aaa      812
atg tgc aat cgc aga agc acg tgg gat gta atc aag acg tct gct      857
gac ttt cag aat gcc cct ccc atg aga gga aca gaa gcc cct cct      902
cca cct aca ttt tat ctg ctc aag tcc aga agg cga gtg gtg tgc      947
```

-continued

```
ttg gtg ctg gat aaa tct gga agc atg gac aaa gaa gac cgt ctt      992
att cga atg aat caa gca gca gaa ctg tac tta act caa att gtg     1037
gaa aag gag tct atg gtt gga tta gtc aca ttt gac agc gct gcc     1082
cac atc caa aat tat cta ata aaa ata acg agt agt agt gac tac     1127
caa aag atc acc gca aac ctc ccc caa cag gct tct ggt gga act     1172
tca att tgc cat gga ctc cag gca gga ttt cag gca att acc tcc     1217
agt gac cag agc act tcc ggt tct gag atc gta ttg ctg aca gat     1262
ggg gaa gat aat gga ata cgt tcc tgc ttt gag gcc gtc tct cgc     1307
agc ggt gcc atc atc cac acc atc gct ctg ggg cct tcg cgt gcc     1352
cga gaa ctg gag act ctg tcg gac atg aca gga ggg ctt cgt ttc     1397
tat gcc aac aaa gac cta aac agc ctt atc gat gct ttc agt aga     1442
att tca tct aca agt ggc agc gtc tcc cag cag gct ctg cag ttg     1487
gag agc aaa gcc ttc gat gtc aga gca ggg gca tgg ata aac ggt     1532
aca gta cct ctg gac agt acc gtc ggc aac gac acg ttc ttt gtt     1577
atc acc tgg atg gta aaa aag cca gaa atc att ctt caa gat cca     1622
aaa gga aaa aaa tat aca acc tca gat ttc caa gat gat aaa cta     1667
aac atc cgg tct gct aga ctt caa ata ccg ggc act gca gag aca     1712
ggt act tgg act tac agc tac acg ggt acc aag tct cag ttg att     1757
aca atg aca gtg acc act cga gca aga agt ccc acc atg gaa cca     1802
ctc ctg ggc tac tgc tac atg agt cag agc aca gcc cag tac cct     1847
agc cgg atg att gtg tac gca cgg gtc agc caa gga ttt tgc cct     1892
gtt ctg gga gcc aat gtc aca gcc ctc ata gaa gct gaa cat gga     1937
cat caa gtc acc ttg gag ctc tgg gac aat ggg gca ggt gct gat     1982
atc gtt aaa aat gat ggc atc tac aca aga tac ttt aca gat tat     2027
cat gga aat ggt aga tac agc cta aaa gtg cgt gtc cag gca caa     2072
aga aac aaa acc aga ctg agc tta aga cag aag aac aag tct tta     2117
tat ata cct ggc tat gtg gaa aat ggt aaa att gta ctg aat cca     2162
ccc aga cca gat gtc caa gaa gaa gcc ata gaa gct aca gtg gaa     2207
gac ttc aac aga gta acc tct gga ggg tcg ttt act gtg tct gga     2252
gcg ccc cct gat ggc gac cac gct cgt gtg ttc cca cca agt aaa     2297
gtc aca gac ctg gag gct gag ttt ata ggt gat tat att cac ctt     2342
aca tgg acg gcc cct ggc aag gtt ctc gac aat gga aga gca cat     2387
aga tac atc atc aga atg agc cag cat cct ctg atc tca gaa       2432
gat ttt aac aat gct act tta gtg aat gct cca gtc tga ata cct     2477
aaa gaa gct ggc tca aaa gaa gca ttt aaa ttc aaa cca gaa act     2522
ttt aaa ata gca aat ggc atc cag ctc tac att gca atc cag gca     2567
gac aat gaa gcc agt ctc acc tct gag gtc tcc aac atc gca cag     2612
gct gtc aag ctt act tct cta gaa gat agt atc tct gca ctg ggt     2657
gat gat att tct gca atc tct atg aca att tgg ggg tta act gtg     2702
att ttt aac tct att tta aac tagaagatag aatggcacta              2743
```

-continued

```
aaatgcaatc ctgtacatat ttgctaagtg ttgctttaga atgtctttac         2793
tacacactca aaggctgcct gtcaacaatt gtaatataga agttcatatt         2843
caaagttgaa atcccgagt tactaacaca attcttttgc tatatgtaga          2893
tcaagattaa cagttcctca ttcaatttct taattgttcc atttactatg         2943 gaataagat atccattctc ttttcacagt gtgatgcaag ttcactttgt          2993
atatgaaaat aaaaaatttg tacaactcg                                3022
```

<210> SEQ ID NO 34
<211> LENGTH: 902
<212> TYPE: PRT
<213> ORGANISM: Mus musculus

<400> SEQUENCE: 34

```
Met Val Pro Gly Leu Gln Val Leu Leu Phe Leu Thr Leu His Leu
                 5                  10                  15

Leu Gln Asn Thr Glu Ser Ser Met Val His Leu Asn Ser Asn Gly
                20                  25                  30

Tyr Glu Gly Val Val Ile Ala Ile Asn Pro Ser Val Pro Glu Asp
                35                  40                  45

Glu Arg Leu Ile Pro Ser Ile Lys Glu Met Val Thr Gln Ala Ser
                50                  55                  60

Thr Tyr Leu Phe Glu Ala Ser Gln Gly Arg Val Tyr Phe Arg Asn
                65                  70                  75

Ile Ser Ile Leu Val Pro Met Thr Trp Lys Ser Lys Ser Glu Tyr
                80                  85                  90

Leu Met Pro Lys Arg Glu Ser Tyr Asp Lys Ala Asp Val Ile Val
                95                  100                 105

Ala Asp Pro His Leu Gln His Gly Asp Asp Pro Tyr Thr Leu Gln
                110                 115                 120

Tyr Gly Gln Cys Gly Asp Arg Gly Gln Tyr Ile His Phe Thr Pro
                125                 130                 135

Asn Phe Leu Leu Thr Asp Asn Leu Arg Ile Tyr Gly Pro Arg Gly
                140                 145                 150

Arg Val Phe Val His Glu Trp Ala His Leu Arg Trp Gly Val Phe
                155                 160                 165

Asp Glu Tyr Asn Val Asp Arg Ser Pro Tyr Ile Ser Arg Lys Asn
                170                 175                 180

Thr Ile Glu Ala Thr Arg Cys Ser Ala Ser Ile Thr Gly Lys Lys
                185                 190                 195

Val Val His Glu Cys Gln Arg Gly Ser Cys Val Thr Arg Ala Cys
                200                 205                 210

Arg Arg Asp Ser Lys Thr Arg Leu Tyr Glu Pro Lys Cys Thr Phe
                215                 220                 225

Ile Pro Asp Lys Ile Gln Thr Ala Gly Ala Ser Ile Met Phe Met
                230                 235                 240

Gln Asn Leu Asn Ser Val Val Glu Phe Cys Thr Glu Asn His
                245                 250                 255

Asn Ala Glu Ala Pro Asn Leu Gln Asn Lys Met Cys Asn Arg Arg
                260                 265                 270

Ser Thr Trp Asp Val Ile Lys Thr Ser Ala Asp Phe Gln Asn Ala
                275                 280                 285

Pro Pro Met Arg Gly Thr Glu Ala Pro Pro Pro Thr Phe Tyr
```

-continued

```
                290                 295                 300
Leu Leu Lys Ser Arg Arg Val Val Cys Leu Val Leu Asp Lys
            305                 310                 315
Ser Gly Ser Met Asp Lys Glu Asp Arg Leu Ile Arg Met Asn Gln
            320                 325                 330
Ala Ala Glu Leu Tyr Leu Thr Gln Ile Val Glu Lys Glu Ser Met
            335                 340                 345
Val Gly Leu Val Thr Phe Asp Ser Ala His Ile Gln Asn Tyr
            350                 355                 360
Leu Ile Lys Ile Thr Ser Ser Ser Asp Tyr Gln Lys Ile Thr Ala
            365                 370                 375
Asn Leu Pro Gln Gln Ala Ser Gly Gly Thr Ser Ile Cys His Gly
            380                 385                 390
Leu Gln Ala Gly Phe Gln Ala Ile Thr Ser Ser Asp Gln Ser Thr
            395                 400                 405
Ser Gly Ser Glu Ile Val Leu Leu Thr Asp Gly Glu Asp Asn Gly
            410                 415                 420
Ile Arg Ser Cys Phe Glu Ala Val Ser Arg Ser Gly Ala Ile Ile
            425                 430                 435
His Thr Ile Ala Leu Gly Pro Ser Arg Ala Arg Glu Leu Glu Thr
            440                 445                 450
Leu Ser Asp Met Thr Gly Gly Leu Arg Phe Tyr Ala Asn Lys Asp
            455                 460                 465
Leu Asn Ser Leu Ile Asp Ala Phe Ser Arg Ile Ser Ser Thr Ser
            470                 475                 480
Gly Ser Val Ser Gln Gln Ala Leu Gln Leu Glu Ser Lys Ala Phe
            485                 490                 495
Asp Val Arg Ala Gly Ala Trp Ile Asn Gly Thr Val Pro Leu Asp
            500                 505                 510
Ser Thr Val Gly Asn Asp Thr Phe Phe Val Ile Thr Trp Met Val
            515                 520                 525
Lys Lys Pro Glu Ile Ile Leu Gln Asp Pro Lys Gly Lys Lys Tyr
            530                 535                 540
Thr Thr Ser Asp Phe Gln Asp Asp Lys Leu Asn Ile Arg Ser Ala
            545                 550                 555
Arg Leu Gln Ile Pro Gly Thr Ala Glu Thr Gly Thr Trp Thr Tyr
            560                 565                 570
Ser Tyr Thr Gly Thr Lys Ser Gln Leu Ile Thr Met Thr Val Thr
            575                 580                 585
Thr Arg Ala Arg Ser Pro Thr Met Glu Pro Leu Leu Gly Tyr Cys
            590                 595                 600
Tyr Met Ser Gln Ser Thr Ala Gln Tyr Pro Ser Arg Met Ile Val
            605                 610                 615
Tyr Ala Arg Val Ser Gln Gly Phe Leu Pro Val Leu Gly Ala Asn
            620                 625                 630
Val Thr Ala Leu Ile Glu Ala Glu His Gly His Gln Val Thr Leu
            635                 640                 645
Glu Leu Trp Asp Asn Gly Ala Gly Ala Asp Ile Val Lys Asn Asp
            650                 655                 660
Gly Ile Tyr Thr Arg Tyr Phe Thr Asp Tyr His Gly Asn Gly Arg
            665                 670                 675
Tyr Ser Leu Lys Val Arg Val Gln Ala Gln Arg Asn Lys Thr Arg
            680                 685                 690
```

Leu Ser Leu Arg Gln Lys Asn Lys Ser Leu Tyr Ile Pro Gly Tyr
              695                 700                 705

Val Glu Asn Gly Lys Ile Val Leu Asn Pro Pro Arg Pro Asp Val
          710                 715                 720

Gln Glu Glu Ala Ile Glu Ala Thr Val Glu Asp Phe Asn Arg Val
      725                 730                 735

Thr Ser Gly Gly Ser Phe Thr Val Ser Gly Ala Pro Pro Asp Gly
  740                 745                 750

Asp His Ala Arg Val Phe Pro Pro Ser Lys Val Thr Asp Leu Glu
755                 760                 765

Ala Glu Phe Ile Gly Asp Tyr Ile His Leu Thr Trp Thr Ala Pro
            770                 775                 780

Gly Lys Val Leu Asp Asn Gly Arg Ala His Arg Tyr Ile Ile Arg
        785                 790                 795

Met Ser Gln His Pro Leu Asp Leu Gln Glu Asp Phe Asn Asn Ala
    800                 805                 810

Thr Leu Val Asn Ala Ser Ser Leu Ile Pro Lys Glu Ala Gly Ser
815                 820                 825

Lys Glu Ala Phe Lys Phe Lys Pro Glu Thr Phe Lys Ile Ala Asn
            830                 835                 840

Gly Ile Gln Leu Tyr Ile Ala Ile Gln Ala Asp Asn Glu Ala Ser
        845                 850                 855

Leu Thr Ser Glu Val Ser Asn Ile Ala Gln Ala Val Lys Leu Thr
    860                 865                 870

Ser Leu Glu Asp Ser Ile Ser Ala Leu Gly Asp Asp Ile Ser Ala
875                 880                 885

Ile Ser Met Thr Ile Trp Gly Leu Thr Val Ile Phe Asn Ser Ile
            890                 895                 900

Leu Asn
   902

<210> SEQ ID NO 35
<211> LENGTH: 18
<212> TYPE: DNA
<213> ORGANISM: Artificial sequence
<220> FEATURE:
<223> OTHER INFORMATION: Amplification primer

<400> SEQUENCE: 35
gaaccttgcc aggggccg                                                  18

<210> SEQ ID NO 36
<211> LENGTH: 22
<212> TYPE: DNA
<213> ORGANISM: Artificial sequence
<220> FEATURE:
<223> OTHER INFORMATION: Amplification primer

<400> SEQUENCE: 36
ccacgtgctt ctgcgattgc ac                                             22

<210> SEQ ID NO 37
<211> LENGTH: 31
<212> TYPE: DNA
<213> ORGANISM: Artificial sequence
<220> FEATURE:
<223> OTHER INFORMATION: Amplification primer

<400> SEQUENCE: 37
gcggccgcaa tggggccatt taagagttct g                             31

<210> SEQ ID NO 38
<211> LENGTH: 30
<212> TYPE: DNA
<213> ORGANISM: Artificial sequence
<220> FEATURE:
<223> OTHER INFORMATION: Amplification primer

<400> SEQUENCE: 38
gcggccgcag ccctaggcta ttgacagctg                               30

<210> SEQ ID NO 39
<211> LENGTH: 24
<212> TYPE: DNA
<213> ORGANISM: Artificial sequence
<220> FEATURE:
<223> OTHER INFORMATION: Amplification primer

<400> SEQUENCE: 39
agaatcaaga tgaacacaga actc                                     24

<210> SEQ ID NO 40
<211> LENGTH: 26
<212> TYPE: DNA
<213> ORGANISM: Artificial sequence
<220> FEATURE:
<223> OTHER INFORMATION: Amplification primer

<400> SEQUENCE: 40
caaggtattt cacaacttat gacacg                                   26

<210> SEQ ID NO 41
<211> LENGTH: 29
<212> TYPE: DNA
<213> ORGANISM: Artificial sequence
<220> FEATURE:
<223> OTHER INFORMATION: Amplification primer

<400> SEQUENCE: 41
gcggccgcta caacatgacc caaaggagc                                29

<210> SEQ ID NO 42
<211> LENGTH: 43
<212> TYPE: DNA
<213> ORGANISM: Artificial sequence
<220> FEATURE:
<223> OTHER INFORMATION: Amplification primer

<400> SEQUENCE: 42
gcggccgcga cactttggat atttatttat aataattttg ttc                43

<210> SEQ ID NO 43
<211> LENGTH: 19
<212> TYPE: DNA
<213> ORGANISM: Artificial sequence
<220> FEATURE:
<223> OTHER INFORMATION: Amplification primer

<400> SEQUENCE: 43
cctttatgtt ttgaatgag                                           19

<210> SEQ ID NO 44
<211> LENGTH: 22
<212> TYPE: DNA

```
<213> ORGANISM: Artificial sequence
<220> FEATURE:
<223> OTHER INFORMATION: Amplification primer

<400> SEQUENCE: 44
caactatgac atctgcctgg tc                                              22

<210> SEQ ID NO 45
<211> LENGTH: 25
<212> TYPE: DNA
<213> ORGANISM: Artificial sequence
<220> FEATURE:
<223> OTHER INFORMATION: Amplification primer

<400> SEQUENCE: 45
cacaaagcta ggctaagtca agaac                                           25

<210> SEQ ID NO 46
<211> LENGTH: 903
<212> TYPE: PRT
<213> ORGANISM: Unknown
<220> FEATURE:
<223> OTHER INFORMATION: Calcium sensitive chloride channel from bovine
      tracheal epithelium (Cunningham et al., 1995, J. Biol Chem.,
      270:31016-31026)

<400> SEQUENCE: 46
```

Met Val Pro Arg Leu Thr Val Ile Leu Phe Leu Thr Leu His Leu
                 5                  10                  15

Leu Pro Gly Met Lys Ser Ser Met Val Asn Leu Ile Asn Asn Gly
             20                  25                  30

Tyr Asp Gly Ile Val Ile Ala Ile Asn Pro Ser Val Pro Glu Asp
             35                  40                  45

Glu Lys Leu Ile Gln Asn Ile Lys Glu Met Val Thr Glu Ala Ser
             50                  55                  60

Thr Tyr Leu Phe His Ala Thr Lys Arg Arg Val Tyr Phe Arg Asn
             65                  70                  75

Val Ser Ile Leu Ile Pro Met Thr Trp Lys Ser Lys Ser Glu Tyr
             80                  85                  90

Leu Met Pro Lys Gln Glu Ser Tyr Asp Gln Ala Glu Val Ile Val
             95                  100                 105

Ala Asn Pro Tyr Leu Lys His Gly Asp Asp Pro Tyr Thr Leu Gln
             110                 115                 120

Tyr Gly Arg Cys Gly Glu Lys Gly Gln Tyr Ile His Phe Thr Pro
             125                 130                 135

Asn Phe Leu Leu Thr Asn Asn Leu Pro Ile Tyr Gly Ser Arg Gly
             140                 145                 150

Arg Ala Phe Val His Glu Trp Ala His Leu Arg Trp Gly Ile Phe
             155                 160                 165

Asp Glu Tyr Asn Gly Asp Gln Pro Phe Tyr Ile Ser Arg Arg Asn
             170                 175                 180

Thr Ile Glu Ala Thr Arg Cys Ser Thr His Ile Thr Gly Thr Asn
             185                 190                 195

Val Ile Val Lys Cys Gln Gly Gly Ser Cys Ile Thr Arg Pro Cys
             200                 205                 210

Arg Arg Asp Ser Gln Thr Gly Leu Tyr Glu Ala Lys Cys Thr Phe
             215                 220                 225

Ile Pro Glu Lys Ser Gln Thr Ala Arg Glu Ser Ile Met Phe Met
             230                 235                 240

```
Gln Ser Leu His Ser Val Thr Glu Phe Cys Thr Glu Lys Thr His
                245                 250                 255

Asn Val Glu Ala Pro Asn Leu Gln Asn Lys Met Cys Asn Gly Lys
            260                 265                 270

Ser Thr Trp Asp Val Ile Met Asn Ser Thr Asp Phe Gln Asn Thr
        275                 280                 285

Ser Pro Met Thr Glu Met Asn Pro Pro Thr Gln Pro Thr Phe Ser
    290                 295                 300

Leu Leu Lys Ser Lys Gln Arg Val Val Cys Leu Val Leu Asp Lys
305                 310                 315

Ser Gly Ser Met Ser Ser Glu Asp Arg Leu Phe Arg Met Asn Gln
                320                 325                 330

Ala Ala Glu Leu Phe Leu Ile Gln Ile Ile Glu Lys Gly Ser Leu
            335                 340                 345

Val Gly Met Val Thr Phe Asp Ser Val Ala Glu Ile Arg Asn Asn
        350                 355                 360

Leu Thr Lys Ile Thr Asp Asp Asn Val Tyr Glu Asn Ile Thr Ala
    365                 370                 375

Asn Leu Pro Gln Glu Ala Asn Gly Gly Thr Ser Ile Cys Arg Gly
380                 385                 390

Leu Lys Ala Gly Phe Gln Ala Ile Ile Gln Ser Gln Gln Ser Thr
                395                 400                 405

Ser Gly Ser Glu Ile Ile Leu Leu Thr Asp Gly Glu Asp Asn Glu
            410                 415                 420

Ile His Ser Cys Ile Glu Glu Val Lys Gln Ser Gly Val Ile Ile
        425                 430                 435

His Thr Val Ala Leu Gly Pro Ser Ala Ala Lys Glu Leu Glu Thr
    440                 445                 450

Leu Ser Asp Met Thr Gly Gly His Arg Phe Tyr Ala Asn Lys Asp
455                 460                 465

Ile Asn Gly Leu Thr Asn Ala Phe Ser Arg Ile Ser Ser Arg Ser
                470                 475                 480

Gly Ser Ile Thr Gln Gln Thr Ile Gln Leu Glu Ser Lys Ala Leu
            485                 490                 495

Ala Ile Thr Glu Lys Lys Trp Val Asn Gly Thr Val Pro Val Asp
        500                 505                 510

Ser Thr Ile Gly Asn Asp Thr Phe Phe Val Val Thr Trp Thr Ile
    515                 520                 525

Lys Lys Pro Glu Ile Leu Leu Gln Asp Pro Lys Gly Lys Lys Tyr
530                 535                 540

Lys Thr Ser Asp Phe Lys Glu Asp Lys Leu Asn Ile His Ser Ala
                545                 550                 555

Arg Leu Arg Ile Pro Gly Ile Ala Glu Thr Gly Thr Trp Thr Tyr
            560                 565                 570

Ser Leu Leu Asn Asn His Ala Ser Pro Gln Ile Leu Thr Val Thr
        575                 580                 585

Val Thr Thr Arg Ala Arg Ser Pro Thr Thr Pro Val Thr Ala
    590                 595                 600

Thr Ala His Met Asn Gln Asn Thr Ala His Tyr Pro Ser Pro Val
605                 610                 615

Ile Val Tyr Ala Gln Val Ser Gln Gly Phe Leu Pro Val Leu Gly
                620                 625                 630
```

-continued

```
Ile Asn Val Thr Ala Ile Ile Glu Thr Glu Asp Gly His Gln Val
                635             640                 645

Thr Leu Glu Leu Trp Asp Asn Gly Ala Gly Ala Asp Ala Thr Lys
                650             655                 660

Asp Asp Gly Val Tyr Ser Arg Tyr Phe Thr Thr Tyr Asp Thr Asn
                665             670                 675

Gly Arg Tyr Ser Val Lys Val His Ala Glu Ala Arg Asn Asn Thr
                680             685                 690

Ala Arg Leu Ser Leu Arg Gln Pro Gln Asn Lys Ala Leu Tyr Ile
                695             700                 705

Pro Gly Tyr Ile Glu Asn Gly Lys Ile Leu Asn Pro Pro Arg
                710             715                 720

Pro Glu Val Lys Asp Asp Leu Ala Lys Ala Glu Ile Glu Asp Phe
                725             730                 735

Ser Arg Leu Thr Ser Gly Gly Ser Phe Thr Val Ser Gly Ala Pro
                740             745                 750

Pro Gly Asn His Pro Ser Val Leu Pro Pro Asn Lys Ile Thr Asp
                755             760                 765

Leu Glu Ala Lys Phe Lys Glu Asp His Ile Gln Leu Ser Trp Thr
                770             775                 780

Ala Pro Ala Asn Val Leu Asp Lys Gly Lys Ala Asn Ser Tyr Ile
                785             790                 795

Ile Arg Ile Ser Lys Ser Phe Leu Asp Leu Gln Lys Asp Phe Asp
                800             805                 810

Asn Ala Thr Leu Val Asn Thr Ser Ser Leu Lys Pro Lys Glu Ala
                815             820                 825

Gly Ser Asp Glu Asn Phe Glu Phe Lys Pro Glu Pro Phe Arg Ile
                830             835                 840

Glu Asn Gly Thr Asn Phe Tyr Ile Ala Val Gln Ala Ile Asn Glu
                845             850                 855

Ala Asn Leu Thr Ser Glu Val Ser Asn Ile Ala Gln Ala Ile Lys
                860             865                 870

Phe Ile Pro Met Pro Glu Asp Ser Val Pro Ala Leu Gly Thr Lys
                875             880                 885

Ile Ser Ala Ile Asn Leu Ala Ile Phe Ala Leu Ala Met Ile Leu
                890             895                 900

Ser Ile Val
        903
```

<210> SEQ ID NO 47
<211> LENGTH: 10
<212> TYPE: PRT
<213> ORGANISM: Homo sapiens
<220> FEATURE:
<223> OTHER INFORMATION: partial sequence of human c-myc protein

<400> SEQUENCE: 47

```
Glu Gln Lys Leu Ile Ser Glu Glu Asp Leu
              5                  10
```

<210> SEQ ID NO 48
<211> LENGTH: 675
<212> TYPE: PRT
<213> ORGANISM: homo sapiens
<220> FEATURE:
<223> OTHER INFORMATION: amino acids 1-675 of SEQ ID NO:32 which make
      up putative 90 kDa subunit of     hCLCA2

```
<400> SEQUENCE: 48

Met Thr Gln Arg Ser Ile Ala Gly Pro Ile Cys Asn Leu Lys Phe
1               5                   10                  15

Val Thr Leu Leu Val Ala Leu Ser Ser Glu Leu Pro Phe Leu Gly
            20                  25                  30

Ala Gly Val Gln Leu Gln Asp Asn Gly Tyr Asn Gly Leu Leu Ile
        35                  40                  45

Ala Ile Asn Pro Gln Val Pro Glu Asn Gln Asn Leu Ile Ser Asn
    50                  55                  60

Ile Lys Glu Met Ile Thr Glu Ala Ser Phe Tyr Leu Phe Asn Ala
65                  70                  75

Thr Lys Arg Arg Val Phe Phe Arg Asn Ile Lys Ile Leu Ile Pro
            80                  85                  90

Ala Thr Trp Lys Ala Asn Asn Asn Ser Lys Ile Lys Gln Glu Ser
        95                  100                 105

Tyr Glu Lys Ala Asn Val Ile Val Thr Asp Trp Tyr Gly Ala His
    110                 115                 120

Gly Asp Asp Pro Tyr Thr Leu Gln Tyr Arg Gly Cys Gly Lys Glu
125                 130                 135

Gly Lys Tyr Ile His Phe Thr Pro Asn Phe Leu Leu Asn Asp Asn
            140                 145                 150

Leu Thr Ala Gly Tyr Gly Ser Arg Gly Arg Val Phe Val His Glu
        155                 160                 165

Trp Ala His Leu Arg Trp Gly Val Phe Asp Glu Tyr Asn Asn Asp
    170                 175                 180

Lys Pro Phe Tyr Ile Asn Gly Gln Asn Gln Ile Lys Val Thr Arg
185                 190                 195

Cys Ser Ser Asp Ile Thr Gly Ile Phe Val Cys Glu Lys Gly Pro
            200                 205                 210

Cys Pro Gln Glu Asn Cys Ile Ile Ser Lys Leu Phe Lys Glu Gly
        215                 220                 225

Cys Thr Phe Ile Tyr Asn Ser Thr Gln Asn Ala Thr Ala Ser Ile
    230                 235                 240

Met Phe Met Gln Ser Leu Ser Ser Val Val Glu Phe Cys Asn Ala
245                 250                 255

Ser Thr His Asn Gln Glu Ala Pro Asn Leu Gln Asn Gln Met Cys
            260                 265                 270

Ser Leu Arg Ser Ala Trp Asp Val Ile Thr Asp Ser Ala Asp Phe
        275                 280                 285

His His Ser Phe Pro Met Asn Gly Thr Glu Leu Pro Pro Pro
    290                 295                 300

Thr Phe Ser Leu Val Gln Ala Gly Asp Lys Val Val Cys Leu Val
305                 310                 315

Leu Asp Val Ser Ser Lys Met Ala Glu Ala Asp Arg Leu Leu Gln
            320                 325                 330

Leu Gln Gln Ala Ala Glu Phe Tyr Leu Met Gln Ile Val Glu Ile
        335                 340                 345

His Thr Phe Val Gly Ile Ala Ser Phe Asp Ser Lys Gly Glu Ile
    350                 355                 360

Arg Ala Gln Leu His Gln Ile Asn Ser Asn Asp Asp Arg Lys Leu
365                 370                 375

Leu Val Ser Tyr Leu Pro Thr Thr Val Ser Ala Lys Thr Asp Ile
            380                 385                 390
```

```
Ser Ile Cys Ser Gly Leu Lys Lys Gly Phe Glu Val Val Glu Lys
            395                 400                 405

Leu Asn Gly Lys Ala Tyr Gly Ser Val Met Ile Leu Val Thr Ser
            410                 415                 420

Gly Asp Asp Lys Leu Leu Gly Asn Cys Leu Pro Thr Val Leu Ser
            425                 430                 435

Ser Gly Ser Thr Ile His Ser Ile Ala Leu Gly Ser Ser Ala Ala
            440                 445                 450

Pro Asn Leu Glu Glu Leu Ser Arg Leu Thr Gly Gly Leu Lys Phe
            455                 460                 465

Phe Val Pro Asp Ile Ser Asn Ser Asn Ser Met Ile Asp Ala Phe
            470                 475                 480

Ser Arg Ile Ser Ser Gly Thr Gly Asp Ile Phe Gln Gln His Ile
            485                 490                 495

Gln Leu Glu Ser Thr Gly Glu Asn Val Lys Pro His His Gln Leu
            500                 505                 510

Lys Asn Thr Val Thr Val Asp Asn Thr Val Gly Asn Asp Ile Met
            515                 520                 525

Phe Leu Val Thr Trp Gln Ala Ser Gly Pro Pro Glu Ile Ile Leu
            530                 535                 540

Phe Asp Pro Asp Gly Arg Lys Tyr Tyr Thr Asn Asn Phe Thr Thr
            545                 550                 555

Asn Leu Thr Phe Arg Thr Ala Ser Leu Trp Ile Pro Gly Thr Ala
            560                 565                 570

Lys Pro Gly His Trp Thr Tyr Thr Leu Asn Asn Thr His His Ser
            575                 580                 585

Leu Gln Ala Leu Lys Val Thr Val Thr Ser Arg Ala Ser Asn Ser
            590                 595                 600

Ala Val Pro Pro Ala Thr Val Glu Ala Phe Val Glu Arg Asp Ser
            605                 610                 615

Leu His Phe Pro His Pro Val Met Ile Tyr Ala Asn Val Lys Gln
            620                 625                 630

Gly Phe Tyr Pro Ile Ile Asn Ala Thr Val Thr Ala Thr Val Glu
            635                 640                 645

Pro Glu Thr Gly Asp Pro Val Thr Leu Arg Leu Leu Asp Asp Gly
            650                 655                 660

Ala Gly Ala Asp Val Ile Lys Asn Asp Gly Ile Tyr Ser Arg Tyr
            665                 670                 675

<210> SEQ ID NO 49
<211> LENGTH: 268
<212> TYPE: PRT
<213> ORGANISM: homo sapiens
<220> FEATURE:
<223> OTHER INFORMATION: amino acids 676-943 of SEQ ID NO:32 which make
      up putative 35 kDa subunit of hCLCA2

<400> SEQUENCE: 49

Phe Phe Ser Phe Ala Ala Asn Gly Arg Tyr Ser Leu Lys Val His
1               5                   10                  15

Val Asn His Ser Pro Ser Ile Ser Thr Pro Ala His Ser Ile Pro
            20                  25                  30

Gly Ser His Ala Met Tyr Val Pro Gly Tyr Thr Ala Asn Gly Asn
            35                  40                  45

Ile Gln Met Asn Ala Pro Arg Lys Ser Val Gly Arg Asn Glu Glu
```

```
                    50                  55                  60
Glu Arg Lys Trp Gly Phe Ser Arg Val Ser Ser Gly Gly Ser Phe
                65                  70                  75
Ser Val Leu Gly Val Pro Ala Gly Pro His Pro Asp Val Phe Pro
                80                  85                  90
Pro Cys Lys Ile Ile Asp Leu Glu Ala Val Lys Val Glu Glu Glu
                95                 100                 105
Leu Thr Leu Ser Trp Thr Ala Pro Gly Glu Asp Phe Asp Gln Gly
               110                 115                 120
Gln Ala Thr Ser Tyr Glu Ile Arg Met Ser Lys Ser Leu Gln Asn
               125                 130                 135
Ile Gln Asp Asp Phe Asn Asn Ala Ile Leu Val Asn Thr Ser Lys
               140                 145                 150
Arg Asn Pro Gln Gln Ala Gly Ile Arg Glu Ile Phe Thr Phe Ser
               155                 160                 165
Pro Gln Ile Ser Thr Asn Gly Pro Glu His Gln Pro Asn Gly Glu
               170                 175                 180
Thr His Glu Ser His Arg Ile Tyr Val Ala Ile Arg Ala Met Asp
               185                 190                 195
Arg Asn Ser Leu Gln Ser Ala Val Ser Asn Ile Ala Gln Ala Pro
               200                 205                 210
Leu Phe Ile Pro Pro Asn Ser Asp Pro Val Pro Ala Arg Asp Tyr
               215                 220                 225
Leu Ile Leu Lys Gly Val Leu Thr Ala Met Gly Leu Ile Gly Ile
               230                 235                 240
Ile Cys Leu Ile Ile Val Val Thr His His Thr Leu Ser Arg Lys
               245                 250                 255
Lys Arg Ala Asp Lys Lys Glu Asn Gly Thr Lys Leu Leu
               260                 265         268

<210> SEQ ID NO 50
<211> LENGTH: 10
<212> TYPE: PRT
<213> ORGANISM: artificial sequence
<220> FEATURE:
<223> OTHER INFORMATION:

<400> SEQUENCE: 50

Ala Phe Ser Arg Ile Ser Ser Gly Thr Gly
1               5                   10

<210> SEQ ID NO 51
<211> LENGTH: 10
<212> TYPE: PRT
<213> ORGANISM: artificial sequence
<220> FEATURE:
<223> OTHER INFORMATION:

<400> SEQUENCE: 51

Gly Phe Ser Arg Val Ser Ser Gly Gly Ser
1               5                   10

<210> SEQ ID NO 52
<211> LENGTH: 10
<212> TYPE: PRT
<213> ORGANISM: artificial sequence
<220> FEATURE:
<223> OTHER INFORMATION:

<400> SEQUENCE: 52
```

```
Cys Phe Ser Arg Val Ser Ser Gly Gly Ser
1               5                   10
```

<210> SEQ ID NO 53
<211> LENGTH: 244
<212> TYPE: PRT
<213> ORGANISM: homo sapiens
<220> FEATURE:
<223> OTHER INFORMATION:

<400> SEQUENCE: 53

```
Tyr Ser Val Lys Val Arg Ala Leu Gly Gly Val Asn Ala Ala Arg
1               5                   10                  15

Arg Arg Val Ile Pro Gln Gln Ser Gly Ala Leu Tyr Ile Pro Gly
                20                  25                  30

Trp Ile Glu Asn Asp Glu Ile Gln Trp Asn Pro Pro Arg Pro Glu
                35                  40                  45

Ile Asn Lys Asp Asp Val Gln His Lys Gln Val Cys Phe Ser Arg
                50                  55                  60

Thr Ser Ser Gly Gly Ser Phe Val Ala Ser Asp Val Pro Asn Ala
                65                  70                  75

Pro Ile Pro Asp Leu Phe Pro Pro Gly Gln Ile Thr Asp Leu Lys
                80                  85                  90

Ala Glu Ile His Gly Gly Ser Leu Ile Asn Leu Thr Trp Thr Ala
                95                  100                 105

Pro Gly Asp Asp Tyr Asp His Gly Thr Ala His Lys Tyr Ile Ile
                110                 115                 120

Arg Ile Ser Thr Ser Ile Leu Asp Leu Arg Asp Lys Phe Asn Glu
                125                 130                 135

Ser Leu Gln Val Asn Thr Thr Ala Leu Ile Pro Lys Glu Ala Asn
                140                 145                 150

Ser Glu Glu Val Phe Leu Phe Lys Pro Glu Asn Ile Thr Phe Glu
                155                 160                 165

Asn Gly Thr Asp Leu Phe Ile Ala Ile Gln Ala Val Asp Lys Val
                170                 175                 180

Asp Leu Lys Ser Glu Ile Ser Asn Ile Ala Arg Val Ser Leu Phe
                185                 190                 195

Ile Pro Pro Gln Thr Pro Glu Thr Pro Ser Pro Asp Glu Thr
                200                 205                 210

Ser Ala Pro Cys Pro Asn Ile His Ile Asn Ser Thr Ile Pro Gly
                215                 220                 225

Ile His Ile Leu Lys Ile Met Trp Lys Trp Ile Gly Glu Leu Gln
                230                 235                 240

Leu Ser Ile Ala
            244
```

<210> SEQ ID NO 54
<211> LENGTH: 10
<212> TYPE: PRT
<213> ORGANISM: artificial sequence
<220> FEATURE:
<223> OTHER INFORMATION:

<400> SEQUENCE: 54

```
Ala Phe Val Arg Ile Ser Ser Gly Thr Gly
1               5                   10
```

```
<210> SEQ ID NO 55
<211> LENGTH: 10
<212> TYPE: PRT
<213> ORGANISM: artificial sequence
<220> FEATURE:
<223> OTHER INFORMATION:

<400> SEQUENCE: 55

Ala Phe Ser Arg Ile Ser Ser Thr Ser Gly
1               5                   10

<210> SEQ ID NO 56
<211> LENGTH: 10
<212> TYPE: PRT
<213> ORGANISM: artificial sequence
<220> FEATURE:
<223> OTHER INFORMATION:

<400> SEQUENCE: 56

Asp Phe Asn Arg Val Thr Ser Gly Gly Ser
1               5                   10

<210> SEQ ID NO 57
<211> LENGTH: 10
<212> TYPE: PRT
<213> ORGANISM: artificial sequence
<220> FEATURE:
<223> OTHER INFORMATION:

<400> SEQUENCE: 57

Ala Phe Ser Arg Ile Ser Ser Arg Ser Gly
1               5                   10

<210> SEQ ID NO 58
<211> LENGTH: 10
<212> TYPE: PRT
<213> ORGANISM: artificial sequence
<220> FEATURE:
<223> OTHER INFORMATION:

<400> SEQUENCE: 58

Asp Phe Ser Arg Leu Thr Ser Gly Gly Ser
1               5                   10

<210> SEQ ID NO 59
<211> LENGTH: 10
<212> TYPE: PRT
<213> ORGANISM: artificial sequence
<220> FEATURE:
<223> OTHER INFORMATION:

<400> SEQUENCE: 59

Ala Phe Gly Ala Leu Ser Ser Gly Asn Gly
1               5                   10

<210> SEQ ID NO 60
<211> LENGTH: 35
<212> TYPE: PRT
<213> ORGANISM: homo sapiens
<220> FEATURE:
<223> OTHER INFORMATION:

<400> SEQUENCE: 60

Lys Val Ser Val Phe Gln Thr Asp Met Arg Phe Glu Lys Leu Glu
1               5                   10                  15

Pro Trp Pro Asn Ser Asp Pro Pro Phe Ser Phe Lys Asn Val Ile
                20                  25                  30
```

```
Ser Leu Thr Glu Asp
                35

<210> SEQ ID NO 61
<211> LENGTH: 6
<212> TYPE: PRT
<213> ORGANISM: artificial sequence
<220> FEATURE:
<221> NAME/KEY: unsure
<222> LOCATION: 2, 4, 5; 2 is Ser or Asn, 4 is Ile or Leu or Val,
      5 is Ser or Thr
<223> OTHER INFORMATION:

<400> SEQUENCE: 61

Phe Xaa Arg Xaa Xaa Ser
1               5   6

<210> SEQ ID NO 62
<211> LENGTH: 39
<212> TYPE: PRT
<213> ORGANISM: homo sapiens
<220> FEATURE:
<223> OTHER INFORMATION:

<400> SEQUENCE: 62

Lys Thr Val Met Pro Tyr Ile Ser Thr Thr Pro Ala Lys Leu Arg
1               5                   10                  15

Asn Pro Cys Thr Ser Gly Gln Asn Cys Thr Thr Pro Phe Ser Tyr
                20                  25                  30

Lys Asn Val Leu Ser Leu Thr Asn Lys
                35              39

<210> SEQ ID NO 63
<211> LENGTH: 40
<212> TYPE: PRT
<213> ORGANISM: E.coli
<220> FEATURE:
<223> OTHER INFORMATION:

<400> SEQUENCE: 63

Glu Glu Glu Glu Cys Glu Glu Cys Cys Cys Cys Cys Cys Cys
1               5                   10                  15

Cys Cys Cys Cys Cys Cys Cys Cys Cys Cys Cys Cys Cys
                20                  25                  30

Cys Glu Glu Glu Glu Glu Cys Cys Cys Cys
                35                  40
```